(12) United States Patent
Johnson et al.

(10) Patent No.: US 10,736,805 B2
(45) Date of Patent: *Aug. 11, 2020

(54) ADAPTIVE COMPRESSION THERAPY SYSTEMS AND METHODS

(71) Applicant: Radial Medical, Inc., Woodside, CA (US)

(72) Inventors: Eric Johnson, Woodside, CA (US); Thomas J. Fogarty, Portola Valley, CA (US); Sylvester Lucatero, East Palo Alto, CA (US); Gilbert Laroya, Santa Clara, CA (US); James K. Wall, San Francisco, CA (US); Conrad Salinas, Santa Clara, CA (US)

(73) Assignee: RADIAL MEDICAL, INC., Woodside, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/133,508

(22) Filed: Sep. 17, 2018

(65) Prior Publication Data

US 2019/0254906 A1 Aug. 22, 2019

Related U.S. Application Data

(63) Continuation of application No. 15/499,850, filed on Apr. 27, 2017, now Pat. No. 10,076,462.
(Continued)

(51) Int. Cl.
*A61H 1/00* (2006.01)
*A61B 5/02* (2006.01)
(Continued)

(52) U.S. Cl.
CPC ............. *A61H 1/006* (2013.01); *A41D 1/005* (2013.01); *A61B 5/021* (2013.01); *A61B 5/022* (2013.01);
(Continued)

(58) Field of Classification Search
CPC ............ A61H 7/001; A61H 2201/5061; A61H 2201/5084; A61H 2230/065;
(Continued)

(56) References Cited

U.S. PATENT DOCUMENTS 651,962 A 6/1900 Boghean
718,766 A 1/1903 Ingram
(Continued)

FOREIGN PATENT DOCUMENTS

DE 19505765 A1 10/1995
DE 20213196 U1 1/2004
(Continued)

OTHER PUBLICATIONS

Mosti et al.; "Comparison between a new, two-component compression system with zinc paste bandages for leg ulcer healing: a prospective, multicenter, randomized, controlled trial monitoring sub-bandage pressures"; Wounds; vol. 23(5); pp. 126-134; May 2011.

(Continued)

*Primary Examiner* — Steven O Douglas
(74) *Attorney, Agent, or Firm* — Shay Glenn LLP

(57) ABSTRACT

Systems, devices and methods for providing active and/or passive compression therapy to a body part can include a compression device worn over a compression stocking. The compression device can have a pulley based drive train that is driven by a motor to tighten and loosen compression elements, such as compression straps, in a precise, rapid, and balanced manner. Sensors can be used in the compression device and/or compression stockings to provide feedback to modulate the compression treatment parameters.

17 Claims, 35 Drawing Sheets

Related U.S. Application Data

(60) Provisional application No. 62/328,574, filed on Apr. 27, 2016.

(51) Int. Cl.

| | | |
|---|---|---|
| *A61B 5/021* | (2006.01) | |
| *A61B 5/022* | (2006.01) | |
| *A61B 5/0295* | (2006.01) | |
| *A61H 31/00* | (2006.01) | |
| *A61F 5/01* | (2006.01) | |
| *A61F 5/02* | (2006.01) | |
| *A41D 1/00* | (2018.01) | |
| *A61B 5/00* | (2006.01) | |
| *A61H 7/00* | (2006.01) | |
| *A61B 5/0205* | (2006.01) | |
| *A61B 5/024* | (2006.01) | |
| *A61H 11/00* | (2006.01) | |
| *A43B 3/00* | (2006.01) | |
| *A43B 7/14* | (2006.01) | |
| *A43C 1/06* | (2006.01) | |
| *A43C 11/16* | (2006.01) | |
| *A43B 7/00* | (2006.01) | |

(52) U.S. Cl.
CPC ...... *A61B 5/02007* (2013.01); *A61B 5/02042* (2013.01); *A61B 5/0295* (2013.01); *A61B 5/4842* (2013.01); *A61B 5/4848* (2013.01); *A61F 5/01* (2013.01); *A61F 5/013* (2013.01); *A61F 5/0123* (2013.01); *A61F 5/02* (2013.01); *A61H 7/001* (2013.01); *A61H 31/004* (2013.01); *A61H 31/005* (2013.01); *A61H 31/006* (2013.01); *A61H 31/008* (2013.01); *A43B 3/0015* (2013.01); *A43B 7/00* (2013.01); *A43B 7/146* (2013.01); *A43C 1/06* (2013.01); *A43C 11/16* (2013.01); *A43C 11/165* (2013.01); *A61B 5/002* (2013.01); *A61B 5/0022* (2013.01); *A61B 5/024* (2013.01); *A61B 5/0205* (2013.01); *A61B 5/02141* (2013.01); *A61B 5/418* (2013.01); *A61B 5/4238* (2013.01); *A61B 5/4255* (2013.01); *A61B 5/4836* (2013.01); *A61B 5/6812* (2013.01); *A61B 5/6824* (2013.01); *A61B 5/6828* (2013.01); *A61B 5/6829* (2013.01); *A61H 2011/005* (2013.01); *A61H 2201/0103* (2013.01); *A61H 2201/0176* (2013.01); *A61H 2201/0192* (2013.01); *A61H 2201/1215* (2013.01); *A61H 2201/165* (2013.01); *A61H 2201/50* (2013.01); *A61H 2201/501* (2013.01); *A61H 2201/5038* (2013.01); *A61H 2201/5046* (2013.01); *A61H 2201/5061* (2013.01); *A61H 2201/5064* (2013.01); *A61H 2201/5069* (2013.01); *A61H 2201/5071* (2013.01); *A61H 2201/5084* (2013.01); *A61H 2201/5089* (2013.01); *A61H 2205/06* (2013.01); *A61H 2205/067* (2013.01); *A61H 2205/084* (2013.01); *A61H 2205/10* (2013.01); *A61H 2209/00* (2013.01); *A61H 2230/045* (2013.01); *A61H 2230/065* (2013.01); *A61H 2230/208* (2013.01); *A61H 2230/255* (2013.01); *A61H 2230/305* (2013.01); *A61H 2230/505* (2013.01); *A61H 2230/60* (2013.01); *A61H 2230/625* (2013.01); *A61H 2230/655* (2013.01); *A61H 2230/85* (2013.01)

(58) Field of Classification Search
CPC ........ A61H 2230/208; A61H 2230/255; A61H 2230/305; A61B 5/4842; A61B 5/4848
See application file for complete search history.

(56) References Cited

U.S. PATENT DOCUMENTS

| | | |
|---|---|---|
| 2,118,699 A | 5/1938 | Chappell |
| 2,486,667 A | 11/1949 | Meister |
| 2,528,843 A | 11/1950 | Poor |
| 2,781,041 A | 2/1957 | Weinberg |
| 3,094,116 A | 6/1963 | Logan et al. |
| 3,683,897 A | 8/1972 | Shield et al. |
| 3,804,084 A | 4/1974 | Lehman |
| 3,853,121 A | 12/1974 | Mizrachy et al. |
| 3,859,989 A | 1/1975 | Spielberg |
| 3,862,629 A | 1/1975 | Rotta |
| 3,935,984 A | 2/1976 | Lichowsky et al. |
| 3,942,518 A | 3/1976 | Tenteris et al. |
| 3,993,053 A | 11/1976 | Grossan |
| 4,004,579 A | 1/1977 | Dedo |
| 4,029,087 A | 6/1977 | Dye et al. |
| 4,054,129 A | 10/1977 | Byars et al. |
| 4,079,962 A | 3/1978 | Frechin |
| 4,206,765 A | 6/1980 | Huber |
| 4,207,876 A | 6/1980 | Annis |
| 4,243,039 A | 1/1981 | Haifa |
| 4,253,449 A | 3/1981 | Arkans et al. |
| 4,320,746 A | 3/1982 | Arkans et al. |
| 4,333,181 A | 6/1982 | Corriero |
| 4,375,217 A | 3/1983 | Arkans |
| 4,396,010 A | 8/1983 | Arkans |
| 4,402,312 A | 9/1983 | Villari et al. |
| 4,574,789 A | 3/1986 | Forster |
| 4,577,622 A | 3/1986 | Jennings |
| 4,583,522 A | 4/1986 | Aronne |
| 4,608,740 A | 9/1986 | Bloys et al. |
| 4,732,140 A | 3/1988 | Stoffregen |
| 4,738,249 A | 4/1988 | Linman et al. |
| 4,754,560 A | 7/1988 | Nerrinck |
| 4,770,164 A | 9/1988 | Lach et al. |
| 4,793,328 A | 12/1988 | Kolstedt et al. |
| 4,841,956 A | 6/1989 | Gardner et al. |
| 4,858,596 A | 8/1989 | Kolstedt et al. |
| 4,865,020 A | 9/1989 | Bullard |
| 4,928,674 A | 5/1990 | Halperin et al. |
| 4,966,396 A | 10/1990 | Dye |
| 4,982,732 A | 1/1991 | Morris et al. |
| 5,003,711 A | 4/1991 | Nerrinck et al. |
| 5,009,222 A | 4/1991 | Her |
| 5,022,387 A | 6/1991 | Hasty |
| 5,027,797 A | 7/1991 | Bullard |
| 5,052,375 A | 10/1991 | Stark et al. |
| 5,108,393 A | 4/1992 | Ruffa |
| 5,117,812 A | 6/1992 | McWhorter |
| 5,186,163 A | 2/1993 | Dye |
| 5,226,874 A | 7/1993 | Heinz et al. |
| 5,263,473 A | 11/1993 | McWhorter |
| 5,277,697 A | 1/1994 | France et al. |
| 5,334,131 A | 8/1994 | Omandam et al. |
| 5,346,461 A | 9/1994 | Heinz et al. |
| 5,383,894 A | 1/1995 | Dye |
| 5,399,153 A | 3/1995 | Caprio et al. |
| 5,407,418 A | 4/1995 | Szpur |
| 5,437,610 A | 8/1995 | Cariapa et al. |
| 5,454,831 A | 10/1995 | Mcewen |
| 5,472,413 A | 12/1995 | Detty |
| 5,496,262 A | 3/1996 | Johnson et al. |
| 5,513,658 A | 5/1996 | Goseki |
| 5,569,297 A | 10/1996 | Makower et al. |
| 5,571,075 A | 11/1996 | Bullard |
| 5,575,761 A | 11/1996 | Hajianpour |
| 5,588,954 A | 12/1996 | Riibando et al. |
| 5,588,955 A | 12/1996 | Johnson, Jr. et al. |
| 5,591,200 A | 1/1997 | Cone et al. |
| 5,626,556 A | 5/1997 | Tobler et al. |

(56) References Cited

U.S. PATENT DOCUMENTS

| | | | |
|---|---|---|---|
| 5,738,637 A | 4/1998 | Kelly et al. |
| 5,769,801 A | 6/1998 | Tumey et al. |
| 5,843,007 A | 12/1998 | McEwen et al. |
| 5,865,776 A | 2/1999 | Springs |
| 5,873,848 A | 2/1999 | Fulkerson |
| 5,951,502 A | 9/1999 | Peeler et al. |
| 5,997,465 A | 12/1999 | Savage et al. |
| 6,007,459 A | 12/1999 | Burgess |
| 6,010,470 A | 1/2000 | Albery et al. |
| 6,010,471 A | 1/2000 | Ben-Noon |
| 6,029,294 A | 2/2000 | Saringer et al. |
| 6,066,106 A | 5/2000 | Sherman et al. |
| 6,077,218 A | 6/2000 | Alferness |
| 6,123,662 A | 9/2000 | Alferness et al. |
| 6,123,681 A | 9/2000 | Brown |
| 6,135,116 A | 10/2000 | Vogel et al. |
| 6,142,962 A | 11/2000 | Mollenauer et al. |
| 6,152,893 A | 11/2000 | Pigg et al. |
| 6,174,295 B1 | 1/2001 | Cantrell et al. |
| 6,202,953 B1 | 3/2001 | Hammerslag |
| 6,231,280 B1 | 5/2001 | Bullen |
| 6,231,532 B1 | 5/2001 | Watson et al. |
| 6,269,500 B1 | 8/2001 | Saringer |
| 6,290,662 B1 | 9/2001 | Morris et al. |
| 6,334,363 B1 | 1/2002 | Testud et al. |
| 6,423,017 B2 | 7/2002 | Brotz |
| 6,436,064 B1 | 8/2002 | Kloecker |
| 6,440,093 B1 | 8/2002 | McEwen et al. |
| 6,450,173 B1 | 9/2002 | Forsell |
| 6,468,237 B1 | 10/2002 | Lina |
| 6,478,757 B1 | 11/2002 | Barak |
| 6,494,852 B1 | 12/2002 | Barak et al. |
| 6,537,237 B1 | 3/2003 | Hopkins et al. |
| 6,551,280 B1 | 4/2003 | Knighton et al. |
| 6,558,338 B1 | 5/2003 | Wasserman |
| 6,589,194 B1 | 7/2003 | Calderon et al. |
| 6,616,620 B2 | 9/2003 | Sherman et al. |
| 6,689,076 B2 | 2/2004 | Saringer |
| 6,780,163 B1 | 8/2004 | Krusenklaus |
| 6,806,573 B2 | 10/2004 | Hu |
| 6,827,670 B1 | 12/2004 | Stark et al. |
| 6,869,408 B2 | 3/2005 | Sherman et al. |
| 6,905,456 B1 | 6/2005 | Brunner et al. |
| 6,939,314 B2 | 9/2005 | Hall et al. |
| 6,945,944 B2 | 9/2005 | Kuiper et al. |
| 6,952,614 B2 | 10/2005 | Choi |
| 6,966,884 B2 | 11/2005 | Waldridge et al. |
| 7,004,919 B2 | 2/2006 | Gaylord et al. |
| 7,025,738 B2 | 4/2006 | Hall |
| 7,044,924 B1 | 5/2006 | Roth et al. |
| 7,127,370 B2 | 10/2006 | Kelly et al. |
| 7,135,007 B2 | 11/2006 | Scott et al. |
| 7,173,161 B1 | 2/2007 | Kandt |
| 7,252,646 B2 | 8/2007 | Bolam et al. |
| 7,270,642 B2 | 9/2007 | Ouchene et al. |
| 7,354,410 B2 | 4/2008 | Perry et al. |
| 7,534,215 B2 | 5/2009 | Saringer |
| 7,559,906 B2 | 7/2009 | Bugo |
| 7,559,908 B2 | 7/2009 | Ravikumar |
| 7,591,796 B1 | 9/2009 | Barak et al. |
| 7,618,384 B2 | 11/2009 | Nardi et al. |
| 7,637,879 B2 | 12/2009 | Barak et al. |
| 7,637,922 B2 | 12/2009 | Johnson et al. |
| D610,263 S | 2/2010 | Dagan et al. |
| 7,819,829 B1 | 10/2010 | Chandran |
| 7,823,219 B2 | 11/2010 | Freund |
| 7,850,629 B2 | 12/2010 | Ravikumar |
| 7,857,777 B2 | 12/2010 | Larson et al. |
| 7,862,525 B2 | 1/2011 | Carkner et al. |
| 7,905,849 B2 | 3/2011 | Park |
| 7,954,204 B2 | 6/2011 | Hammerslag et al. |
| 7,976,486 B2 | 7/2011 | Raley et al. |
| 7,981,066 B2 | 7/2011 | Lewis |
| 8,029,450 B2 | 10/2011 | Brown et al. |
| 8,092,367 B2 | 1/2012 | Raman et al. |
| 8,162,869 B2 | 4/2012 | Graham |
| 8,175,713 B1 | 5/2012 | Cywinski |
| 8,177,734 B2 | 5/2012 | Vess |
| 8,192,380 B2 | 6/2012 | Nardi |
| 8,235,921 B2 | 8/2012 | Rousso et al. |
| 8,235,923 B2 | 8/2012 | Avitable et al. |
| 8,241,233 B2 | 8/2012 | Litton et al. |
| 8,257,289 B2 | 9/2012 | Vess |
| 8,313,450 B2 | 11/2012 | Ben-Nun |
| 8,382,693 B1 | 2/2013 | Guldalian |
| 8,388,557 B2 | 3/2013 | Moomiaie-Qajar et al. |
| 8,394,042 B1 | 3/2013 | Mirza |
| 8,403,870 B2 | 3/2013 | Vess |
| 8,419,665 B2 | 4/2013 | Cook |
| 8,419,666 B2 | 4/2013 | Liu et al. |
| 8,444,582 B2 | 5/2013 | Gobet |
| 8,449,483 B2 | 5/2013 | Eddy |
| 8,523,794 B2 | 9/2013 | Iker et al. |
| 8,527,043 B2 | 9/2013 | Dupelle et al. |
| 8,578,939 B1 | 11/2013 | Kimani Mwangi et al. |
| 8,597,194 B2 | 12/2013 | Barak |
| 8,597,214 B2 | 12/2013 | Von Holgreen |
| 8,636,679 B2 | 1/2014 | Linnane et al. |
| 8,721,575 B2 | 5/2014 | Brown et al. |
| 8,728,016 B2 | 5/2014 | Reeves et al. |
| 8,740,828 B2 | 6/2014 | Brown et al. |
| 8,753,299 B1 | 6/2014 | Waldon, Sr. |
| 8,753,300 B2 | 6/2014 | Deshpande |
| 8,764,690 B2 | 7/2014 | Gough |
| 8,779,230 B2 | 7/2014 | Murphy et al. |
| 8,795,209 B2 | 8/2014 | Herken et al. |
| 8,801,643 B2 | 8/2014 | Deshpande et al. |
| 8,845,562 B2 | 9/2014 | Receveur et al. |
| 8,858,473 B2 | 10/2014 | Olson et al. |
| 8,858,474 B2 | 10/2014 | Olson et al. |
| 8,858,475 B2 | 10/2014 | Olson et al. |
| 8,864,691 B2 | 10/2014 | Olson et al. |
| 8,900,168 B2 | 12/2014 | Yamashiro et al. |
| 8,942,800 B2 | 1/2015 | Thiagrajan et al. |
| 8,992,449 B2 | 3/2015 | Mansfield et al. |
| 9,032,551 B2 | 5/2015 | Hildebrandt |
| 9,033,906 B2 | 5/2015 | Nolan et al. |
| 9,050,202 B2 | 6/2015 | Bache et al. |
| 9,084,713 B2 | 7/2015 | Brown et al. |
| 9,114,054 B2 | 8/2015 | Bennett |
| 9,119,760 B2 | 9/2015 | Purdy et al. |
| 9,161,878 B1 | 10/2015 | Pamplin et al. |
| 9,168,195 B2 | 10/2015 | Sankai |
| 9,168,197 B2 | 10/2015 | Malhi et al. |
| 9,204,799 B2 | 12/2015 | Davies et al. |
| 9,205,021 B2 | 12/2015 | Malhi |
| 9,211,225 B2 | 12/2015 | Farrow et al. |
| 9,211,226 B1 | 12/2015 | Menzel |
| 9,216,122 B2 | 12/2015 | Dzioba et al. |
| 9,248,074 B2 | 2/2016 | Toth |
| 9,265,693 B2 | 2/2016 | Sudarev et al. |
| 9,271,890 B1 | 3/2016 | Pamplin et al. |
| 9,283,135 B2 | 3/2016 | Farrow |
| 9,295,605 B2 | 3/2016 | Yurko et al. |
| 9,326,911 B2 | 5/2016 | Wyatt et al. |
| 9,421,142 B2 | 8/2016 | Malhi et al. |
| 9,433,532 B2 | 9/2016 | Vess |
| 9,433,537 B2 | 9/2016 | Zelka |
| 9,433,711 B2 | 9/2016 | Pratt et al. |
| 9,439,828 B2 | 9/2016 | Mayer et al. |
| 9,522,096 B2 | 12/2016 | Jensen et al. |
| 9,539,166 B2 | 1/2017 | Wild et al. |
| 9,539,173 B2 | 1/2017 | Jeppsson |
| 9,549,867 B1 | 1/2017 | El-Messeiry et al. |
| 9,572,720 B2 | 2/2017 | Hanlon et al. |
| 9,872,790 B2 | 1/2018 | Capra et al. |
| 10,076,462 B2 | 9/2018 | Johnson et al. |
| 2002/0026131 A1 | 2/2002 | Halperin |
| 2002/0052568 A1 | 5/2002 | Houser et al. |
| 2002/0169399 A1 | 11/2002 | Rastegar et al. |
| 2004/0073146 A1 | 4/2004 | Weintraub et al. |
| 2005/0027218 A1 | 2/2005 | Filtvedt et al. |
| 2005/0043657 A1 | 2/2005 | Couvillon |
| 2005/0101887 A1 | 5/2005 | Stark et al. |

(56) References Cited

U.S. PATENT DOCUMENTS

| | | |
|---|---|---|
| 2005/0107725 A1 | 5/2005 | Wild et al. |
| 2005/0267387 A1 | 12/2005 | Baldauf et al. |
| 2005/0273025 A1 | 12/2005 | Houser |
| 2006/0047232 A1 | 3/2006 | Bourne et al. |
| 2006/0058715 A1 | 3/2006 | Hui et al. |
| 2006/0074362 A1 | 4/2006 | Rousso |
| 2006/0079824 A1 | 4/2006 | Munch-Fals et al. |
| 2006/0083623 A1 | 4/2006 | Higgins et al. |
| 2006/0122546 A1 | 6/2006 | Rousso |
| 2006/0135894 A1 | 6/2006 | Linnane et al. |
| 2006/0173238 A1 | 8/2006 | Starkebaum |
| 2007/0038167 A1 | 2/2007 | Tabron et al. |
| 2007/0049852 A1 | 3/2007 | Linnane et al. |
| 2007/0049853 A1 | 3/2007 | Bonnefin et al. |
| 2007/0055188 A1 | 3/2007 | Avni |
| 2007/0173886 A1 | 7/2007 | Rousso et al. |
| 2007/0249976 A1 | 10/2007 | Tucker et al. |
| 2007/0249977 A1 | 10/2007 | Bonnefin et al. |
| 2008/0004548 A1 | 1/2008 | Oshmyansky |
| 2008/0015630 A1 | 1/2008 | Rousso |
| 2008/0039752 A1 | 2/2008 | Rousso |
| 2008/0059239 A1 | 3/2008 | Gerst et al. |
| 2008/0066272 A1 | 3/2008 | Hammerslag et al. |
| 2008/0066574 A1 | 3/2008 | Murata et al. |
| 2008/0071204 A1 | 3/2008 | Linnane |
| 2008/0097268 A1 | 4/2008 | Rousso |
| 2008/0146980 A1 | 6/2008 | Rousso et al. |
| 2008/0243041 A1 | 10/2008 | Brenner et al. |
| 2008/0255481 A1 | 10/2008 | Quintana et al. |
| 2008/0255494 A1 | 10/2008 | Rousso et al. |
| 2008/0262399 A1 | 10/2008 | Kovelman et al. |
| 2008/0269543 A1 | 10/2008 | Rousso |
| 2009/0082707 A1 | 3/2009 | Rumsey |
| 2009/0287109 A1 | 11/2009 | Ferren et al. |
| 2009/0299242 A1 | 12/2009 | Hasegawa |
| 2010/0139057 A1 | 6/2010 | Soderberg et al. |
| 2010/0217167 A1 | 8/2010 | Ingimundarson et al. |
| 2011/0015498 A1 | 1/2011 | Mestrovic et al. |
| 2011/0196189 A1 | 8/2011 | Milbocker |
| 2011/0258876 A1 | 10/2011 | Baker et al. |
| 2011/0319787 A1 | 12/2011 | Lamoise |
| 2012/0004587 A1 | 1/2012 | Nickel et al. |
| 2012/0010547 A1 | 1/2012 | Hinds |
| 2012/0029404 A1 | 2/2012 | Weaver et al. |
| 2012/0065561 A1 | 3/2012 | Ballas et al. |
| 2012/0083712 A1 | 4/2012 | Watson et al. |
| 2012/0253252 A1 | 10/2012 | Weaver |
| 2013/0085430 A1 | 4/2013 | Deshpande et al. |
| 2013/0204106 A1 | 8/2013 | Bennett |
| 2013/0237889 A1 | 9/2013 | Wright et al. |
| 2013/0237891 A1 | 9/2013 | Fryman et al. |
| 2013/0345612 A1 | 12/2013 | Bannister et al. |
| 2014/0068838 A1 | 3/2014 | Beers et al. |
| 2014/0082963 A1 | 3/2014 | Beers |
| 2014/0094725 A1 | 4/2014 | Malhi et al. |
| 2014/0094728 A1 | 4/2014 | Soderberg et al. |
| 2014/0142485 A1 | 5/2014 | Berry et al. |
| 2014/0257156 A1 | 9/2014 | Capra et al. |
| 2014/0276308 A1 | 9/2014 | DiAngelo et al. |
| 2014/0303536 A1 | 10/2014 | Guldalian |
| 2015/0065930 A1 | 3/2015 | Wyatt et al. |
| 2015/0297132 A1 | 10/2015 | Bichel et al. |
| 2015/0297437 A1 | 10/2015 | Neuenhahn et al. |
| 2015/0359700 A1 | 12/2015 | Davis et al. |
| 2015/0374573 A1 | 12/2015 | Horst et al. |
| 2016/0022528 A1 | 1/2016 | Wyatt et al. |
| 2016/0100793 A1 | 4/2016 | Barak |
| 2016/0310310 A1 | 10/2016 | White et al. |
| 2016/0374886 A1 | 12/2016 | Wyatt et al. |
| 2017/0100300 A1 | 4/2017 | Rapp et al. |
| 2017/0128306 A1 | 5/2017 | Chase et al. |
| 2017/0273851 A1 | 9/2017 | Larmer et al. |
| 2017/0312161 A1 | 11/2017 | Johnson et al. |
| 2019/0374421 A1 | 12/2019 | Johnson et al. |

FOREIGN PATENT DOCUMENTS

| | | |
|---|---|---|
| GB | 2443208 A | 4/2008 |
| KR | 1020070027506 A | 3/2007 |
| WO | WO97/004820 A2 | 2/1997 |
| WO | WO00/028334 A1 | 5/2000 |
| WO | WO01/032124 A1 | 5/2001 |
| WO | WO2006/103422 A1 | 10/2006 |
| WO | WO2007/033401 A1 | 3/2007 |
| WO | WO2008/003920 A1 | 1/2008 |
| WO | WO2009/104127 A1 | 8/2009 |
| WO | WO2010/085111 A2 | 7/2010 |
| WO | WO2017/027145 A1 | 2/2017 |
| WO | WO2019/084448 A1 | 5/2019 |

OTHER PUBLICATIONS

Partsch; "The static stiffness index: a simple method to assess the elastic property of compression material in vivo"; Dermatologic Surgery; vol. 31(6); pp. 625-630; Jun. 2005.

Partsch et al.; "Measurement of lower leg compression in vivo: recommendations for the performance of measurements of interface pressure and stiffness"; Dermatologic Surgery; vol. 32(2); pp. 224-233; Feb. 2006.

Partsch et al.; "Interface pressure and stiffness of ready made compression stockings: Comparison of in vivo and in vitro measurements"; Journal of Vascular Surgery; vol. 44(4); pp. 809-814; Oct. 2006.

Allan et al; "The use of graduated compression stockings in the prevention of postoperative deep vein thrombosis"; Br. J. Surg.; vol. 70(3); pp. 172-174; Mar. 1983.

Badr et al.; "Differences in local environment determine the site of physiological angiogenesis in rat skeletal muscle"; Experimental Physiology; vol. 88(5); pp. 565-568; Sep. 2003.

Butson; "Intermittent pneumatic calf compression for prevention of deep venous thrombosis in general abdominal surgery"; Am J Surg; vol. 142(4); pp. 525-527; Oct. 1981.

Byl et al.; "Low-dose ultrasound effects on wound healing: a controlled study with Yucatan pigs"; Arch Phys Med Rehabil.; vol. 73(7); pp. 656-664; Jul. 1992.

Clagett et al.; "Prevention of venous thromboembolism in general surgical patients"; Ann Surg; vol. 208(2); pp. 227-240; Aug. 1988.

Comerota et al.; "The fibrinolytic effects of intermittent pneumatic compression: mechanism of enhanced fibrinolysis"; Ann Surg; vol. 226(3); pp. 306-314; Sep. 1997.

Dawson et al.; "A comparison of the microcirculation in rat fast glycolytic and slow oxidative muscles at rest and during contractions"; Microvascular Research; vol. 33(2); pp. 167-182; Mar. 1987.

Deveci et al.; "Relationship between capillary angiogenesis, fiber type, and fiber size in chronic systemic hypoxia"; Am. J. Physiol. Heart Circ. Physiol; vol. 281(1); pp. H241-H252; Jul. 2001.

Dyson et al.; "Induction of mast cell degranulation in skin by ultrasound"; IEEE Transactions on Ultrasonics, Fenoelectrics, and Frequency Control; vol. 33(2); pp. 194-201; Feb. 1986.

Dyson et al.; "Stimulation of tissue repair by ultrasound: a survey of the mechanisms involved"; Physiotherapy; vol. 64(4); pp. 105-108; Apr. 1978.

Egginton et al.; "Capillary growth in relation to blood flow and performance in overloaded rat skeletal muscle"; J. Appl. Physiol; vol. 85(6); pp. 2025-2032; Dec. 1998.

Heit; "Venous thromboembolism epidemiology: implications for prevention and management"; Seminars in Thrombosis and Hemostasis; vol. 28, Supp 2; pp. 3-13; Jun. 2002.

Hills et al.; "Prevention of deep vein thrombosis by intermittent pneumatic compression of calf"; British Medical Journal; vol. 1(5793); pp. 131-135; Jan. 1972.

Hudicka et al.; "Is physiological angiogenesis in skeletal muscle regulated by changes in microcirculation?"; Microcirculation; vol. 5(1); pp. 5, 7-23; Feb. 1998.

Hudicka et al.; "Early changes in fiber profile and capillary density in long-term stimulated muscles"; Am J Physiol; vol. 243(4); pp. H528-H535; Oct. 1982.

(56) References Cited

OTHER PUBLICATIONS

Milkiewicz et al.; "Association between shear stress, angiogenesis, and VEGF in skeletal muscles in vivo"; Microcirculation; vol. 8(4); pp. 229-241; Aug. 2001.

Husmann; "The treatment of peripheral arterial disease with mechanical compression and angioplasty with focus on vascular dysfunction"; https://www.researchgate.net/publication/281726960; pp. 1-6; Jan. 2010.

Delis et al.; "Effects of intermittent pneumatic compression of the calf and thigh on arterial calf inflow: a study of normals, claudicants, and grafted arteriopaths"; Surgery; vol. 129(2); pp. 188-195; Feb. 2001.

Delis et al.; "Haemodynamic effect of intermittent pneumatic compression of the leg after infrainguinal arterial bypass grafting"; British Journal of Surgery; vol. 91(4); (Manuscript copy, 9 pages); Apr. 2004.

Husmann et al.; "Integrity of venoarteriolar reflex determines level of microvascular skin flow enhancement with intermittent pneumatic compression"; Journal of Vascular Surgery; vol. 48(6); pp. 1509-1513; Dec. 2008.

Husmann et al.; "Long-term effects of endovascular angioplasty on orthostatic vasocutaneous autoregulation in patients with peripheral atherosclerosis"; Journal of Vascular Surgery; vol. 44(5); pp. 993-997; Nov. 2006.

Husmann et al.; "Successful lower extremity angioplasty improves brachial artery flow-mediated dilation in patients with peripheral arterial disease"; Journal for Vascular Surgery; vol. 48(5); pp. 1211-1216; Nov. 2008.

Redolfi et al.; "Attenuation of obstructive sleep apnea by compression stockings in subjects with venous insufficiency"; Am J Respir Crit Care Med; vol. 184(9); pp. 1062-1066; Nov. 2011.

Higashi el al.; New methods to evaluate endothelial function: method for assessing endothelial function in humans using a strain-gauge plethysmography: nitric oxide-dependent and-independent vasodilation; Journal of pharmacological sciences; 93(4):pp. 399-404; Sep. 1, 2003.

Tschakovsky et al.; Beat-by-beat forearm blood flow with Doppler ultrasound and strain-gauge plethysmography; Journal of Applied Physiology, 79(3); pp. 713-719; Sep. 1995.

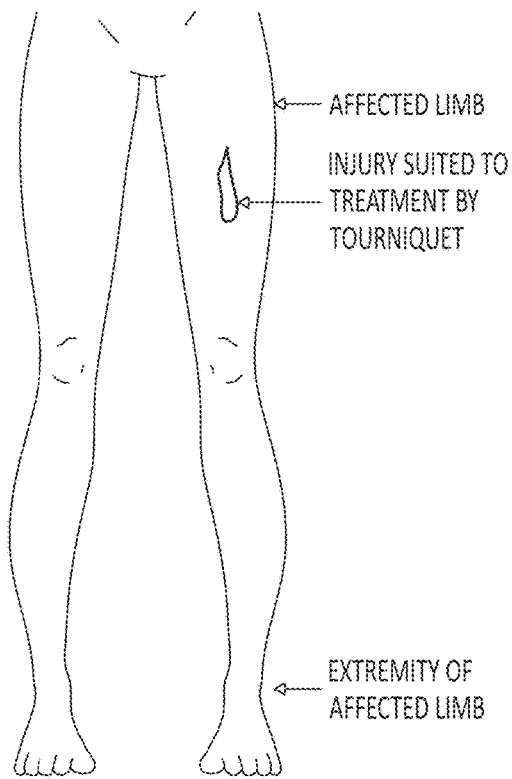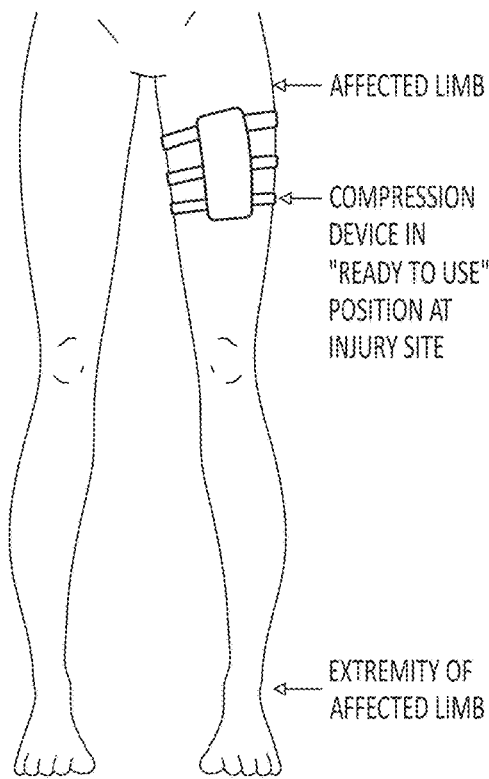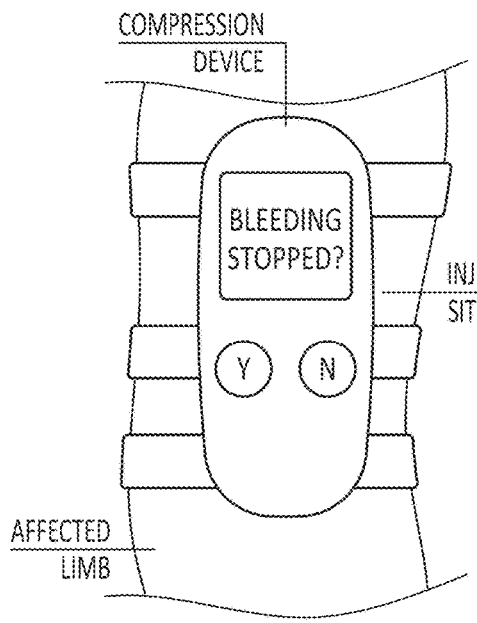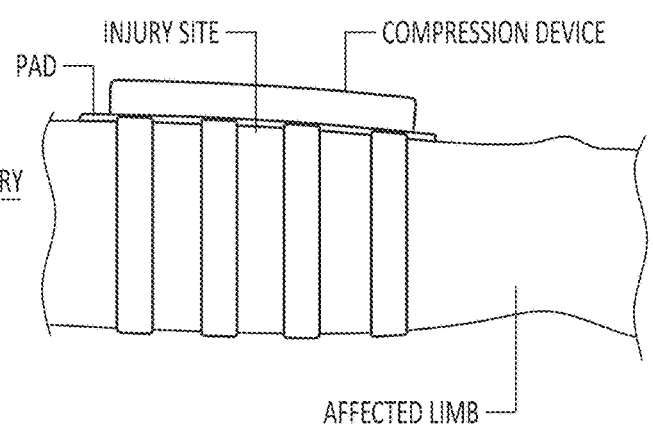
FIG. 21
FIG. 22
FIG. 23
FIG. 24

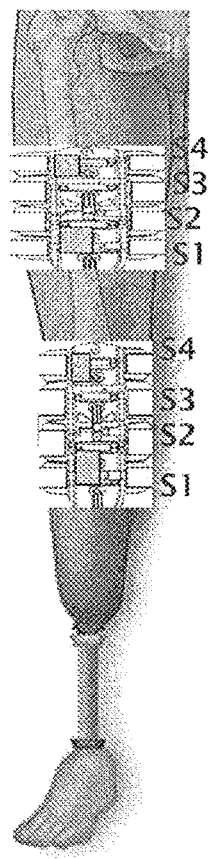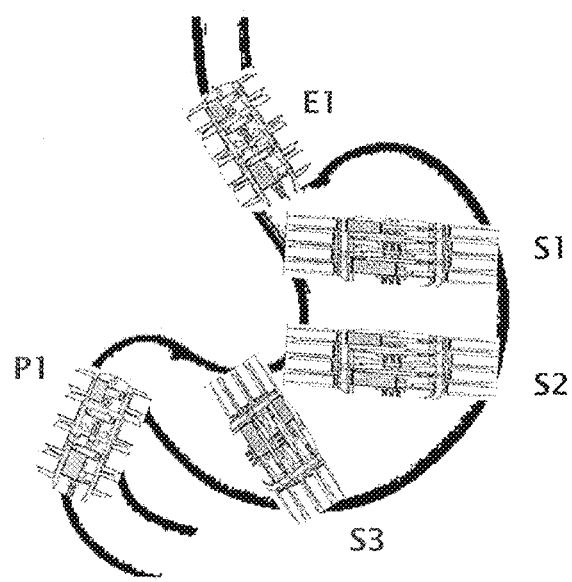
FIG. 30
FIG. 34

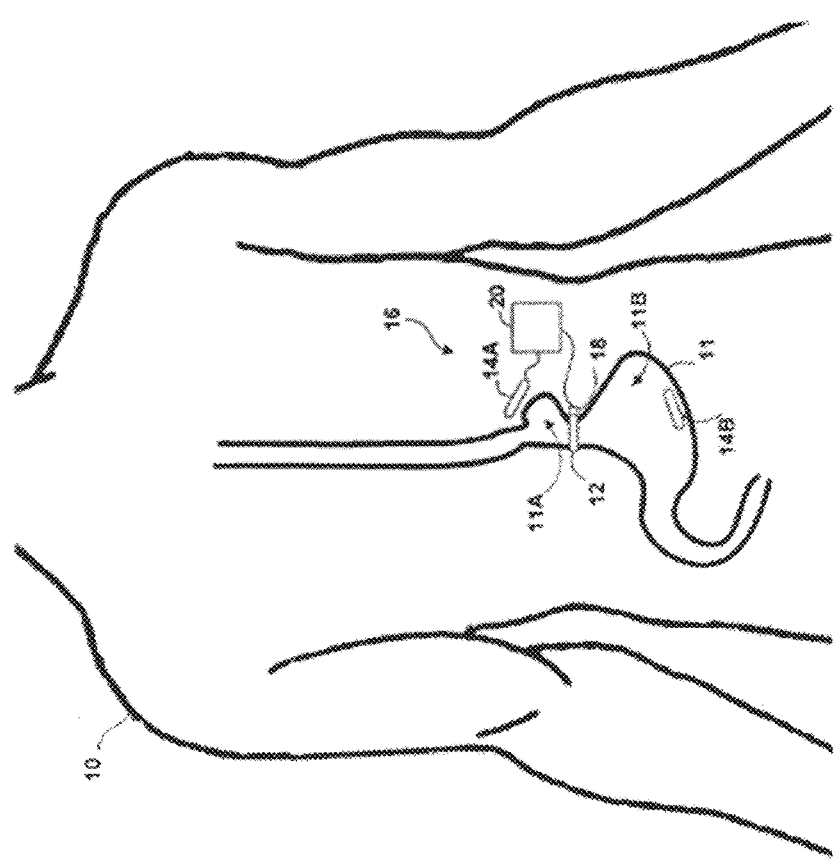

ADAPTIVE COMPRESSION THERAPY SYSTEMS AND METHODS

CROSS REFERENCE TO RELATED APPLICATIONS

This application is a continuation of U.S. patent application Ser. No. 15/499,850, filed Apr. 27, 2017, titled "ADAPTIVE COMPRESSION THERAPY SYSTEMS AND METHODS," now U.S. Pat. No. 10,076,462, which claims priority to U.S. Provisional Patent Application No. 62/328,574 filed Apr. 27, 2016 and titled "ADAPTIVE COMPRESSION THERAPY SYSTEM," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

Embodiments of the invention relate generally to systems and methods to provide compression therapy to a body part, and more specifically, to systems and methods to provide active and/or adaptive compression therapy to a body part.

BACKGROUND

Compression therapy (CT), is the selective external compression of a portion of the body using wraps, stockings, inflatable cuffs and bandages. CT can be either passive compression using elastic or inelastic bandages or multiple layers of bandages (no external energy applied) or active, where an external energy source augments a compressive force applied to body part(s), as shown in FIGS. 1A-E. CT is used to treat many conditions including: vascular insufficiency (both arterial and venous) as shown in FIG. 2, lymphedema, post thrombotic syndrome, DVT prophylaxis, post op pain/swelling, leg swelling, varicose veins, enhance blood circulation, intermittent claudication, inoperative peripheral arterial disease, post-operative swelling, congestive heart failure, sport/exercise recovery, and massage.

Examples of the some of the commercially available compression bandages currently available include those made by 3M, BSN Medical, Convatec, Derma Sciences, Hartman group, Kendell/Covidien, Lohmann and Rauscher, Medline Industries, and Smith and Nephew. The compressive force of compression bandages is achieved in the application or wrapping of the bandage by a caregiver. The consistency of the compression is dependent on the skill of the caregiver applying the bandage. There is no feedback on the amount of compressive force applied with bandages. The patient is wears the bandage until the stocking loses its compliance or become soiled. Bandages are typically applied to the arms or legs.

Compression stockings (CS) are elastic stockings that are typically placed over the lower leg like long length sock or leg hosiery. The stockings are marketed to provide a specific level of compression, often greater compression at the ankle with reducing levels of compression toward the knee to compensate for the higher hydrostatic pressure toward the ankle when standing.

CS can be designed to provide a range of pressures to the lower leg. For example, a CS that delivers light compression can provide less than 20 mmHg of pressure; moderate compression is between 20 to 40 mmHg, strong compression between 40 and 60 mmHg and very strong compression can be over 60 mmHg.

Manfacturers offer a variety of compression levels up to 60 mmHg. Some manufacturers of CS include Bauerfeind, BSN, Kendell/Covidien, and Sigvaris.

Active compression (AC), often referred to as pneumatic compression devices use air chamber containing sleeves that enclose the patient's leg or foot. The three main categories of AC are foot pumps, that compress the venous sinus of the foot, intermittent pneumatic compression (IPC) that inflate and deflate the entire sleeve at the same time and sequential compression pumps (SC) that sequentially inflate chambers in the sleeve to move the blood (or milk) the blood toward the foot to enhance arterial flow, or toward the waist to improve venous, lymphatic fluid or enhance removal of lactic acid post-exercise.

AC devices are made in both plug-in and battery-powered mobile units as shown in FIG. 2. With the exception of the Venowave, which uses a roller to roll the calf, the pneumatic compression devices typically operate in the same manor. A pneumatic pump fills a bladder or series of airtight bladders that is controlled via a console.

There is strong evidence that all these forms of compression therapy are helpful in treating or preventing the conditions for which they are used. The significant deficiencies that all of these technologies suffer from is unknown/inconsistent pressure application, poor comfort due to bulky, non-breathable cuffs and difficulty in donning/doffing the stockings or wraps. These design deficiencies result in non-compliance with the technologies, estimated to be as high as 70%. The root cause for poor compliance with compression therapy is multi-factorial. Standard tight fit stockings are hard to don/doff for someone who already has limited mobility due to their disease. Some clinicians resort to recommending that patients apply KY jelly over the leg to help don/doff the stocking, as well as using an external donning/doffing aid, such as a Jobst Stocking Donner (Model number 110913). In addition, although these stocking can be provided in multiple sizes, to the stockings often have problems with poor fit, including areas that are too tight causing pain or too loose causing the stocking to droop. Inelastic compression wraps (e.g. Unna boot) where the lower leg is wrapped in a series of layers of cotton wraps with zinc oxide and other compounds, are not well tolerated by patients either as they are rigid, uncomfortable, can develop a foul smell due to accumulation of exudates from the ulcer and must be changed weekly. Inelastic compression wraps have an additional burden as compression wraps must be changed often, which typically requires the patient to travel to a venous clinic and utilizes expensive nursing resources.

With millions of affected patients affected in the US and billions of dollars spent attempting to treat patients with poorly understood treatment regimens with devices that patients are reticent to use due to discomfort, there is clearly a need for a better technology. Therefore, there is a need for an innovative, multi-mode compression therapy system that addresses these problems.

SUMMARY OF THE DISCLOSURE

The present invention relates generally to systems and methods to provide compression therapy to a body part, and more specifically, to systems and methods to provide active and/or adaptive compression therapy to a body part.

In some embodiments, a device for providing compression therapy to a body part of a patient is provided. The device may include a drive unit configured to be placed over or against a body part. The drive unit can include one or more motors; a controller configured to control operation of the one or more motors; a power source in electrical communication with the one or more motors and the controller; and a plurality of pulleys; one or more drive elements configured to be tensioned by the one or more motors, wherein the one or more drive elements are threaded around the plurality of pulleys; and one or more compression mechanisms configured to be wrapped at least partially around a portion of the body part, wherein the one or more compression mechanisms are attached to the pulleys and are configured to be tensioned by the pulleys.

In some embodiments, the plurality of pulleys comprises a plurality of movable pulleys and a plurality of fixed pulleys, and the compression mechanisms are attached to the movable pulleys.

In some embodiments, the device further includes one or more physical stops that limit the movement of the movable pulleys and are configured to align the movable pulleys.

In some embodiments, the drive element is selected from a cord, belt, and chain.

In some embodiments, the drive unit comprises a base plate that is articulated and comprises a first plate portion and a second plate portion.

In some embodiments, the one or more motors comprises a first motor disposed on the first plate portion and a second motor disposed on the second plate portion, and wherein the plurality of pulleys comprises a first set of fixed pulleys attached to the first plate portion and a second set of fixed pulleys attached to the second plate portion.

In some embodiments, the drive unit comprises a base plate and the fixed pulleys are disposed within one or more channels within the base plate.

In some embodiments, the movable pulleys are disposed within one or more channels in the base plate.

In some embodiments, the movable pulleys and the fixed pulleys are arranged within the one or more channels such that one or more drive cords extending between the movable pulleys and the fixed pulleys are aligned with a direction of travel of the movable pulleys within the one or more channels.

In some embodiments, the device further includes one or more sensors in communication with the controller, where the one or more sensors are configured to measure data related to the compression therapy provided to the patient and/or data related to the status of the patient.

In some embodiments, the one or more sensor includes a sensor configured to measure a magnitude of pressure applied to the body part by the device.

In some embodiments, the one or more sensors comprises a sensor configured to measure a girth or a volume of the body part.

In some embodiments, the device further includes a wireless communication module in communication with the controller.

In some embodiments, the one or more compression mechanisms are integrated into a garment or shoe.

In some embodiments, the drive unit is integrated into the garment or shoe.

In some embodiments, a method for compressing a body part of a patient is provided. The method includes fastening one or more compression elements of a wearable compression device around the body part. The wearable compression device may include a compression plate, one or more motors disposed on the compression plate and configured to tighten or loosen the one or more compression elements fastened around the body part, one or more sensors configured to measure physiological data and/or device performance data, and a controller for controlling the one or more motors according to a set of parameters. The method further includes adjusting a tension of the one or more compression elements until the one or more sensors measures a predetermined or set parameter before initiating compression therapy; initiating a first compression cycle comprising compressing the body part by using the one or more motors to tighten the one or more compression elements, and uncompres sing the body part by using the one or more motors to loosen the one or more compression elements; waiting at least a predetermined or set amount of time before initiating a second compression cycle; measuring physiological data and/or device performance data using the one or more sensors; and modulating the treatment parameters based on the measured physiological data and/or device performance data.

In some embodiments, the predetermined or set parameter is an interface pressure between the compression device and the body part.

In some embodiments, the measured physiological data comprises a measurement of the girth of the body part or a volume of the body part.

In some embodiments, the method further includes delivering passive compression therapy by adjusting the pressure of the one or more compression elements to a predetermined level and maintaining the tension of the one or more compression elements at the predetermined level for an extended period of time that is at least about 1 minute to 24 hours.

In some embodiments, the method further includes wirelessly transmitting the measured physiological data and/or device performance data to a remote device.

In some embodiments, the method further includes establishing communications between the wearable compression device and a second wearable compression device; and coordinating delivery of compression therapy between the wearable compression device and the second wearable compression device.

In some embodiments, the one or more compression elements comprises at least two compression elements that are tightened sequentially.

In some embodiments, a device for compressing a body part is provided. The device may include a compression transmission mechanism having a first end portion and a second end portion, the compression transmission mechanism configured to be wrapped around at least a portion of the body part; a tightening mechanism configured to tighten and/or loosen the compression transmission mechanism; a first mechanical stop configured to provide a starting location for the first end portion of the compression transmission mechanism; a second mechanical stop configured to provide a starting location for the second end portion of the compression transmission mechanism; a sensor configured to measure a strain, force, or pressure applied to the body part by the system; a motor configured to tighten and/or loosen the compression transmission mechanism by simultaneously moving both the first end portion and the second end portion of the compression transmission mechanism; and a controller configured to provide an indicator when the sensor measures a set or predetermined strain, force, or pressure;

and initiate compression treatment by actuating the motor after the strain gauge measures the set or predetermined strain, force, or pressure.

In some embodiments, the compression transmission mechanism comprises one or more compression straps.

In some embodiments, the compression transmission mechanism further comprises one or more pads for distributing pressure generated by the one or more compression straps.

In some embodiments, the compression transmission mechanism comprises one or more laces configured to be tightened by a reel based tensioning mechanism.

In some embodiments, a system for delivering compression therapy is provided. The system can include a first compression device comprising a compression plate, one or more motors disposed on the compression plate and configured to tighten or loosen one or more compression elements configured to be fastened around a first body part, one or more sensors configured to measure physiological data and/or device performance data, a communications module, and a controller for controlling the one or more motors according to a set of parameters; and a second compression device including a compression plate, one or more motors disposed on the compression plate and configured to tighten or loosen one or more compression elements configured to be fastened around a second body part, one or more sensors configured to measure physiological data and/or device performance data, a communications module, and a controller for controlling the one or more motors according to a set of parameters; wherein the first compression device and the second compression device are configured to communicate with each other and coordinate delivery of compression therapy.

In some embodiments, the first compression device includes a pulley based drive train that is driven by the one or more motors and configured to tighten or loosen the one or more compression elements.

In some embodiments, the pulley based drive train comprises a plurality of movable pulleys.

In some embodiments, the pulley based drive train further includes one or more physical stops that limit the movement of the movable pulleys and are configured to align the movable pulleys.

In some embodiments, a system for providing compression treatment to a subject is provided. The system may include a wearable compression device configured to provide compression to a body part of the subject, the wearable compression device comprising a compression plate, one or more motors disposed on the compression plate, one or more compression mechanisms configured to be wrapped around the body part and tightened or loosened by the one or more motors, one or more sensors configured to measure physiological data and/or device performance data, a controller for controlling the one or more motors according to a set of parameters, and a wireless communications module in communication with the controller and the one or more sensors; and a remote device configured to wirelessly communicate with the wireless communications module of the wearable compression device and to receive the measured physiological data and/or device performance data and to modulate the set of parameters for controlling the one or more motors.

In some embodiments, the system further includes a server or cloud computing network in communication with the remote device, the server or cloud computing network comprising a database that includes population health data and personal health data, wherein the population health data comprises data from a population of subjects that used or are using compression treatment, wherein the personal health data comprises the subject's medical data, the subject's physiological data, and the device performance data, wherein the remote device, server or cloud computing network is configured to modulate the set of parameters for controlling the one or more motors based on the population health data and the personal health data.

In some embodiments, the remote device is selected from the group consisting of a smart phone, a smart watch, a tablet computer, a laptop computer, server, computing device, and a desktop computer.

In some embodiments, the remote device is programmed to wirelessly operate the wearable compression device.

In some embodiments, the remote device is programmed to wirelessly operate the wearable compressive device, alternating between an active compression mode and a passive compression mode.

In some embodiments, the remote device is programmed to wirelessly operate the wearable compression device according to one or more treatment protocols.

In some embodiments, the treatment protocols are predetermined.

In some embodiments, the treatment protocols are customizable by the subject and/or a healthcare provider.

In some embodiments, the controller and/or the remote device is programmed to modify one or more of the treatment protocols based on the measured physiological data and/or the device performance data.

In some embodiments, the controller and/or the remote device is programmed to select one of the treatment protocols based on the measured physiological data and/or the device performance data.

In some embodiments, the remote device is programmed to display the measured physiological data and/or the device performance data.

In some embodiments, the remote device is programmed to monitor subject compliance and display subject compliance data.

In some embodiments, the one or more sensors are selected from the group consisting of a strain gauge, a pressure sensor, a force sensor, a heart rate sensor, GPS device, a blood pressure sensor, microphone, Hall effect sensor, sweat biochemistry sensor, light sensor, an impedance sensor, a blood clot detection sensor, a blood flow sensor, an ultrasound sensor, a temperature sensor, a gas sensor, a blood chemistry sensor, a physical activity sensor, oxygen sensor, EKG sensor, gyroscope, and an accelerometer.

In some embodiments, the measured physiological data includes plethysmography data.

In some embodiments, the controller and/or the remote device is programmed to determine a disease state and/or treatment efficacy based in part from the plethysmography data.

In some embodiments, the controller and/or the remote device is programmed to modify one or more of the treatment protocols based on the plethysmography data.

In some embodiments, the remote device is programmed to prompt the subject for treatment related data.

In some embodiments, the remote device is programmed to send the subject reminders regarding the compression treatment and/or compliance with the compression treatment.

In some embodiments, the remote device is programmed to send updates regarding the compression treatment and/or the subject to healthcare providers, family members, and/or other authorized individuals.

In some embodiments, the remote device is configured to upload the measured physiological data and/or device performance data to the server or cloud computing network.

In some embodiments, a system for providing compression treatment to a subject is provided. The system may include a wearable compression device configured to provide compression to a body part of the subject according to a set of treatment parameters, the wearable compression device including a plurality of sensors configured to measure a level of compression applied to the body part and to measure physiological data and/or device performance data, memory to record the level of compression applied to the body part, a controller for controlling the compression delivered by the wearable compression device, and a wireless communications module in communication with the controller; a remote device configured to wirelessly communicate with the wireless communications module of the wearable compression device and to receive the measured physiological data and/or device performance data and to modulate the set of treatment parameters for controlling the wearable compression device; and a server or cloud computing network in communication with the remote device, the server or cloud computing network including a database that includes population health data, and personal health data, wherein the population health data comprises data from a population of subjects that used or are using compression treatment, wherein the personal health data includes the subject's medical data, the subject's physiological data, and the device performance data, wherein the remote device, server or cloud computing network is configured to modulate the set of parameters for controlling the compression device based on the population health data and the personal health data.

In some embodiments, the plurality sensors are configured to measure physiological data selected from the group consisting of the subject's body part girth, body part volume, posture, physical activity level, venous filling time, venous reflux, venous index, ulcer status, heart rate, oxygen level, temperature, blood pressure, sweat biochemistry, impedance, temperature, oxygen level, electrical activity, and blood flow dynamics.

In some embodiments, the set of treatment parameters for controlling the compression device includes compression level, compression duration, compression frequency, and compression speed.

In some embodiments, the compression device further includes a pulley based drivetrain that is driven by one or more motors.

In some embodiments, the set of parameters for controlling the compression device are modified based on artificial intelligence or machine learning algorithms.

In some embodiments, the remote device, server, or cloud computing network is programmed to monitor the subject's compliance with the compression treatment.

In some embodiments, the remote device, server, or cloud computing network is programmed to send reminders to the subject to initiate compression treatment.

In some embodiments, the remote device, server, or cloud computing network is configured to generate status updates regarding the subject's compression treatment that can be viewed by the subject and other authorized individuals.

In some embodiments, a device for delivering compression therapy to a subject is provided. The device may include a wearable compression mechanism configured to compress a body part of the subject; one or more sensors configured to measure physiological data of the subject and/or performance data of the wearable compression mechanism; and a controller configured to control the wearable compression mechanism based on a set of compression parameters; and modulate the set of compression parameters using machine learning and/or artificial intelligence algorithms based on the measured physiological data and/or performance data.

In some embodiments, a device for delivering compression therapy to a subject is provided. The device may include a wearable compression mechanism configured to compress a body part of the subject; a sensor configured to measure an interface pressure between the wearable compression mechanism and the body part; and a controller configured to control the wearable compression mechanism based on a set of compression parameters; and initiate compression of the body part and/or modulate the set of compression parameters based on the measured interface pressure.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 21 is a top down view of the legs of a subject having an injury in the thigh of the subject's left leg suited for treatment by use of a tourniquet.

FIG. 22 is a front view of the subject in FIG. 21 with a compression device positioned over and in position relative to the injury site to provide a tourniquet functionality.

FIG. 23 is an enlarged view of the compression device of FIG. 22 showing a display and function keys for operation of the compression device to apply pressure to the affected limb to stop bleeding.

FIG. 24 is a side view of an affected limb with a compression device in position at the injury site and working in conjunction with a patch.

FIG. 30 is a front view of a subject with an amputated portion of the right leg as in FIG. 29.

FIG. 33 is diagram illustrating a view of a torso of a patient, in which stomach is visible.

FIG. 34 is a cross section of the lower esophagus, stomach and duodenum of a subject with a plurality of compression devices adapted for implantation and configured for constriction or manipulation of the gut.

DETAILED DESCRIPTION

Described herein are systems, devices, and methods that make compression therapy comfortable, consistent, easy to use, and customized to increase compliance with a proven therapy. In addition, the use of an effective, low profile, mechanical drive system in combination with modern sensing, data management and remote interface enables the system to add functionality that will improve outcomes. The basis of the system is the mechanical tensioning and coordination of therapy among multiple compression bands around a part of the body. The system is further enabled by sensors, mechanical feedback, and user input that enable real-time monitoring, adjustments and adaptation to the individual patients' anatomy, physiology, tolerance, and therapeutic needs. Finally, the unique data steams form this device including mechanical, physiological, imaging, and patient feedback data can be leveraged on both an individual and population basis with analytics and artificial intelligence in order to optimize therapy for both individuals and populations.

Described herein are systems, devices, and methods that enable both standard compression and active therapy in a mobile, lightweight, breathable, simple interface that encourages compliance with remote monitoring capability. Additional features of strain gauge plethysmography, tilt sensing, compliance and remote monitoring are included to facilitate better outcomes through accumulation of a large database of treatment outcomes. Various embodiments include a "smart" stocking that can use real time data and proprietary algorithms in order to implement customized treatment that learns and adapts to the specific patient needs and disease state progression.

Figure 1A:
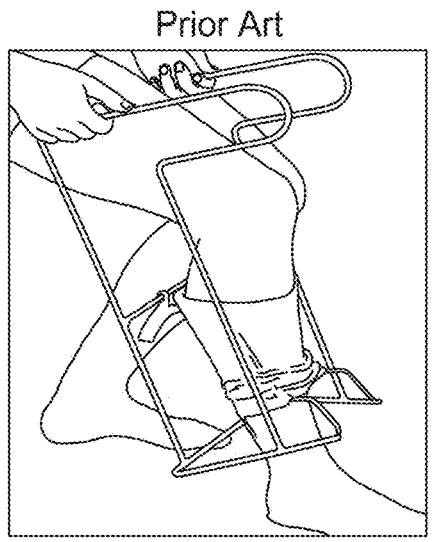
FIGS. 1A-1E illustrate various passive and active compression therapy devices.
Figure 1B:
Figure 1C:
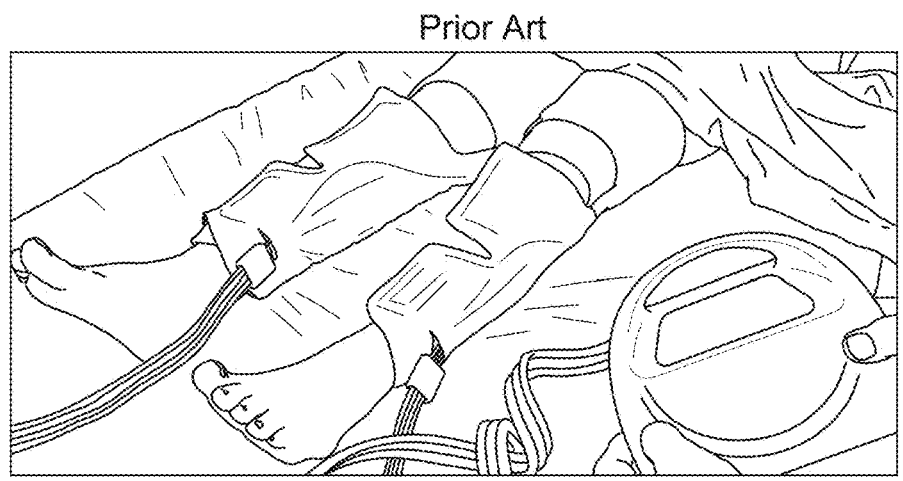
Figure 1D:
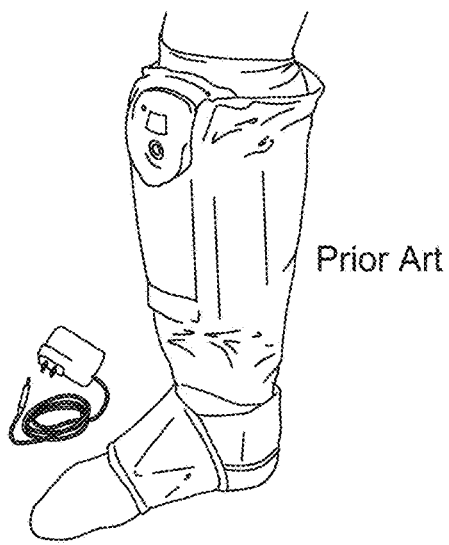
Figure 1E:
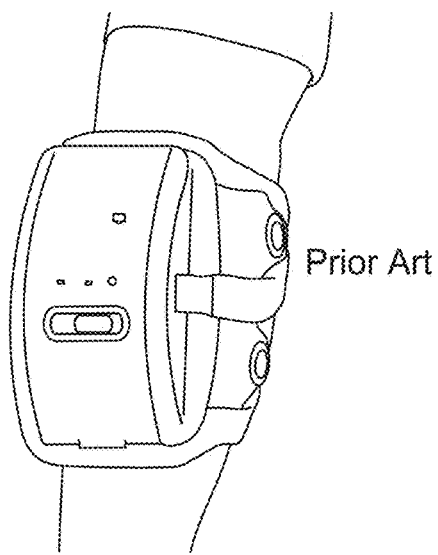
Figure 2:
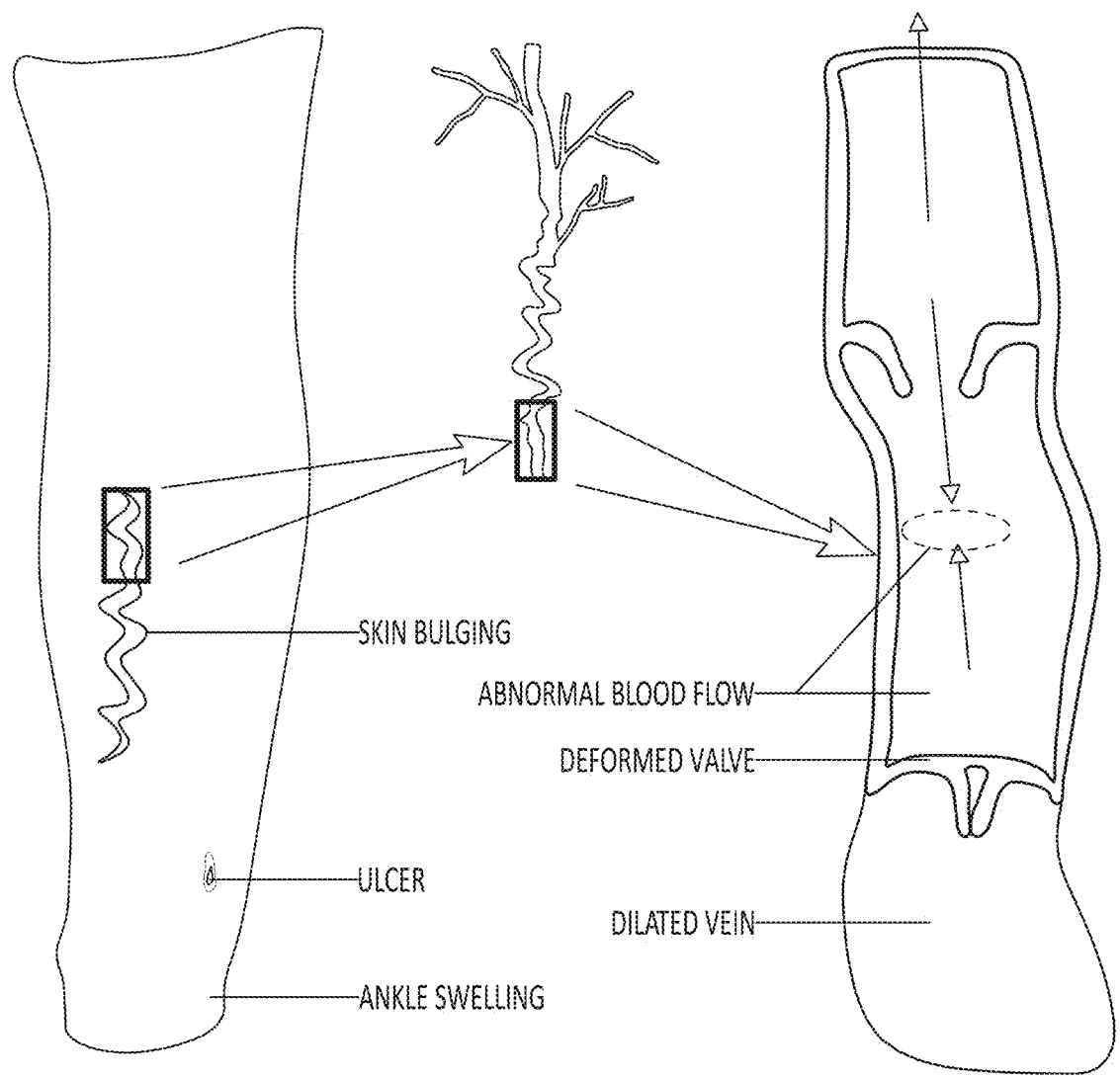
FIG. 2 illustrates vascular insufficiency caused by deformed or defective valves in a blood vessel, such as a vein.
Figure 3A:
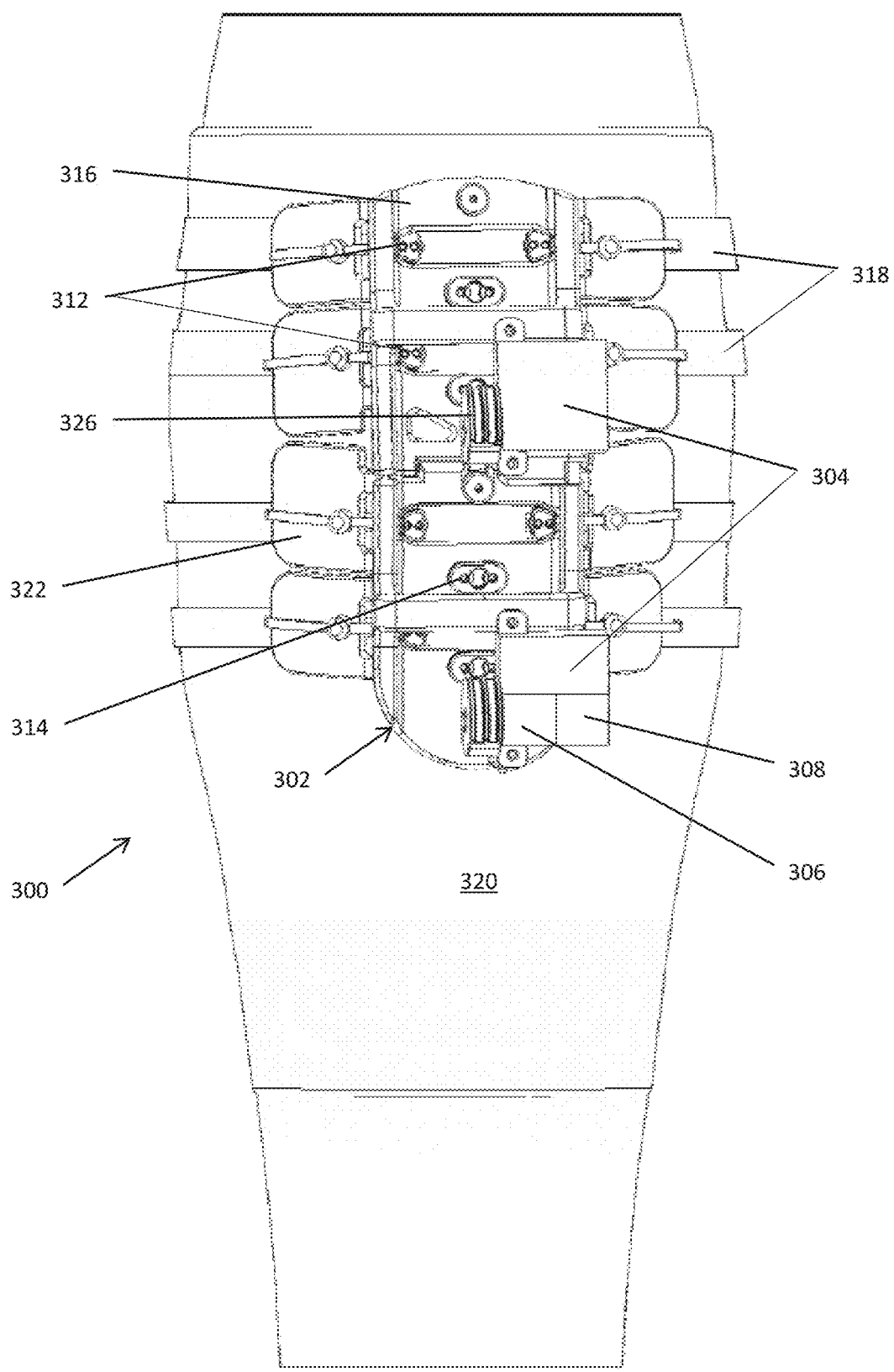
FIGS. 3A-3C illustrate an embodiment of a compression device.
Figure 3B:
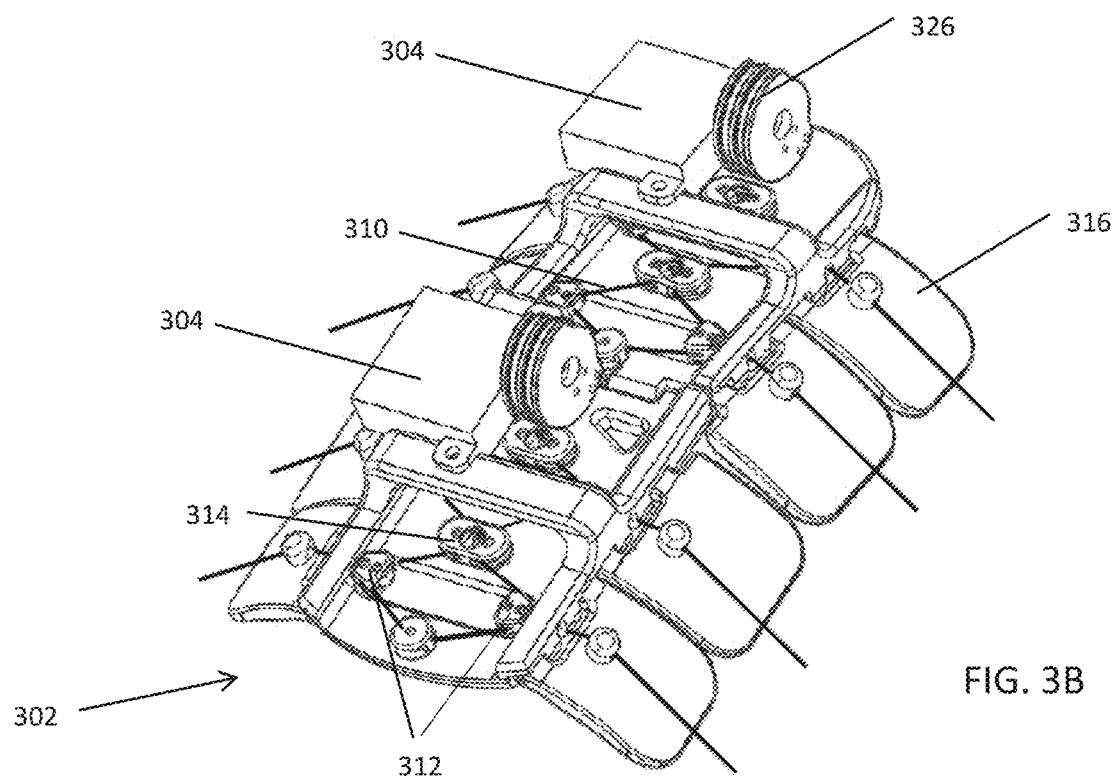
Figure 3C:
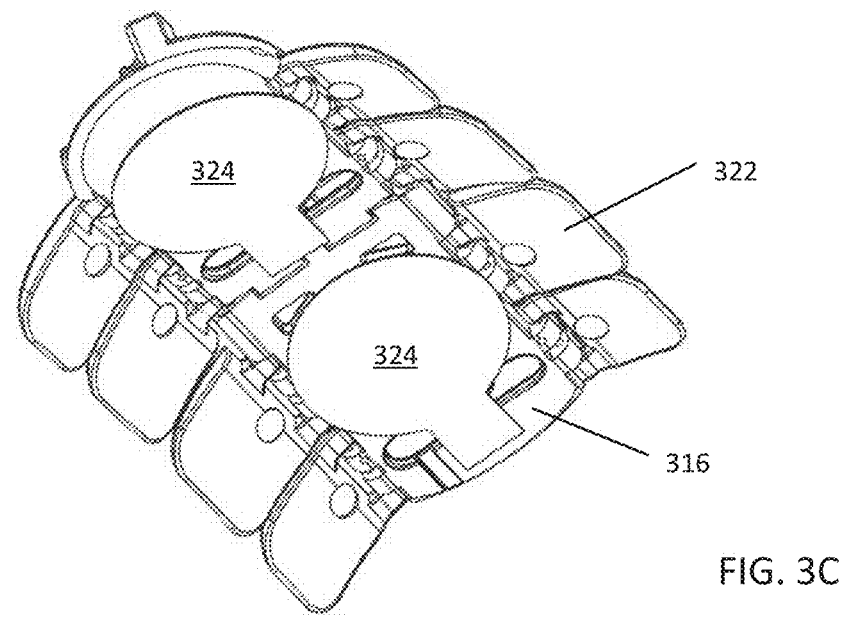

In some embodiments, as shown in FIGS. 3A-3C the basic components of the compression systems 300 include a compression device 302 that includes one or more geared motor(s) 304, a power source (e.g., a battery) 306, an electronic control board 308 with processor(s) and memory, wireless capability, a force transmission drivetrain that may be pulley based and include a drive cord 310 and both movable pulleys 312 and fixed pulleys 314 that are fixed on a compression plate 316, compression transmission components 318, a calf understocking 320, padding 322, an attachment mechanism, an ankle compressive understocking, a remote control system, and various sensors 324 and diagnostic components such as a pressure sensor and accelerometer, for example. The motor(s) 304 rotate a drive pulley 326 on which the drive cord 310 is attached.

Alternative drive drains that may be pulley-less include using twisted pairs of drive cords that are attached on one end to the compression strap or mechanism, as described in U.S. Patent Publication No. 2008/0066574, for example. The other end of the twisted pair actuator can be attached to a motor that can twist the pair of drive cords to shorten the twisted pair and generate force and compression, and the motor can untwist the twisted pair to lengthen the twisted pair to reduce the force and compression. Yet another pulley-less drive train can include directly attaching the drive cord to the compression strap or mechanism and omitting the pulleys.

For example, the system can include the parts and features listed below in Table 1.

TABLE 1

| Component | Purpose/Function |
| --- | --- |
| Compression Plate | Delivers compression to select zone under plate |
| Electronic control system | Controls motor position, rotation, speed, wireless communication, data acquisition and storage |
| Battery/Energy source | Provide power for motor and electronics. Could be rechargeable battery, kinetic system, inductive charging, charged from heating of leg, |
| Motor | Brushed or brushless servomotor. Lead screw motor, solenoid, |
| Drive Shaft | Circular or cam shape to spool drive cord. |
| Compression straps | Straps or integrated inelastic cords woven into elastic stocking. |
| Compression wings | Flexible, adaptable elements to transmit force to leg. Could be actively powered compressive elements. |
| Compression strap pulley | Moveable pulley. Translate force from motor to hoop of compression strap system |
| Compression plate pulley | Fixed pulley on compression plate. |
| Gauges | Integrated into compression plate chassis. Strain, accelerometer, temperature, light, gas, |
| Stocking | Woven, knit, electrospun or laminate stocking to cover appendage, provide indexed attachment for active system. Stocking could also have tension elements interwoven, attached with passive system to maintain constant tension. Anti-microbial (eg merino wool, silver fibers). Breathable, washable, disposable. |
| Padding, attachment mechanism | Clamshell, over the foot, circular or linear ratchet, Boa, |

In summary, a motor turns a drive shaft with a drive pulley. The drive pulley spools a drive cord threaded through a pulley based drivetrain, which includes both compression plate pulleys that are fixed on a compression plate and movable compression strap pulleys that transmit force from the motor to a compression strap system. Tension is applied to the compression straps as the drive pulley spools the drive cord, and tension is released by reversing the motor and the rotation of the drive shaft and the attached drive pulley, thereby allowing the drive cord to unspool. In addition, the compressed leg or other body part naturally provides a reactive force that promotes unspooling and unloading.

Figure 4:
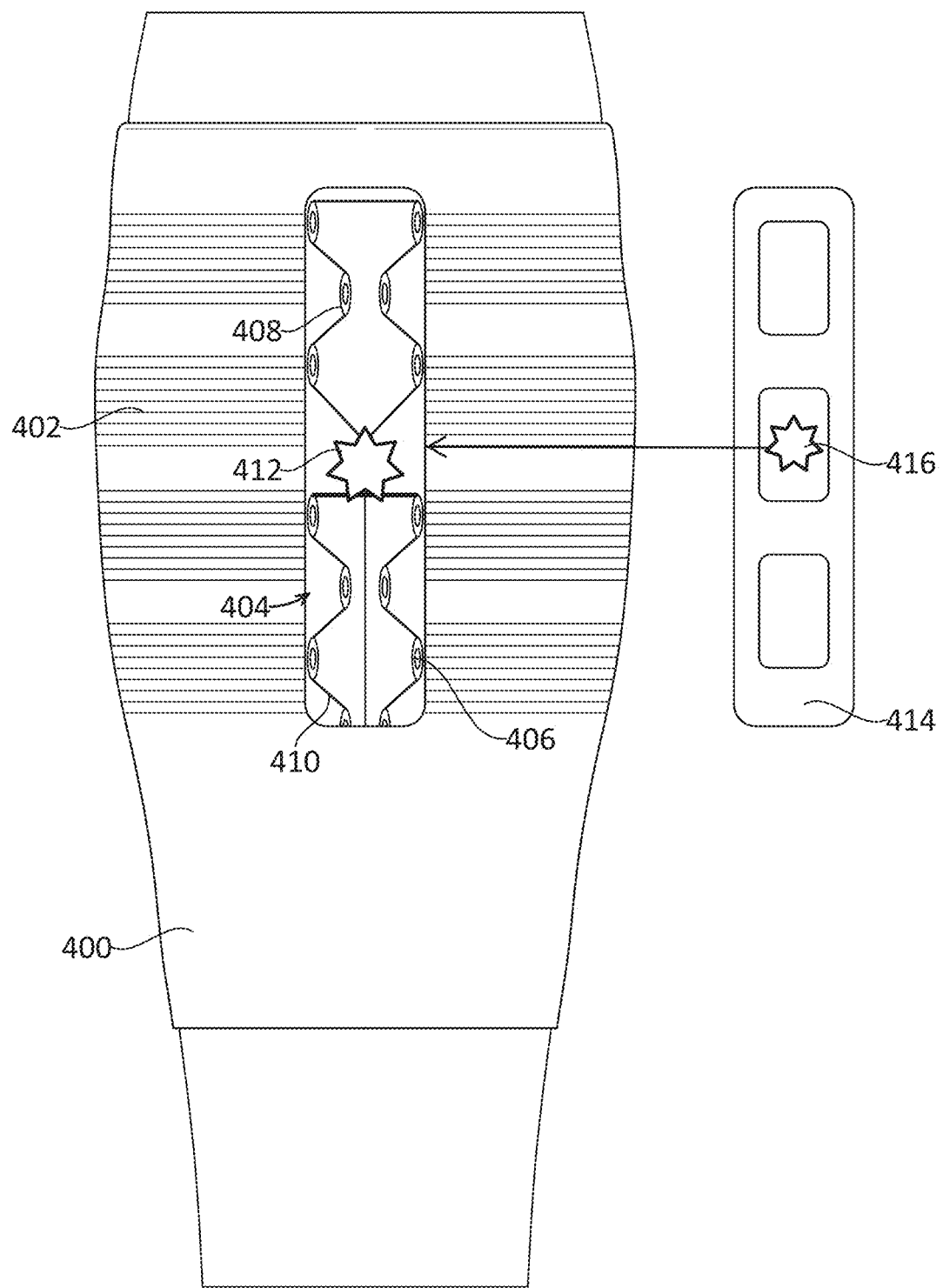
FIG. 4 illustrates an embodiment of a compression stocking with integrated compressive elements.

The system will now be described in more detail. As shown in FIG. 4, the understocking(s) 400, also referred herein as compression stockings or sleeves, are placed on desired appendage or body part, such as the arm, leg, foot, hand, toe, finger, or chest. The understockings 400 may have integrated active and/or passive compression/tensioning mechanism(s) 402, such as inelastic threads, wires, and/or cords that are woven into the stocking fabric or material, interwoven strain gauge or other gauges or sensors (e.g., temperature, O2, ultra sonography), integrated adjunctive therapy delivery (eg light, LEDs, drugs, sound waves, gas, electrical muscle stimulation, heating, cooling), and/or be constructed of antimicrobial materials (e.g., silver or superfine merino wool, etc.). The stocking can include a pulley based drive train 404 as described herein that may include movable pulleys 406 and fixed pulleys 408 and a drive cord 410 attached to a drive pulley 412. The drive pulley can have an interface that can be coupled to a drive unit 414 with a motor 416 having a complementary interface for coupling with the interface of the drive pulley 412. The drive unit can include electronics, the user interface, the battery, and other components that when combined with the stocking form a complete compression device. The understockings can be made of transparent or partially transparent materials to enable visibility to the treatment zone (e.g. wound areas) and/or light therapy to be administered in conjunction with compression therapy. The compression stocking can have prescribed or predetermined openings, zones, areas, or sections, such as one or more flaps, that can be removed, unzipped or otherwise opened to provide access underneath the stocking, such as for wound exposure prior to and/or while treatment is being provided for the wound and/or to provide access for a sensor to contact the patient's skin. The compression stocking can have one or more active/passive components to enhance breathability, such as including a fan, pores, and material design such as wicking materials. The stocking can include a negative pressure therapy component for wound healing that can be actively powered and/or monitored by the system. For example, the motor can drive a pump that generates negative pressure in a sealed wound dressing placed over the wound. The stocking construction design may provide active and/or passive compression without the addition of an additional optional active unit that would be included in a smart stocking to maintain/ monitor baseline pressure and compliance, as further described herein. The stocking, which may provide either active or passive compression, may collect data from integrated sensor(s) and change shape or configuration in response. The compression stocking can be made from materials incorporating one or more of the following: nonwovens, knits, wovens, extrusions, additive manufactured components, electronics, metallic, polymeric, natural materials. These materials (woven, knit, additive manufacturing) can be an integrated into a wearable component capable of providing compression therapy and other therapies. To increase the ease of putting the stockings on, a zipper, hook and/or loop or other adjunctive attachment mechanisms and methods may be used to place the stocking over the body part; for example, the stocking can be placed over the body in an open condition, and then the attachment mechanism closed or affixed to achieve a closed condition. In addition, multiple elastic understockings that can be easily put on may be overlapped in one or more area(s) to achieve a combined higher degree of compression in overlapped regions. Furthermore, placement of two or more compression therapy components, such as the stockings and other components of the system, can provide treatment either synergistically or independently. In some embodiments, the understockings can provide minimal compression, such as less than 15, 10, or 5 mmHg and can function primarily to assist in aligning and positioning the compression device onto the patient, as described below.

The compression plate/active compression assembly can be indexed, aligned and positioned properly on and around the stocking by aligning the compression plate/active compression assembly with index markers or patterns on the compression stocking and/or attachment to a compression stocking attachment that is integrated on the stocking. As shown in FIGS. 10B and 10C for example, indexing can utilize a visual, mechanical, magnetic, or electronic mechanism and/or method to attach the active components of the system to the passive compression stocking using a fastening mechanism such as hook & loop, plug, snap, magnet, strap, and/or slot. In some embodiments, the system provides active instructions and/or feedback regarding proper placement of the stocking on the body part and proper placement of the active control unit on the stocking. Sizing of the stocking can be determined by measurement of the length and circumference of the lower leg or body part to be compressed.

Figure 5A:
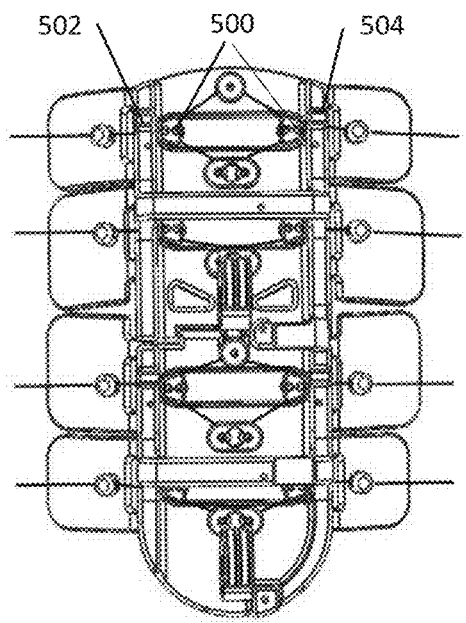
FIGS. 5A and 5B illustrate how physical stops can be used to align the movable pulleys in a pulley based drive train.
Figure 5B:
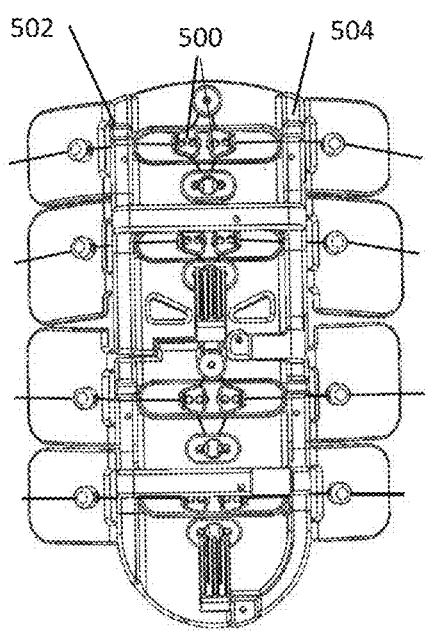

The active components of the system can index or zero itself to establish a reliable and consistent baseline configuration before initiating active compression therapy, as shown in FIG. 5A. This can be accomplished by seating or positioning the drive bearings 500, also referred to as the movable pulleys or the compression strap pulleys, in a "zero" position against hard stops 502, 504 along the outside edges of both sides of the compression plate at the start of a compression stroke cycle. Having stops on both sides of the compression plate prevents the movable pulleys 500 from becoming off-centered, which could result in undesired torque applied to the body part during the compression cycle. With the stops 502, 504, the movable pulleys 500 can be reliably positioned at the proper locations at the beginning of the compression cycle, allowing the system to provide a balanced, reliable and consistent amount of active compression to the body part, as shown in FIG. 5B. Zeroing the system to a baseline condition can be defined and/or controlled by mechanical means, features, or mechanisms, which may also provide a limit, which may be predetermined, to the travel of the movable pulleys along the compression plate. For example, the system can have mechanical hard-stops that limit the travel of the movable pulleys/compression strap pulleys along the compression plate and function to align the movable pulleys. If the stops are placed along the edges of the compression plate, the movable pulleys can travel to the edge of compression plate before the stop prevents further movement. This simple method/mechanism of zeroing the movable pulleys decouples the attachment method from the active compression method by setting the pulley travel position to a "zero" position regardless of the method used to affix the system to the body part. In some embodiments, no electronic charging or powering of the system is required to set system to zero point; the system may be mechanically adjusted by the user such that the movable pulleys are at the zero positions. In some embodiments, the act of putting on the device and fastening the device to the body part will automatically pull the movable pulleys against the stops and result in the movable pulleys being positioned at the zero position.

Figure 6A:
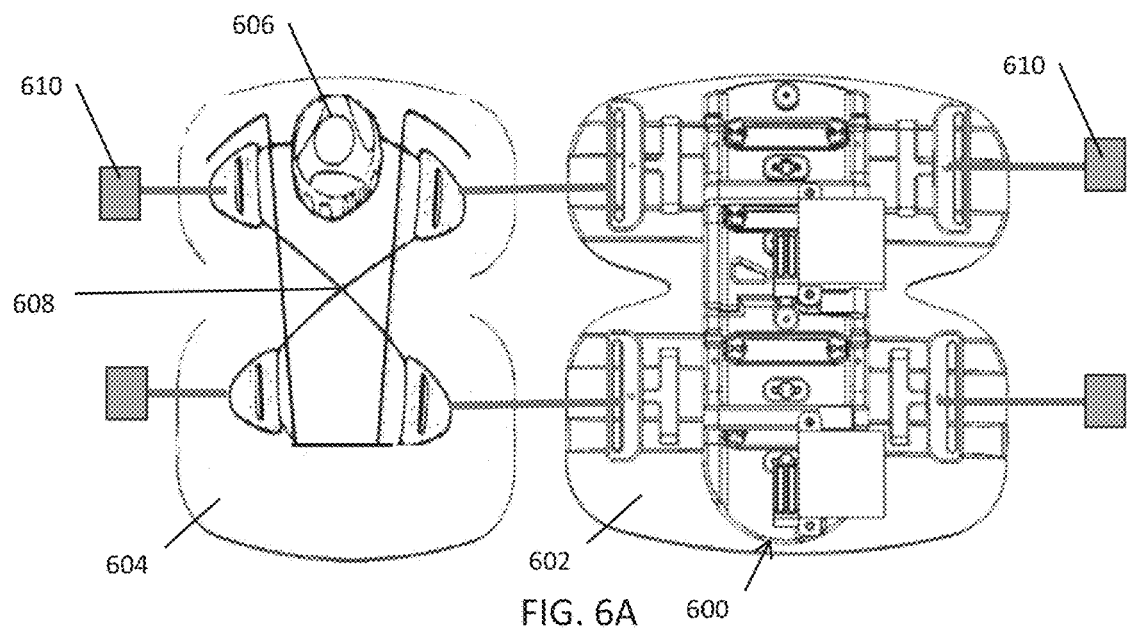
FIGS. 6A-6J illustrate various embodiments of closure and compression mechanisms that can be used to fasten the compression device to a body part.
Figure 6B:
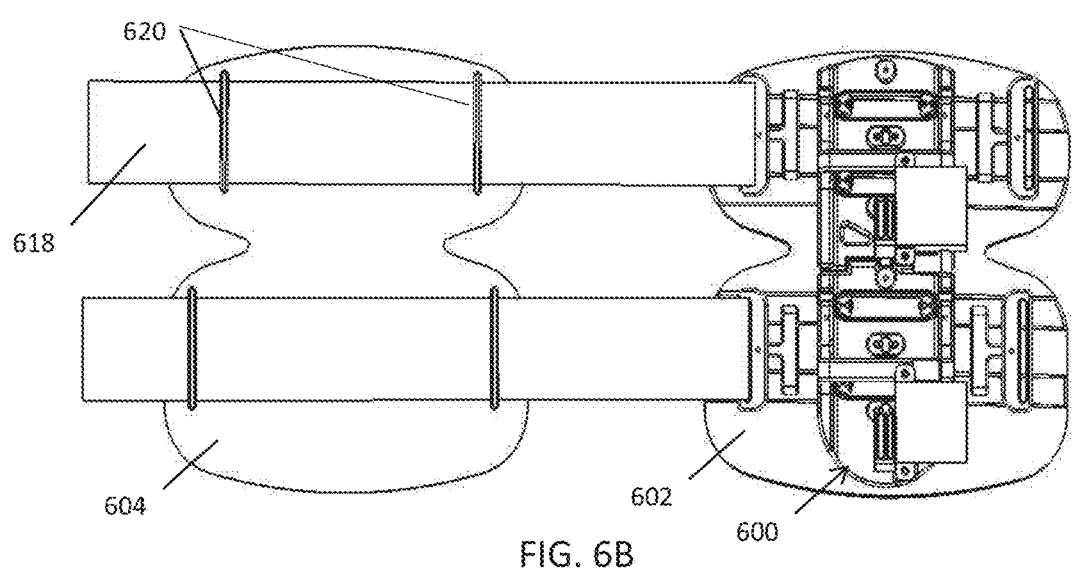
Figure 6C:
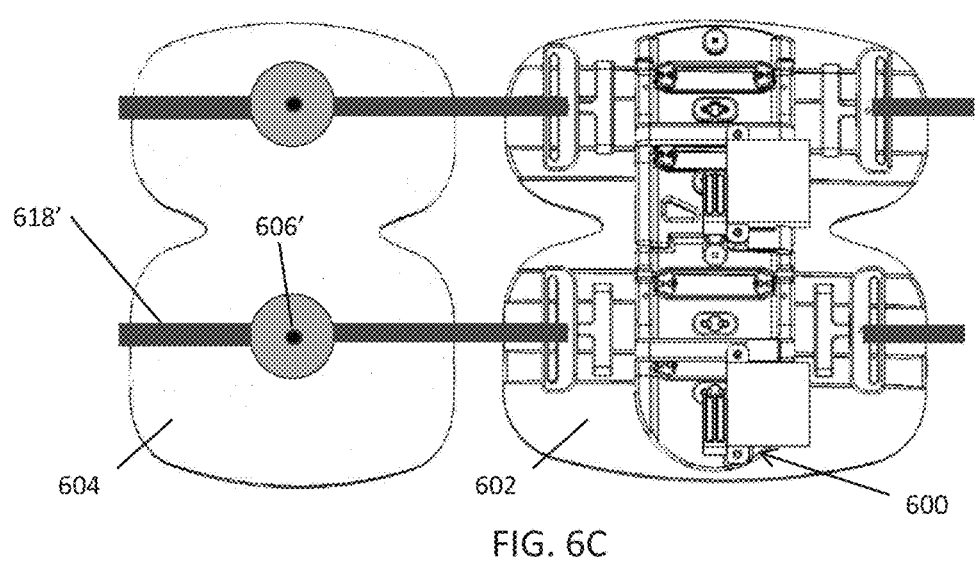
Figure 6D:
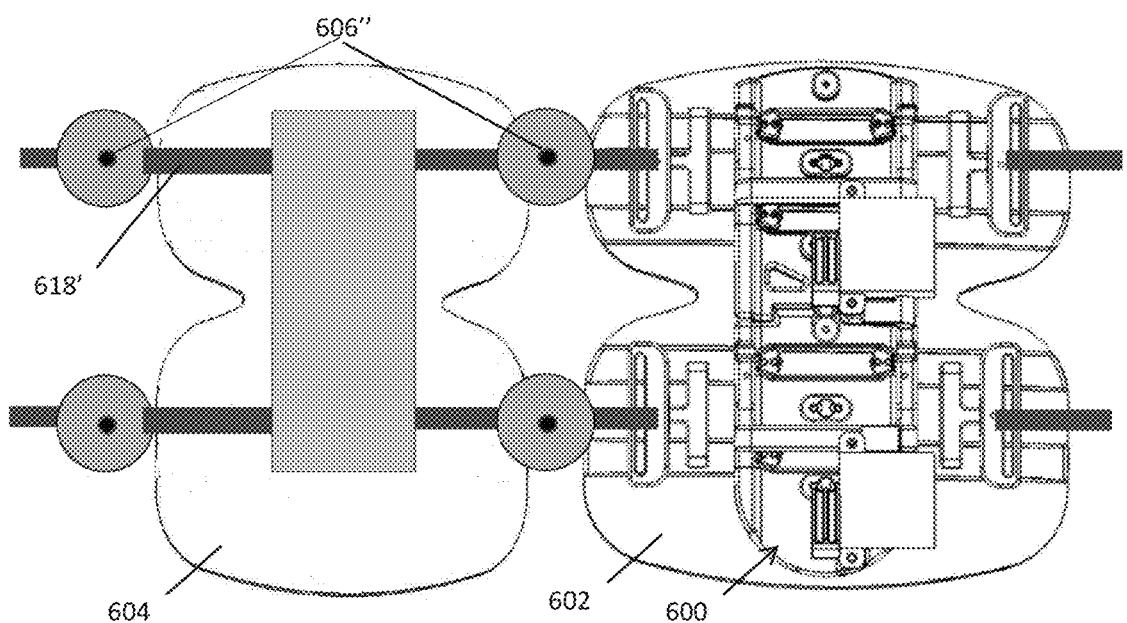
Figure 6E:
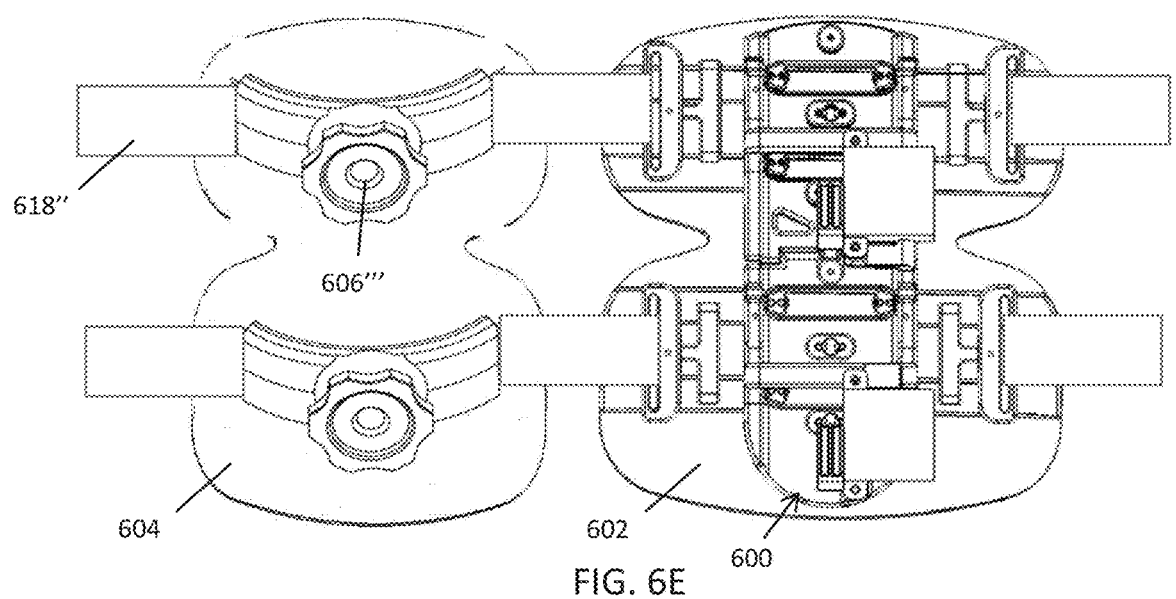
Figure 6F:
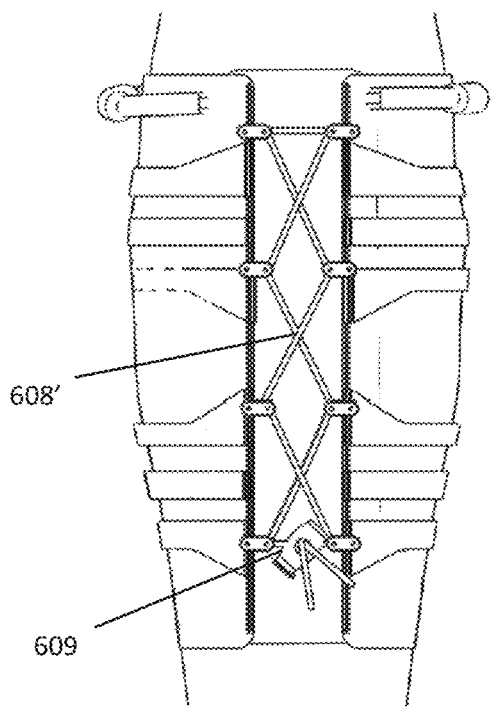
Figure 6G:
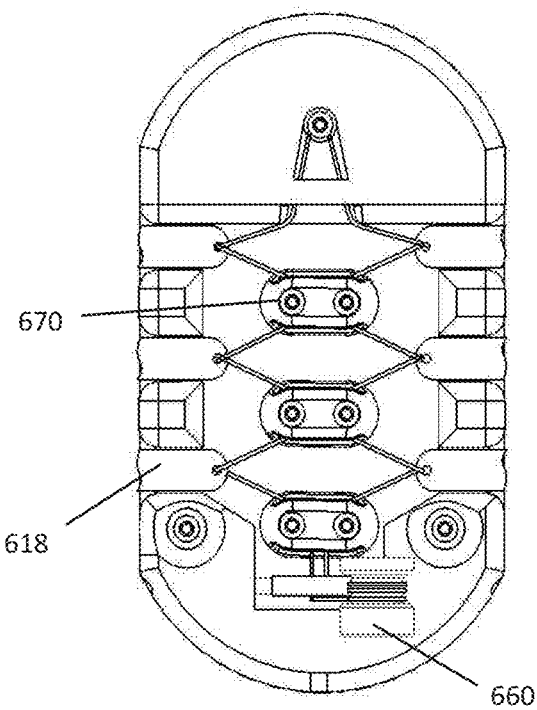
Figure 6H:
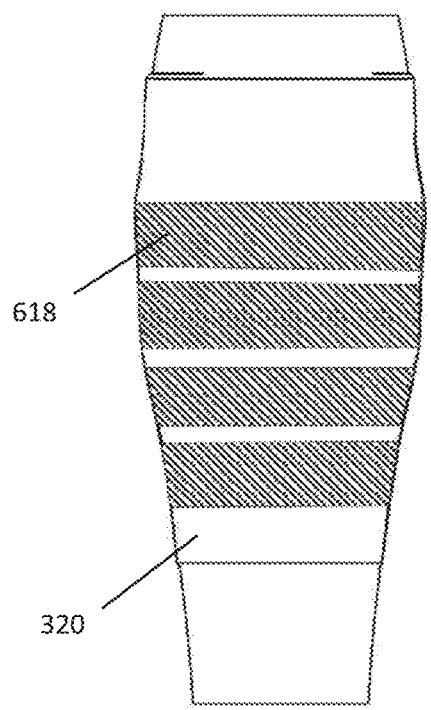
Figure 6I:
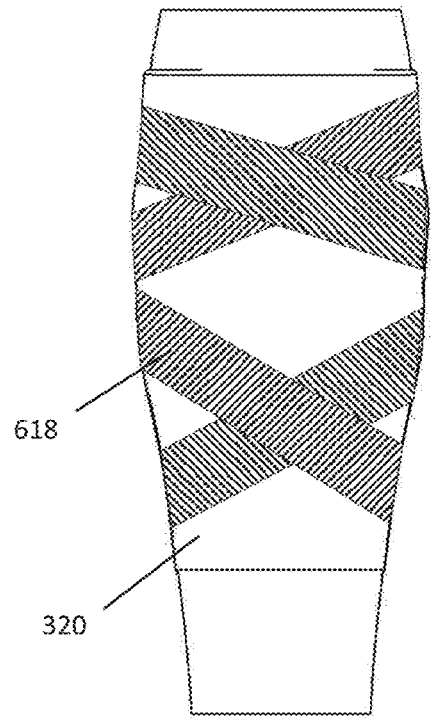

The compression straps of the system, as shown in FIGS. 3A, 6G, and 6H for example, may be pre-tensioned to a custom patient specific compression strap index location. The straps can include a visual and/or mechanical indication on the tensioning system, such as markings on the straps, to indicate appropriate zone of pre-tensioning. Alternatively, a pressure sensor, force sensor or strain gauge can be used to measure the tension and an indicator, such as an audible sound or LED light, can indicate to the user that the correct level of tension has been reached. In some embodiments, the independent compression straps 618 can cross over each other at various location(s) to create area(s) of enhanced compression, as shown in FIG. 6I. The tension applied to the compression straps may be generated through the mechanical advantage provided by pulleys, gears, and/or multiple pulleys, which allows the force generated by the motor to be amplified when it is applied to the compressions straps. Compression straps may have areas of enhanced and/or reduced pressure applied to the leg due to area reduction or increase in portions of the strap for a given force or tension applied to the straps. As the area of the strap increases, the force applied by the strap is dispersed over a larger area, which reduces the pressure applied. Alternatively or in addition, the compression straps can apply enhanced or reduced pressure to the body part by increasing or decreasing the force applied to the compression straps. The compression straps may be tightening and secured using a variety of mechanisms, such as a hook and loop fastener or ratcheting mechanism, for example.

As shown in FIGS. 6A-6J, a variety of closure systems can be used to secure the compression device 600 on the body part, and optionally over a compression stocking 320. For example, the compression straps 618 can be replaced with or used in conjunction with another force transmission component, such as a pad 602 and/or backing component 604, which can conform to a portion of the patient's body part, such as the front, side, or back of the patient's lower leg, for example. The backing component 604 can also include and/or be integrated with a closure system for attaching the device to the body part. For example, as shown in FIG. 6C, the closure system can include a tightening mechanism 606 and a lacing system 608, as described in U.S. Pat. Nos. 6,202,953; 7,954,204; and 8,468,657. In some embodiments, as shown in FIG. 6B, the backing component can be used instead with compression straps 618 using hook and loop fasteners by simply positioning the backing component 604 under the compression straps 618 and securing the compression straps 618 to the backing component 604 using strap guides 620. Fasteners 610, such as clips or buckles or magnetic fasteners for examples, can be used to open and close the closure system around the body part before engaging the tightening mechanism. Sensors, such as pressure sensors, temperature sensors, and accelerometers can be embedded in the backing component.

The pad 602 and backing component 604 can be a molded EVA foam or plastic that fits over the front portion of the lower leg. Use of the pad and backing component may allow the compressive force to be more evenly transmitted to the body part than using discrete compression straps alone, which may improve patient comfort. The backing component can be sized and shaped to cover the portions of the leg that are adjacent or proximate the lace of the closure system in order to ensure that the lace does not transmit force directly against the patient's skin. If compression straps are used, the backing component 604 can include compression strap guides 620, such as loops, for attaching and aligning the backing component with the rest of the device, as shown in FIG. 6B.

Other embodiments can utilize an alternative closure system as shown in FIG. 6C that uses a tightening mechanism 606 to tighten the lace of the lacing system 608. The tightening mechanism 606 can be a rotatable reel with a ratcheting mechanism on which the lace can be wound and unwound. The tightening mechanism 606 can be placed on the backing component 604 with the laces attached to the movable pulleys. A sensor, such as a Hall effect sensor, can be included with the reel to measure the amount of lace that is wound around the reel in order to determine the circumference of the body part, which allows the volume of the body part to be determined, which can be correlated to treatment success and efficacy. The lace can be threaded around a plurality of lace guides that form the closure system. A fastener 610, such as a clasp, latch, buckle, clip, or other fastening mechanism, can be provided to allow the closure system to be opened and closed to make donning/doffing the device easier. As shown, a magnetic clasp can be used to facilitate closure. Although only a single tightening mechanism is shown in FIG. 6C, other embodiments can have a plurality of tightening mechanisms, such as 2, 3, or 4 tightening mechanisms, or one tightening mechanism for each compression zone.

The compression components that include the compression plate, motors, pulley system, controller, battery, and drive cord can also be disposed on a pad 602, which can be made of foam or other comfortable material as described above for the backing component 602. The compression component can be removably attached to the pad which allows the pad to be changed when needed, such as when the pad is soiled or the leg girth changes.

Other closure systems can use different tensioning mechanisms. For example, FIGS. 6A and 6D illustrate an alternative reel based tensioning mechanism 606', 606". The reel can be driven by a spring that applies a known and consistent amount of force to the strap, lace, cord, or ribbon that is wound around the wheel and used for securement. The spring can be selected to provide a predetermined amount of baseline compression, such as about 5, 10, 15, 20, 25, or 30 mmHg. For each compression zone, a single reel 606' with two straps 618' can be used as shown in FIG. 6A, or two reels 606", each with a single strap 618', can be used as shown in FIG. 6E.

FIG. 6D illustrates yet another tensioning mechanism 606''' that is based on ratcheting straps 618". The straps can have teeth and a rotatable knob or other ratcheting mechanism can travel along the teeth to tighten the straps.

FIG. 6F illustrates another embodiment of a closure system using laces 608'. The laces can be manually tightened by the user by pulling on the ends of the laces. A cinching mechanism 609 can hold the laces in place after tightening or release the laces to loosen the laces.

FIG. 6B illustrates the use of compression straps 618 with hook and loop fasteners. FIG. 6G illustrates that a single motor 660 can be used to drive the pulley based drive train 670 that is used to tighten and loosen all the compression straps 618. A hole or grommet in the compression strap 618 can serve as a movable pulley. FIG. 6H shows compression straps 618 arranged in a parallel configuration, while FIG. 6I illustrates compression straps 618 arranged in an overlapping, crossing configuration with enhanced areas of compression at areas of overlap.

Figure 6J:
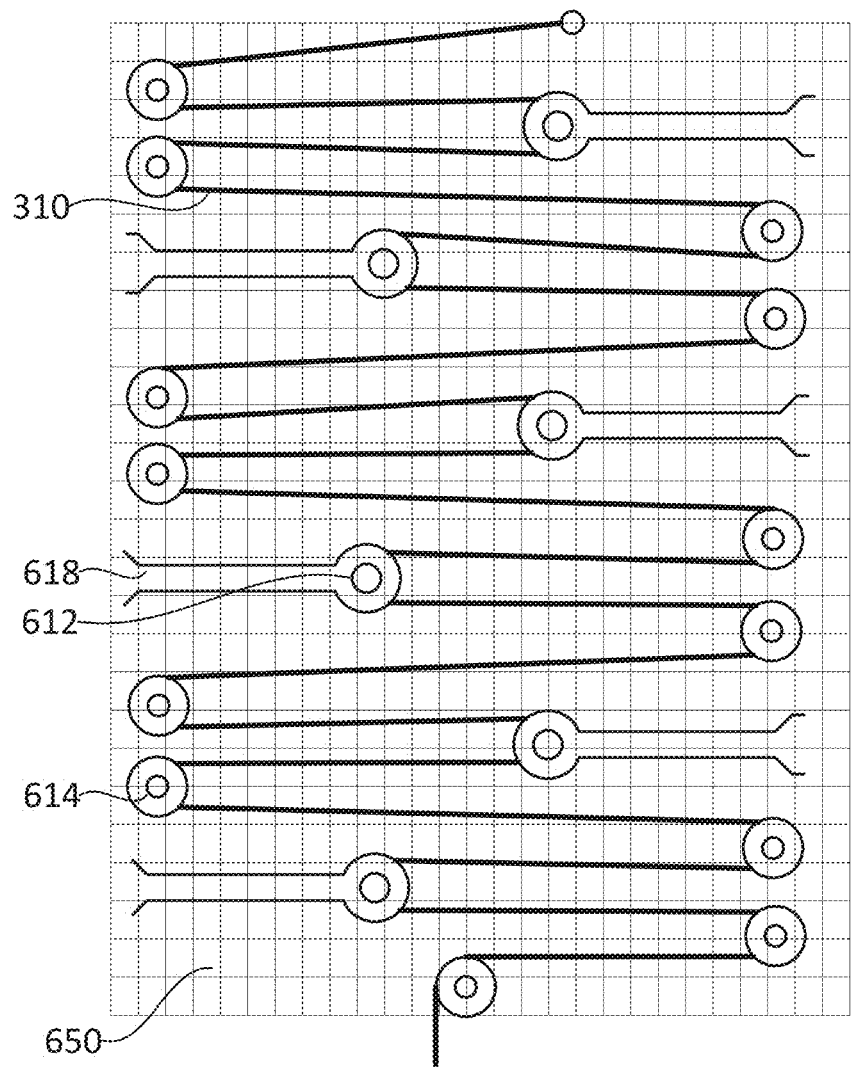

FIG. 6J illustrates an embodiment where the straps 618, drive cord 310, or laces can be integrated into the stockings 650 or sleeve along with pulleys 612, 614 or eyelets to provide a stocking with adjustable compression levels. Pulling the ends of the straps or drive cord tightens the compression stockings.

Although the descriptions herein generally discuss the use of compression straps, any of the closure systems described herein can be used instead In some embodiments, active feedback is provided via wearable sensor(s) (e.g., pressure, force and/or strain sensors) and a feedback system to index the pressure or tension applied by the compression straps and/or compression plate to a prescribed baseline condition or value. For example, the motor can be driven to rotate the drive pulley until a sensor in line with the drive cord reads a desired strain, or a sensor against the patient's skin or against the compression stocking measures a desired pressure, or a sensor measures that the motor draws a predetermined or a set current which can be correlated to a load on the motor, which can be correlated to strain.

Sensors can be integrated into the stocking, the backing component (e.g., the foam cuff), compression straps, the drive cord, the lace(s) for fastening mechanism, the tensioning reel of the fastening mechanism, the motor, and/or the force/pressure transmission components.

The system may be capable of providing user/patient feedback prior to active compression engagement to ensure that baseline conditions are achieved before beginning active compression therapy. For example, the system may be capable of verbally (e.g., in plain spoken language of recorded caregiver), auditory (beeps or other), or visually (on-board display, smartphone or remote control) providing a cue to engage the user/patient to reset device to baseline conditions. User feedback (e.g., auditory, visual, tactile) can be provided to the user when baseline compression level is achieved. In addition, user feedback (e.g., auditory, visual, tactile) can be provided to notify the user/patient that baseline compression level has not yet been reached.

In some embodiments, the drive pulley rotation is engaged for specific time interval, number of rotations, and/or power output (e.g. input drive function), per prescribed parameters, which may be predetermined or selected at the beginning or during treatment. In addition or alternatively, the input drive functions can be modulated by as sensor measurements (e.g., stain gauge, accelerometer), in order to deliver a precise and consistent amount of compression to the user/patient. For example, an integrated strain gauge, pressure sensor, and/or force sensor can be provided to provide real time feedback of compression level in the mechanical compression system so that the system can provide a predetermined, set, or desired level of compression, such as light compression less than 20 mmHg of pressure, moderate compression between 20 to 40 mmHg, strong compression between 40 and 60 mmHg or very strong compression over 60 mmHg. The pressure sensor, force sensor, or strain gauge can be positioned against the skin or against the stocking and under the base plate, compression straps, compression mechanism, pads, and/or backing to measure the interface pressure, which is the actual pressure applied to the body part, in contrast to an inflatable compression device that may only report the inflation pressure.

Integrated strain gauge plethysmography on the wearable treatment system can be used to adjust therapy system with real time feedback. The sensors can be placed on a skin facing surface, such as the back of the compression plate as shown in FIG. 3C, to directly measure the pressure and/or force applied to the body part. Alternatively or additionally, these sensors can be placed on the skin facing side of the backing component and/or integrated into the stockings. Alternatively or in addition, the sensors can be positioned and placed to measure the tension in the drive cord, which may indirectly indicate the amount of compression applied to the body part. The compression to the body part is generated by creating tension in the drive cord using the motor. The tension generated in the drive cord can be transmitted and amplified by use of a pulley system(s) to drive compression straps. The pulley system can include a mixture of fixed pulleys that are attached to the compression plate as well as moveable pulleys attached to the compression straps (or laces, cords, etc. that are used for fastening the device on the body part). The pulley system may create a mechanical advantage or variable mechanical advantage per zone (e.g. by increasing or decreasing the number of pulleys attached to the compression strap or by using different gear ratios) to enhance sequential compression. The compression system may take up slack initially from a lower zone or more distal zone that is nearer the motor and drive pulley, thereby compressing the lower zones first, then sequentially compressing zones in an upward direction as slack is taken up. Sequential compression may also be enhanced by passive (friction) or active (multiple servos/motors/zones) means, and/or multiple drive pulleys (with different diameters) with clutching mechanism. Modulation of the applied compression treatment can be based upon active, real time feedback from various system sensors and/or measurements (e.g. strain gauge, pressure sensor, force sensor, heart rate sensor, blood pressure sensor, impendance sensor, clot formation detection, blood flow measurements, ultrasound sensor, wound size measurement, temperature sensor, gas sensor, blood chemistry, posture sensor, accelerometer, etc.) independent of user input. Modulation of the compression based on sensor feedback creates a smart/artificial intelligent system that can learn, adjust, and optimize treatment. For example, an integrated accelerometer on the wearable compression treatment system can be used to modulate treatment in accordance with the treatment appendage condition, such as modulating treatment based on posture and/or activity. In some embodiments, user inputs can also be entered into the system. Modulation of the compression treatment can also be based upon active, real time feedback from external data (e.g. patient weight, temperature, ambulation, cognitive, heart condition, drug reaction, database of historic treatments, analysis of user input(s)) that can be retrieved by the system through a wireless or wired connection or input into the system by the user/patient. For example, the compression delivered by the device can be synchronized with the patient's heart rate, such as delivering a compression for every predetermined or set number of heart beats, such as every 1 to 30 heart beats. The number of heart beats can be selected based on the time needed for refilling the venous vessels with blood. Synchronization with the heart rate can be particularly useful to treat peripheral arterial disease by assisting the heart pump blood to the extremities. Real time and/or historic compression achieved, including magnitude, duration, and frequency of compression, can be recorded for one or more compression zones using strain gauges, pressure sensors, force sensors, and the like, and/or calibrated current draw from the motor which can be related to and/or serve as a proxy for compression level. Any of the other parameters measured by the sensors can also be recorded in real time and/or in a historic fashion. The user/patient and/or caregiver/physician may remotely initiate, control, monitor and/or modulate treatment on the wearable treatment system using, for example, an application on a smartphone, tablet or other computing device.

The drive cord may be spooled and unspooled around a drive pulley that is fixed to the drive shaft of the motor. As the motor rotates the drive shaft and drive pulley, the spooling or unspooling of the drive cord generates or releases tension in the drive cord that is translated to individual or multiple compression straps through a pulley system that includes fixed pulleys attached to the compression plate and movable pulleys attached to the compression straps. The pulley system can provide a mechanical advantage greater or less than 1:1 depending on the pulley configuration used. For example, attaching two movable pulleys to a compression strap will generally increase the mechanical advantage to greater than 1:1, so long as the drive cord generating the force on the compression strap is oriented generally parallel to the direction of the generated force, while reducing the amount of travel of the moveable pulleys attached to the compression strap.

In addition, gearing can be used to obtain greater or less than a 1:1 gear ratio from the output of the drive motor, which also allows for the generation of mechanical advantage to increase the compressive force that can be achieved with a given motor.

In order the reduce tangle of the drive cord around the drive pulley, rotation and spooling of the drive cord around the drive pulley can be limited to about 360 degrees or less (i.e., about one rotation or less) of the drive pulley. The size and circumference of the drive pulley therefore can determine the amount of travel or spooling of the drive cord, which along with the pulley system configuration, determines the amount of compression applied by the compression straps. The size of the pulley can be chosen to have the smallest circumference that provides the desired amount of drive cord travel to generate the desired amount of compression. This would result in the smallest tangle free drive pulley, which allows the system to have a reduced, slimmer, more compact form factor.

The use of cams, different pulley sizes, different numbers of pulleys, allows for variation of mechanical advantage in specific zones, or remote adjustment of zone (e.g. use greater mechanical advantage, longer travel, drive cord with less elasticity to deliver more compression to lower leg zones). For example, the use of a cam allows the mechanical advantage to be varied during a compression cycle to better approximate native muscle contraction and/or to alter compression dynamics. One or more movable pulleys can be attached to each end of the compression strap in order to equalize and/or balance the forces applied to the compression strap. If a movable pulley is attached to only one end of the compression strap while the other end of the compression strap is, for example, fixed in place, then the generated force may tend to torque and twist the leg, which may be uncomfortable to the user, in addition to creating the desired compressive force. By balancing the forces with pulleys attached to both ends, the torqueing and twisting force is eliminated or reduced while still providing the compressive force. Similarly, a pulley based attachment system, as shown in FIG. 6F for example, also balances the forces applied when fastening the device to the body part, and therefore provide similar advantages. Therefore, it would be advantageous for the system and method to provide balanced tensioning of the compression straps by having both ends of each compression strap pulled equally from both ends with the pulley system to balance the force applied. Spooling the drive cord creates tension and force in the drive cord that can be transmitted to the compression straps using the pulley based tensioning system. The drive cord and other compression system elements, such as the compression strap, can be integrated partially or fully in the understocking by, for example, integrating these elements into the weave/knit of the understocking. Portions of the pulley system(s), such as the fixed pulleys, can be partially or fully attached to the compression plate and/or injection molded into the compression plate such that the pulleys are embedded within the compression plate, or woven directly into the weave of the understocking. The compression plate can be woven directly into the understocking or injection molded directly onto the understocking or can be fastened on top of the understocking. The compression strap orientation, overlapping areas of compression straps, the pattern of the compression straps on the body part (e.g., parallel, criss-cross, wider straps to narrower straps), and/or construction of the compression straps (e.g., size, width, thickness, elasticity) can be modified to achieve unique and/or desired compression waves and characteristics (e.g. straps have more area or more efficiently compress in zones of maximum compression, overlapping or oblique strap configurations used to gain cumulative compression or reduced compression in zones, respectively.) The compression straps can be used with a pad or shell, which can be made of foam, plastic and other materials, in order to more evenly distribute the compressive forces to the body part. In some embodiments, the pad or shell can be integrated into stockings. The pad or shell can be sized to fit the body part, and may be custom sized based on measurements of the size and/or shape of the body part. A higher density of force transmission elements (e.g. compression straps) may be used in areas where higher compression is desired. The compression straps may have inflatable zones or be entirely inflatable to pad the straps and/or may be constructed fully or partially of an inelastic material in order to efficiently transmit the compressive forces to the body part. The compression straps may have interwoven and/or integrated electronics that communicate via wire or wirelessly to a control unit. The compression straps may be constructed from knit, woven, electrospun, sheet, and/or extrusion materials or composite of textiles or non-textiles (microdenier). For example, the compression straps may be made from EVA foam or a plastic covered with a textile.

As shown in FIGS. 3A-3C and 7A-7E, the system and method may include a rigid or semi-rigid compression plate 316, 716, 716', 716" that is pulled into the appendage or body part, such as the lower leg, and released via an attached drive train mechanism, locally compressing the area under the compression plate. The compression plate facilitates and allows selective pressure to be applied to specific vascular, muscular or lymph regions. The compression plate is pulled into a specific anatomical area in a balanced condition (i.e. substantially without torque as described herein) due to both ends of the compression strap being attached to movable equalizing pulleys and connected to the same drive cord, which ensures that equal force is applied to both ends of the compression strap. The compression plate may be fabricated with one or more zones that may be shaped with different areas in different zones to achieve a specific compression paradigm for each zone. Because pressure=force/area, either or both force and area to which force is applied could be varied per zone or per condition. For example, making one zone of the compression plate smaller than another zone while subjecting the zones to the same force, results in a higher pressure being exerted by the smaller zone. Alternatively or additionally, each zone of the compression plate can be associated with its own compression strap, which may be subjected to different forces due to having an independent motor and pulley system, or by varying the pulley configuration to modulate the travel distance of the movable pulleys and/or the number of pulleys attaches to the compression strap, for example. In addition, both area and force could be modified with areas of compression plate that telescope or collapse or expand (e.g. wings retract into the compression plate body partially or fully). The compression plate may be constructed from plastics, metals, carbon fiber, ceramics, wood or combinations thereof. The compression plate may be "3-d printed" independently or directly onto understocking using the method of additive manufacturing. The compression plate may be removable from the understocking such that the understocking, which contacts the skin, could be disposed or washed/cleaned. The compression plate may have a sealed cover to allow the unit to prevent fluid entry into electromechanical system. The compression plate may have compartments to hold electronics and a selectively removable rechargeable battery pack, which may be recharged during the release stroke of the system by, for example, attaching the drive cord to an alternator.

Figure 7A:
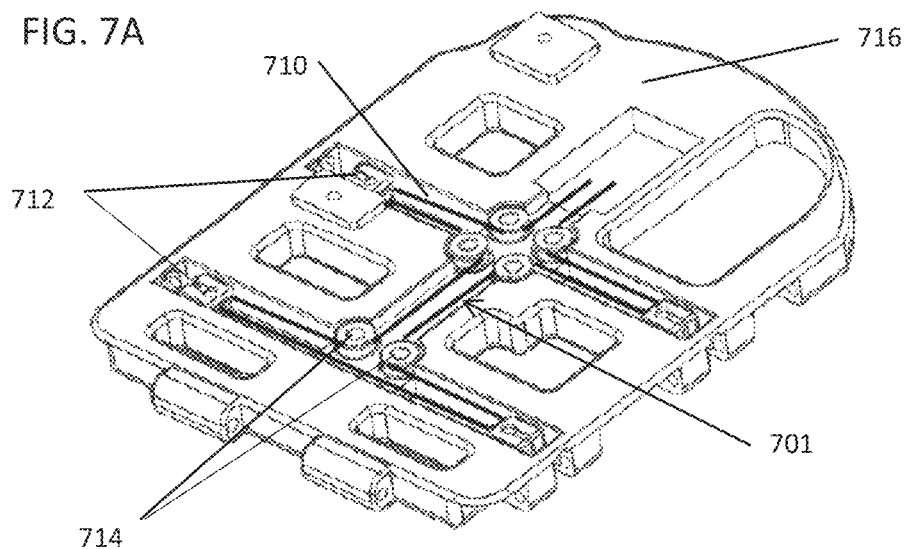
FIGS. 7A-7C illustrate various embodiments of a compression plate.

The compression plate 316 shown in FIGS. 3A-3C has the fixed pulleys 314 attached to the top surface of the compression plate 316 and the movable pulleys 312 can be positioned against the top surface or above or within cutouts in the compression plate 316 to reduce friction on the movable pulleys 312. Alternatively, as shown in FIG. 7A, the fixed pulleys 714 and movable pulleys 712 can be disposed within recessed channels 701 that are embedded within the compression plate 716, allowing the device to have a slimmer form factor. In addition, the fixed pulleys 714 and movable pulleys 712 can be aligned so that the drive cord 710 between the fixed pulley 714 and movable pulley 712 is aligned with the direction of movement of the movable pulley 712, thereby maximizing the compressive force delivered by the device. This alignment of the fixed pulleys and movable pulleys can be achieved in any of the compression plates.

Figure 7B:
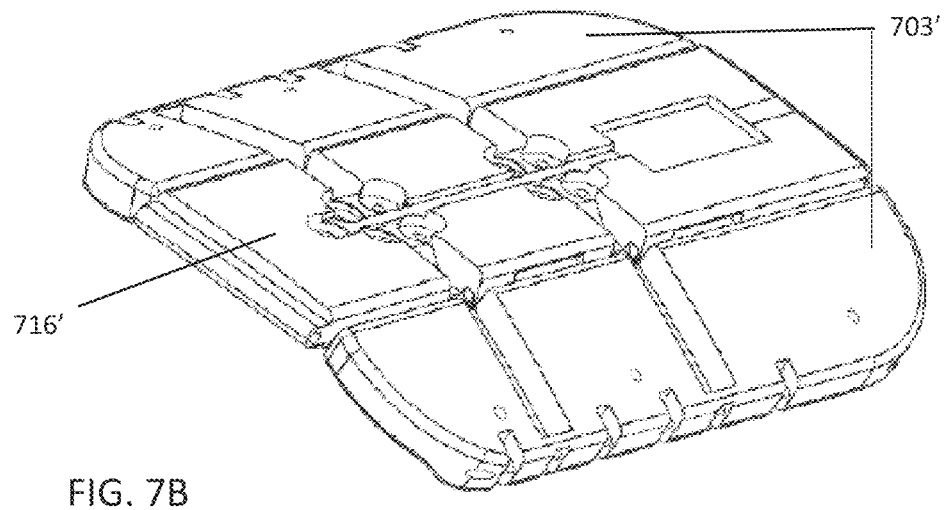
Figure 7C:
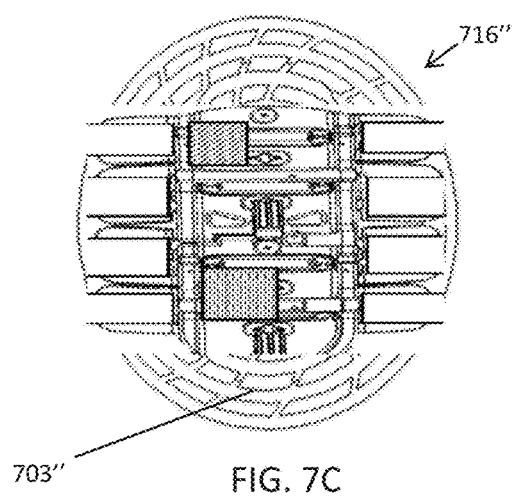

FIG. 7B illustrates yet another embodiment of the compression plate 716' with articulating side wings 703' that allow the compression plate 716' to better conform to the patient's body part. In some embodiments, the compression plate may be curved, or at least the skin facing surface can be curved, to better fit the patient's body part. In some embodiments, the entire compression plate can curved or just the side wings can be curved. FIG. 7C illustrates an embodiment of a compression plate 716" that is curved. As shown in FIG. 7C, the compression plate 716" can be curved with optionally two hinged or articulating side wings 703" that allow the compression plate 716" to conform to a joint, such as a knee or elbow or shoulder, for example. The compression plate 716" can be circular as in FIG. 7C, but other shapes can also be used, such as oblong, elliptical, or oval. These devices can be sized and shaped to provide compression to the joint and/or to the portion of the body above and/or below the joint, with each portion of the body optionally forming a discrete compression zone.

Figure 7D:
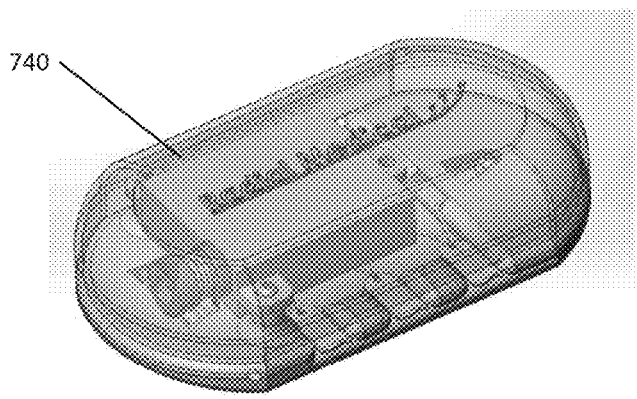
FIG. 7D illustrates an embodiment of a cover that can be placed over the compression plate to enclose the components of the compression device.

A cover 740, as shown in FIG. 7D, can be attached to the compression plate over the components such as the motor, electronics, battery, and pulleys.

Figure 7E:
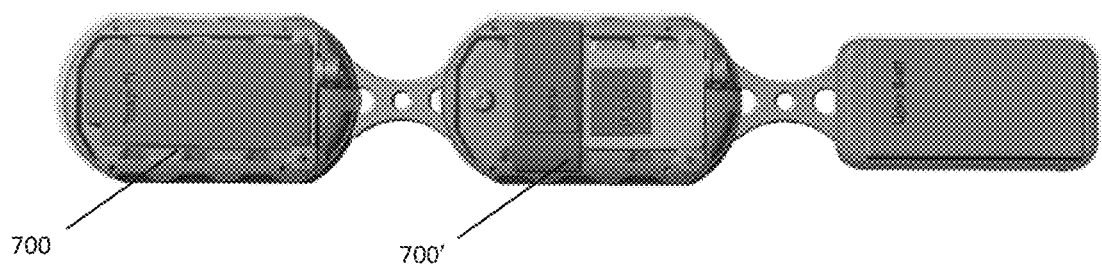
FIG. 7E illustrates an embodiment of a modular compression system with multiple compression devices that can be in communication to provide coordinated compression therapy.

FIG. 7E illustrates a modular system with two compression devices 700, 700' that can communicate with each other to deliver coordinated compression therapy, as further described herein. The compression devices may be attached independently of each other, or may be physically attached as shown through various linkages, such as an extended compression plate.

Active feedback from strain gauges can be used to evaluate efficacy of treatment and adjust treatment independent of user input for compression therapy system. The compression system may be capable of providing a compression cycle frequency of greater than 1 Hz, although in some embodiments, the system is also capable of providing a much lower cycle frequency, so as 1 compression and release about every 1 to 60 seconds, or about every 5, 10, 15, 20, 25, or 30 seconds, in order for blood to refill the veins between compressions. The speed of compression allows the system and method to achieve native or healthy flow rates, volumes, and flow dynamics curves, and can be tailored to match the needs of each patient and disease state. The speed and timing of the compressions of the individual compression zones allows the system to generate specific venous, arterial, or lymphatic flow waveforms that cannot be achieved using an inflatable cuff. The compression system may be capable of generating compressive forces greater than about 60 mmHg and in some embodiments, in excess of 200 mmHg. In some embodiments, the compression system may be capable of generating compressive forces between about 0 and 60, 70, 80, 90, 100, 110, 120, 130, 140, 150, 160, 170, 180, 190, or 200 mmHg. The compression system may be capable of providing a circumferential stroke length of greater than about 0.5 in per compression zone, or greater than about 0.1, 0.2, 0.3, 0.4, 0.5, 0.6, 0.7, 0.8, 0.9, or 1.0 inch per compression zone. The circumferential stroke length is the reduction in circumference of the system, i.e. the compression straps and compression plate wrapped around the body part, and body part during a compression cycle. In some embodiments, the compression system is capable of delivering zone specific treatment, meaning each compression zone can independently deliver a prescribed amount of compression at a prescribed cycle frequency.

Figure 8A:
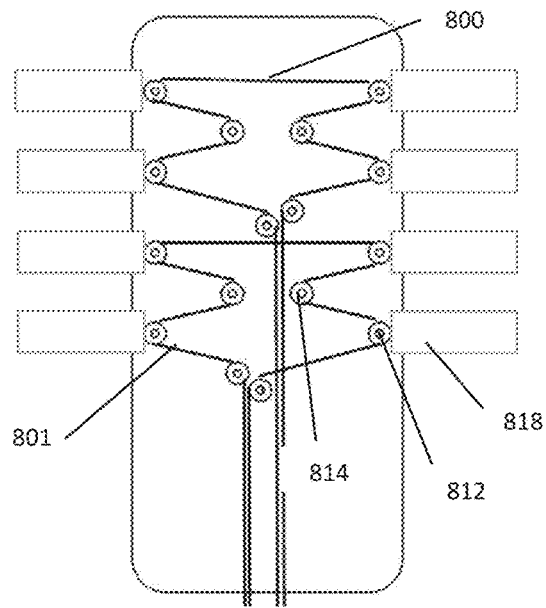
FIGS. 8A-8E illustrate various drive train configurations to achieve one or more compression zones.
Figure 8B:
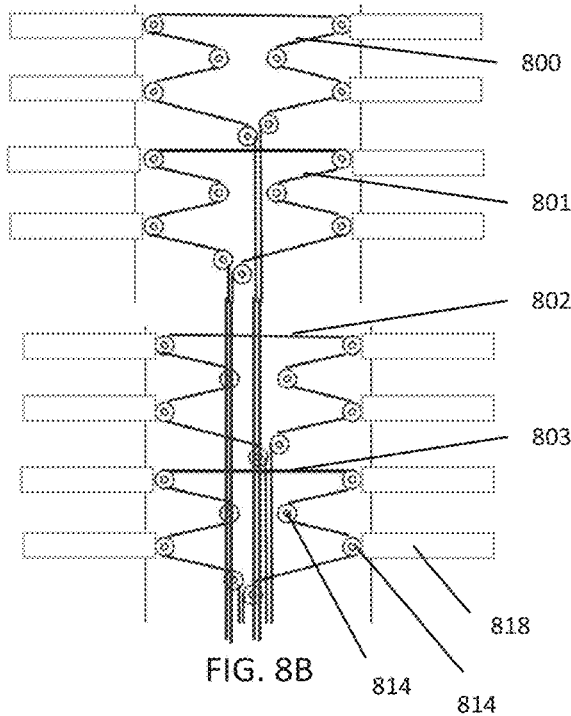
Figure 8C:
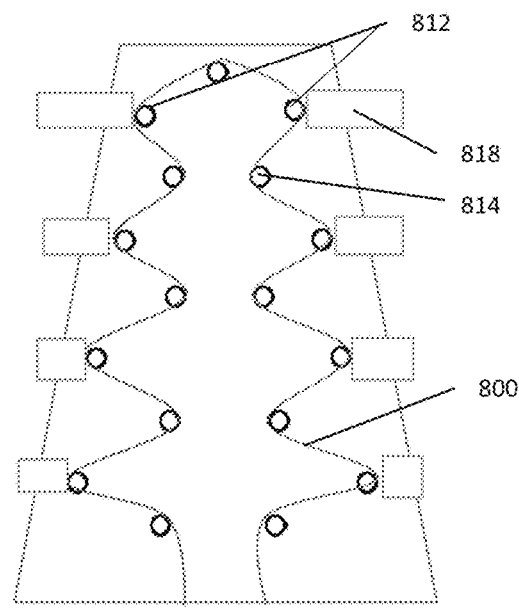

The compression zones can be generated using a variety of techniques. For example, FIG. 3A illustrates a device that provides two zones of compression using two motors, each motor driving compression for its zone. FIGS. 8A-8C illustrate alternative embodiments having multiple zones driven by a single motor. As described herein, the motor can drive a pulley based drive train having movable pulleys 812, fixed pulleys 814, and compression straps 818 attached to the movable pulleys 812. For example, FIG. 8A illustrates a two zone device that is achieved, for example, using a single motor that drives two drive pulleys on its driveshaft, with each drive pulley attached to its own drive cord 800, 801. Similarly, FIG. 8B illustrates a four zone device with a motor that drives 4 drive pulleys each with its own drive cord 800, 801, 802, 803. The drive pulleys can sized differently to provide different levels of line travel per rotation, which results in a different level of compression in each zone. Any number of zones can be created simply by adding additional drive pulleys to the driveshaft of the motor. FIG. 8C illustrates an embodiment that provides coordinated compression using a single motor and a single drive pulley and a single drive cord 800. In this embodiment, the distance between the movable pulley 812 pairs can be varied to limit the amount of compression delivered to each zone. As shown, there are 4 zones each with a different distance between the movable pulley pairs, resulting in 4 different zones of compression.

Figure 8D:
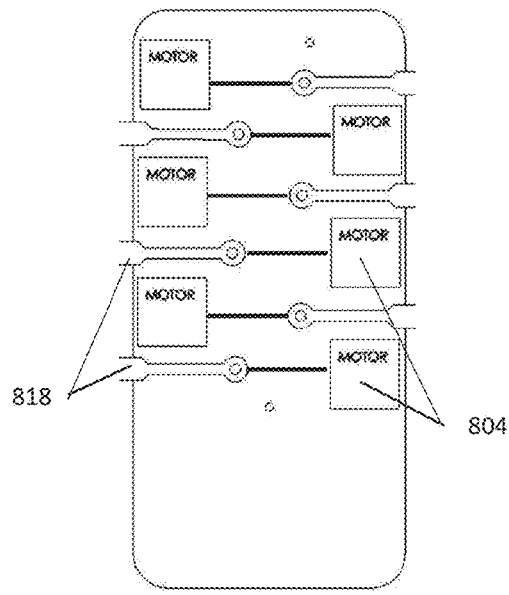
Figure 8E:
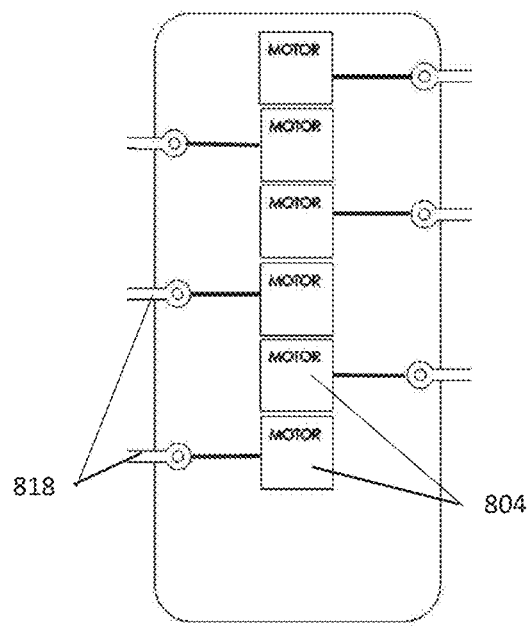

FIGS. 8D and 8E illustrate the use of multiple motors 804 to create multiple zones of compression. Each compression strap 818 or equivalent can be driven by one or two motors (e.g. one motor attached to each end of the compression strap). As shown, the motors 804 can be placed on the outer edges of the compression plate. Alternatively, FIG. 8E illustrates motors 804 being placed in the middle of the compression plate.

As shown in FIG. 7E, the compression systems and devices and methods described herein may be used in a modular and interconnected fashion. The individual units can optionally include mechanical and/or electrical linkages and/or interconnects that allow multiple units to be physical and electrically connected to each other. For example, magnetic fasteners or other fasteners, tabs and interlocks can be used to connect adjacent devices together. Wireless or wired communications can be included to allow synchronization of therapy between all the interconnected units. Wireless communications allows multiple devices to work together even if the devices are not connected together physically or electrically. Synchronization of the units can involve adjusting the magnitude, the frequency, the duration, and other compression parameters of the multiple units to achieve a desired fluid flow and/or compression pattern.

For example, a unit placed on the lower leg may deliver a compression to the lower leg, and then a unit on the upper leg can deliver a compression to the upper leg after a set delay in order to drive blood through the venous vasculature. These modular features allow a set of smaller devices to be combined into a larger device that can still provide coordinated compression between each of the compression zones in the combined system. In addition, the units can have different sizes to fit the different body parts, such as the lower leg, the upper leg, the lower arm, the upper arm, the hand, the fingers, and the torso, for example. The units can come in multiple predetermined or customized sizes that fit various ranges of body part circumferences, such as extra small, small, medium, large, and extra large. Although the units may be synchronized, the one or more units may be operated independently and be operated at its own compression level and frequency.

Figure 9A:
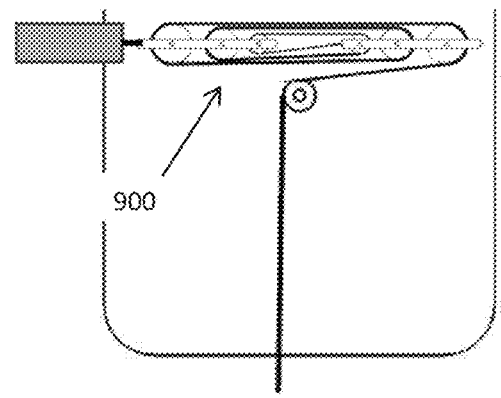
FIGS. 9A and 9B illustrate embodiments with increased mechanical advantage.

FIG. 9A illustrates the mechanical advantage that can be generated by a pulley based drive train 900 to amplify the force generated by the motor, therefore allowing the use of a small, inexpensive motor to generate large compressive forces. Multiple pulleys and/or multiple windings per pulley can be used to increase the mechanical advantage.

Figure 9B:
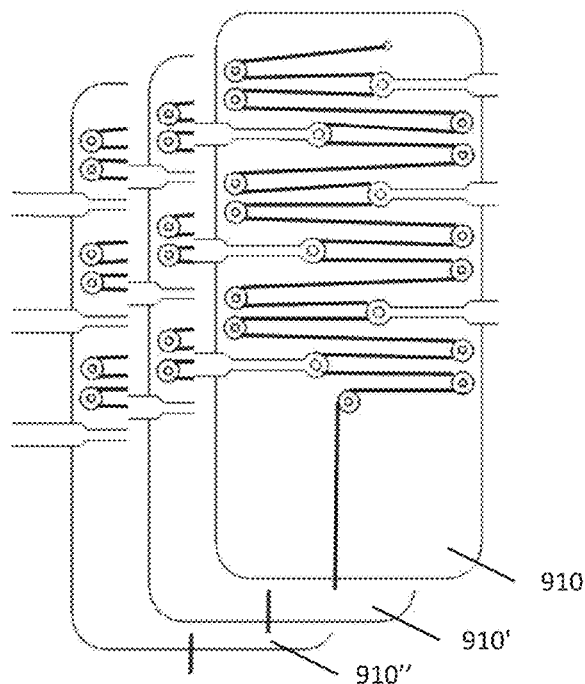

FIG. 9B illustrates a multi-layered device, with each layer 910, 910', 910" including a pulley based drive train. The layers can be sandwiched together or layered on top of each other to create a device with increased mechanical advantage while using smaller and thinner components.

Figure 10A:
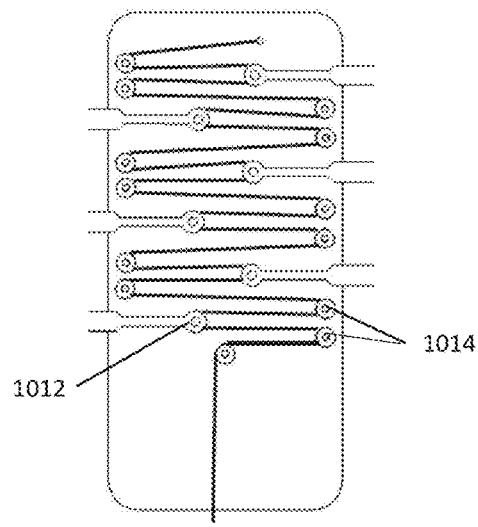
FIG. 10A illustrates another embodiment of a pulley based drive train.
Figure 10B:
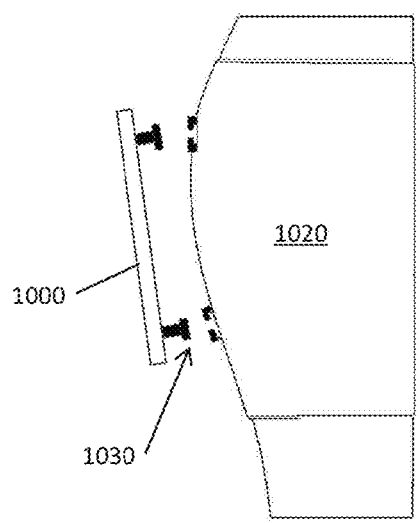
FIGS. 10B and 10C illustrate various embodiments of ways a compression device can be attached to a compression stocking.
Figure 10C:
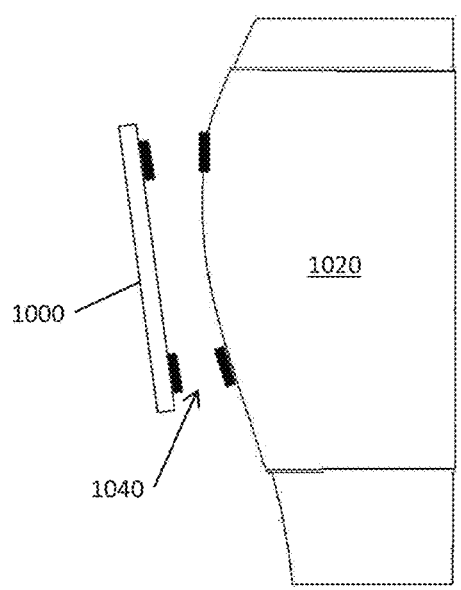

FIG. 10A illustrates that pulley travel distance can be increased for a given travel zone by positioning the fixed pulleys 1014 at the outer edges of the travel zone while the movable pulleys 1012 can be moved to and away from the fixed pulleys. FIGS. 10B and 10C illustrate that the compression device 1000 can be attached to the compression stocking 1020 using various optional attachment mechanisms that can be used in addition to alignment markings or features on the stocking. For example, FIG. 10B illustrates that a compression device 1000 can be attached to a compression stocking 1020 using snap fittings 1030, while FIG. 10C illustrates the use of a magnetic coupling mechanism 1040.

Connected Health, Precision Medicine, Smart Medicine

Figure 11:
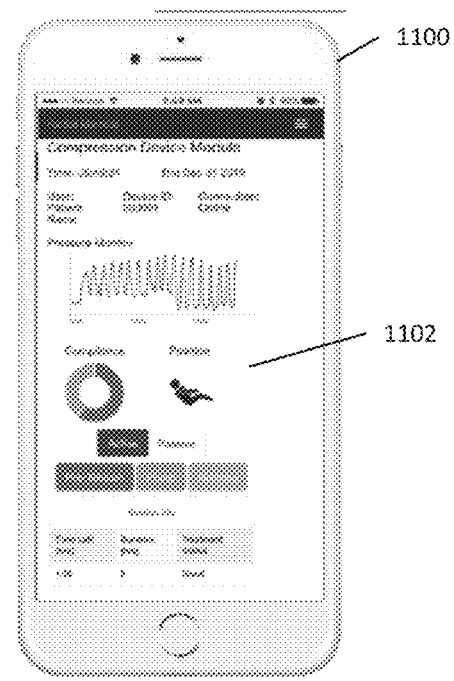
FIG. 11 illustrates an embodiment of a user interface on a smart phone.

The compression systems and methods described herein include gathering position data (e.g., compression strap/pad position, patient position—standing or laying down or sitting, device position), pressure/compression data, temperature data and/or other relevant parameters and data from the sensors of the mobile/wearable compression therapy system. The data may be transmitted wirelessly or through a wired connection to a smart phone, smart watch, tablet, laptop computer, desktop computer, other computing device or other receiving device. FIG. 11 illustrates an embodiment of a remote device, such as a smart phone 1100, with a user interface 1102 that can be used to display treatment related data, to control operation of the compression device, and communicate with a server and/or cloud computing network and/or database. In some embodiments, compression therapy treatment can be controlled remotely using the smart phone, smart watch, or other remote device.

Figure 12:
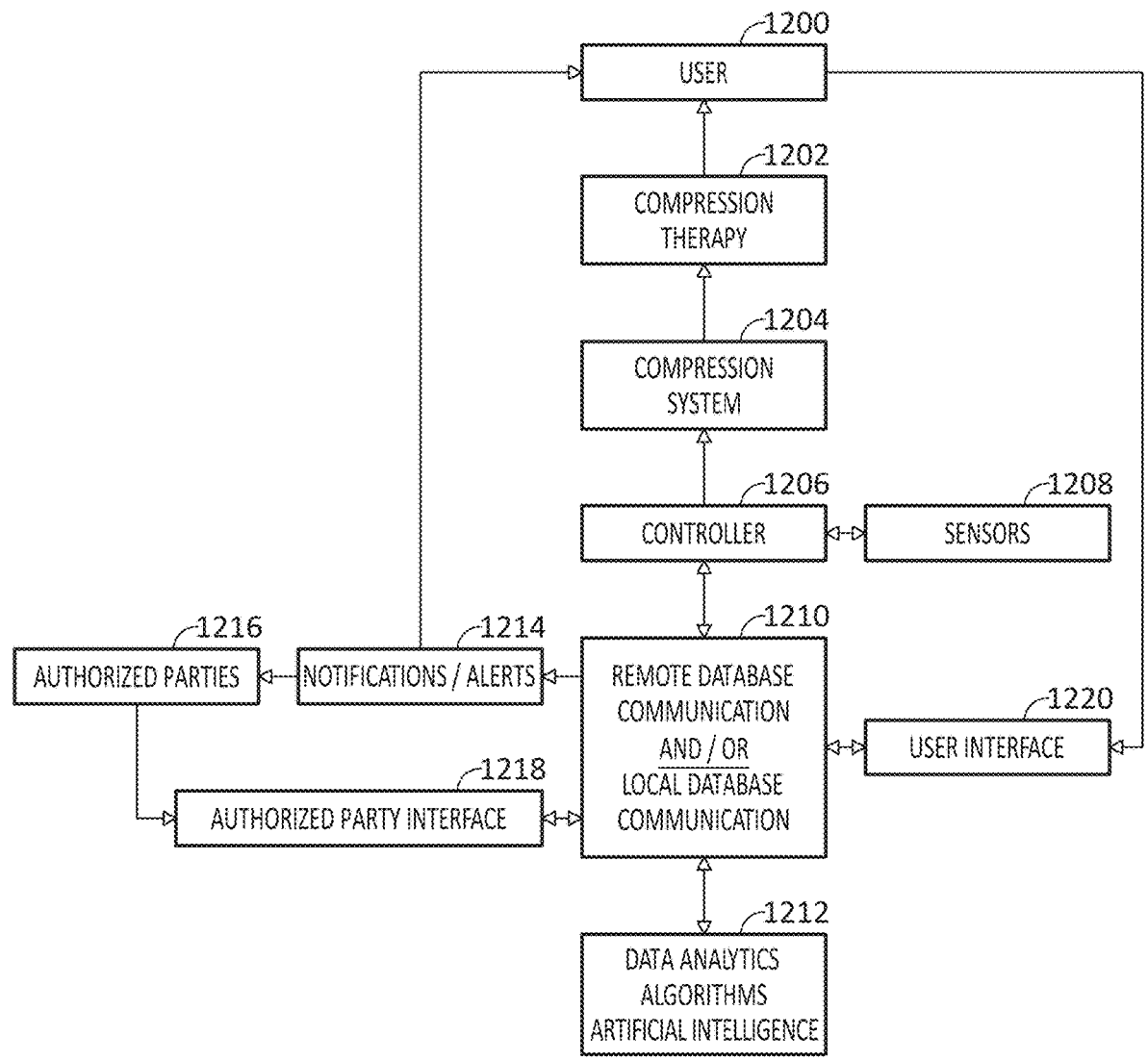
FIG. 12 illustrates an embodiment of a flow chart that sets forth the communication, flow of information and data, and/or connections between the various components of the system.

FIG. 12 is a flow chart that illustrates the communication, flow of information and data, and/or connections between the various components of the system for some embodiments of the invention. For example, the user 1200 receives compression therapy 1202 from the compression system 1204. A controller 1206 of the compression system controls its operation by, for example, controlling the operation of the motors that generate compression. The controller 1206 can request and receive data from sensors 1208 and use the sensor data as feedback to modulate the compression therapy 1202 delivered by the compression system 1204. The sensor data, treatment data, device operation data, compliance data, and other data can be recorded in on-board memory in a local database and/or sent to a remote database 1210 for local data analysis and/or remote analysis using data analytics, various algorithms such as machine learning algorithms, and/or artificial intelligence algorithms 1212. Once the data is processed locally and/or remotely, the treatment and compression parameters may be modulated as further described herein. The modulated parameters can be sent to the controller 1206 and compression system 1204 to deliver modulated compression therapy to the user. Notifications and/or alerts 1214 can be sent to the user 1200 and/or authorized parties 1216 by the local compression device, a smart phone, or by a remote device or system, such as a server or cloud computing network. Authorized parties 1216 may also obtain access to the local data and/or remote data through an authorized party interface 1218, such as web portal or application on a computer or smart phone, while the user can access the local data and/or remote data through a user interface 1220 that can be an application on a smart phone or computer, a web portal, or on the compression device itself.

Figure 13A:
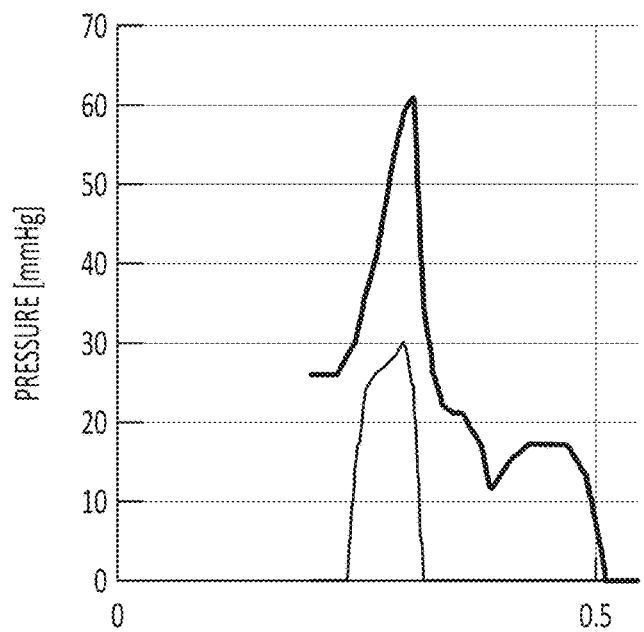
FIGS. 13A-13C illustrates exemplary data that can be accessed by the user and/or authorized parties.
Figure 13B:
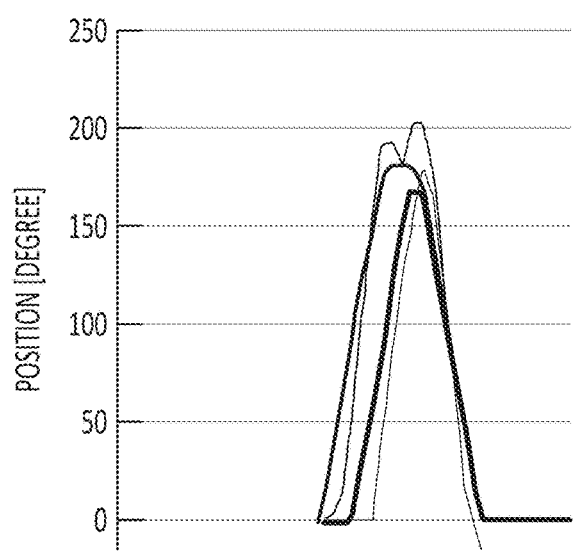
Figure 13C:
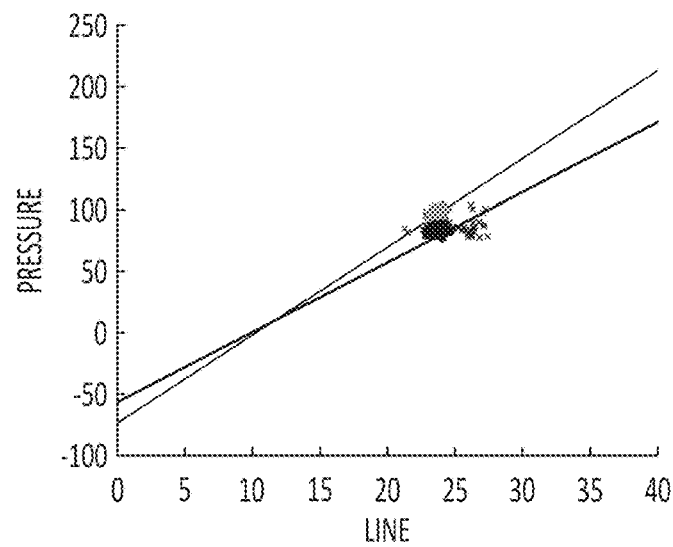

FIGS. 13A-13C illustrate exemplary compression data that can be sent to and/or viewed by the user and authorized users. FIG. 13A, for example, shows that the compression device generated a rapid compression. The two humps in the top line of the graph shows that a two zone compression can result in a bimodal compression wave, if desired, by actuating the zones sequentially.

For example, integrated, wireless strain gauge plethysmography can be performed using a strain gauge to measure the change in the circumference and volume of the body part, which allows the determination of the volume of blood being pumped. Other techniques can also be used to determine the circumference and/or volume of the treated body part. For example, the drive cord position (i.e. how much of the drive cord is wound up) can be determined by using, for example, a Hall Effect sensor to monitor the rotation of the drive pulley and/or drive shaft. The current draw or load on the motor can also be correlated with drive cord position, and both the current draw and the drive cord position can be correlated with the compression pressure delivered to the body by the system. The compression strap or other closure mechanism position can be similarly determined (i.e. using a Hall Effect sensor or other sensor on the tightening mechanism or monitoring current of the motor if a motor is used to drive the tightening mechanism). Alternatively or additionally, the closure system, such as the compression straps, can have visual indicators or markings indicating the circumference of the body part.

Strain gauge plethysmography or other forms of plethysmography can also be used to determine blood flow hemodynamics, such as blood flow velocity and heart rate. See "Beat-by-beat forearm blood flow with Doppler ultrasound and strain-gauge plethysmography", M. E. Tschakovsky, J. K. Shoemaker, R. L. Hughson, Journal of Applied Physiology, September 1995, 79 (3) 713-719. Other physiological measurements that can be determined include nitric oxide levels, which is a vasodilator and can be determined by using strain gauge plethysmography. See "New Methods to Evaluate Endothelial Function: Method for Assessing Endothelial Function in Humans Using a Strain-Gauge Plethysmography: Nitric Oxide-Dependent and —Independent Vasodilation", Yukihito Higashi and Masao Yoshizumi, J Pharmacol Sci 93, 399-404 (2003).

Plethysmography can also be used to measure the venous volume and to calculate a venous filling index (VFI). Changes in leg volume can be measured using the compression device around the calf to deliver a pre-set compression pressure with the patient in a supine position. The limb being evaluated can then be elevated to drain the venous system. Once the venous system is emptied, the leg volume is determined by the system and recorded and the patient is asked to stand, after which the change in volume is determined and recorded again. The difference in the recorded leg volume is the functional venous volume. The time needed to fill 90 percent of the functional venous volume is the venous filling time. The venous filling index is functional venous volume divided by the venous filling time; a normal venous filling index is <2 mL/sec. The greater the venous filling index, the more severe the reflux. The residual volume fraction, which is the ratio of the residual volume to the function venous volume, is directly proportional to ambulatory venous pressure, which is used to diagnose venous hypertension. Each one of the parameters, the leg volume, the functional venous volume, the venous filling time, the venous filling index, and the changes of these parameters over time as the treatment progresses, can be used by the treatment algorithm to optimize compression treatment parameters. For example, if an adjustment of compression parameters results in an indication that the patient's condition is worsening, such as an increasing venous filling index, the treatment parameters can be reverted back to the previous treatment conditions and/or further modulated.

In addition, measurement of the circumference and volume of the treated body part may be correlated to healing progression for certain diseases, since as the body part heals, the swelling tends to be reduced, resulting in a decrease in circumference and volume for the treated body part. Data from the sensors can be transmitted and analyzed, using the processors on the compression system itself and/or using remote processing from a smart phone, smart watch, tablet, other computing device, server, or cloud computing network, and compression treatment can be adjusted based upon the data.

For example, an accelerometer or gyro can be used to determine body position, such as when the patient is lying down or standing up. Since there is often a significant difference in diameter and circumference of a swollen leg between the standing and lying down positions, the system can adjust the baseline compression pressure by tightening or loosening the drive cord or the closure mechanism when it detects a change in posture. The system may also include a delay before adjusting the baseline pressure to accommodate the lag or delay between a change in posture and a resulting change in the diameter/circumference of the body part, and to avoid changing the baseline pressure for a short duration change in posture.

The system can analyze personal health data that is collected and recorded from the patient, such as data in the patient's electronic health record and the data collected by the sensors during treatment, which includes compression treatment parameters such as compression/pressure magnitude, duration, and frequency along with patient compliance, and compare and correlate the compression treatment parameters and dosing with healing response and disease state outcomes or progression which can be monitored by the system as described herein. Treatment parameters and dosing can be modulated, and healing response and disease state outcomes can be monitored to determine whether the modulated parameters resulted in improved outcomes or healing response (e.g., reduced body part circumference, diameter, and/or volume).

In addition, the system can access population health data that is compiled from a variety of sources, such as medical studies, hospital data, and data recorded from a population of patients using the systems and devices described herein or other compression devices. The population health data can include data regarding the treatment given to the patient, the treatment outcome, healing progress, patient compliance, and demographic data such as the patient's age, race, sex, and other medical conditions. The system can analyze the population health data to find the treatments that resulted in the best outcomes in patients that have a similar background or demographic and can modulate the current treatment parameters based on those treatments.

The system can also access reference data, such as geolocation, income, and weather.

The data analysis can be performed by a variety of computing devices, such as on a smart phone, tablet, laptop computer, or desktop computer that is maintained by the patient. In some embodiments, the patient controlled computing devices can analyze patient health data and use such data to modulate treatment parameters. Analysis of data can also be done on remote computing devices, such as servers or cloud computing networks, which may be better suited to perform data analysis of population health data in addition to analysis of personal health data. In some embodiments, patient controlled devices may analyze both personal health data and population health data.

Important data streams that can be sensed, monitored and/or recorded by one or more sensors on the device or independent of the device and used to by the treatment algorithm to modulate treatment include compression pressure delivered to the patient, blood pressure, compression dose (i.e. compression level/magnitude, compression duration, frequency, dwell time, treatment duration), patient's position (standing versus lying down), leg girth, activity level, venous filling time, venous volume, venous reflux, venous index, ulcer status, heart rate, oxygen level (measured using pulse oximeter for example), temperature, auditory cues such as snoring, blood flow, and ischemia. For example, oxygen levels in the lower leg and/or foot can be correlated to the ability to pump blood The mobile/wearable compression system and method can incorporate artificial intelligence, fuzzy logic, machine learning and/or other decision algorithms for determining and/or adjusting the treatment parameters based on feedback from the sensor data and analysis and comparison with personal health data and/or population health data. An onboard microprocessor system can be programmed to "learn" and adjust therapy based upon the integrated sensor data stream. The mobile/wearable compression therapy system is capable of monitoring compliance with the prescribed treatment algorithm by, for example, logging usage of the device and comparing it to the prescribed treatment regimen. An interactive compression therapy system can be provided that is capable of asking patient questions via graphical and text user interface and/or audio questions and prompts. The compression therapy system may adjust, adapt, and/or modulate treatment based upon user input or analyses of user input. For example, the patient may indicate that the treatment is not working well, and the system may then initiate a more aggressive treatment schedule by increasing the magnitude of the compression and/or the frequency of compression, and/or the duration of compression (i.e., increasing the compression dosing). The patient may input data, submit/upload pictures and/or input other information related to treatment. The data can be used to refine treatment based upon that data.

The compression therapy system, and/or a computing device, server, or cloud computing network associated with or part of the compression therapy system, may send patients reminders via text, phone, and/or email regarding their treatment or compliance with their treatment. The compression therapy system, and/or a computing device, server, or cloud computing network associated with or part of the compression therapy system, may be programmed to send caregivers, family or loved ones updates on therapy via text, phone and/or email. The compression therapy system may upload treatment data from the compression device on a prescribed schedule, such as at the end of a prescribed treatment, or at regular intervals during treatment, such as about every 1, 2, 3, 4, 5, 10, 15, 20, 25, 30, 35, 40, 45, 50, 55, 60, 90, 120, 150, or 180 minutes, or at prescribed times of the day, such as once a day at 8 pm, for example. In some embodiments, the data may be uploaded continuously or in real-time during treatment. The system and method can use real time data and/or stored historical data acquired from a population of patients using compression therapy to adjust the treatment of some or all of those patients.

The system may have remote control capability for controlling the compression therapy system that allow a caregiver or other authorized person to be able to change the treatment algorithm and/or parameters remotely. For example, remote control may include operating the compression device using a smart phone, tablet, or other computing device. These remote control devices may be paired directly with the compression device, and/or may communicate wirelessly or through a wired connection with a device that has already been paired with the compression device, such as a smart phone that has been paired with the compression device. Authorized persons other than the patient, such as an authorized health care provider, may control or modulate administration of treatment and may review recorded data to verify treatment compliance. For example, a physician may modulate the treatment prescription based upon compliance, ulcer healing progression, and data from strain gauge plethysmography, which may be used to measure the circumference and volume of the treated body part which can be correlated to healing progression since as the body part heals, the swelling tends to be reduced, resulting in a decrease in circumference and volume.

The compression therapy system may "reward" patients for treatment compliance with positive reinforcement via verbal, text or email, for example. The system may also tabulate patient compliance and generate credits redeemable for gifts, prizes, or discounts or rebates that can be applied to medical fees and/or insurance fees such as copays and/or deductibles, for complying with a physician directed course of treatment. The system may provide the patient with automated reminders and instructions for using the system. The compliance data may be accessed by the patient and/or health care provider. Notifications can be provided to the patient and/or health care provider when the patient is out of compliance (i.e., missed a scheduled treatment).

The system can include a social network component. For example, the system can provide updates to social networking sites regarding the status of the treatment and the treatment compliance of the patient. A social hub can be created for patients that are using the treatment to discuss their treatment and to provide support. In addition, the social hub can create a competition or leaderboard that rewards patients that meet treatment compliance levels.

The compression therapy system may be capable of modulating between a "passive" mode at specific set point and "active" mode at specific compression function. In the "passive" mode the compression therapy system can act similarly to a passive compression stocking to deliver a static amount of compression to the body part, except that the pressure or tension delivered by the compression system can be specified and maintained, even in the body part changes size as the result of posture and time, such as caused in the leg by standing upright versus laying down for sleeping, which can be detected using an accelerometer or gyro, for example. Light compression can provide less than 20 mmHg of pressure; moderate compression is between 20 to 40 mmHg, strong compression between 40 and 60 mmHg and very strong compression can be over 60 mmHg. The "active mode" has been described herein and provides active, cyclical compression of the body part according to prescribed treatment parameters, such as compression pressure magnitude, duration, and frequency, and overall treatment duration. Active compression can be provided while the patient is awake during specified times and/or upon initiation by the patient, while passive compression can be provided between active compression treatments, while the patient is asleep, and/or upon initiation by the patient.

Monitoring systems capable of notifying caregiver/manufacturer remotely of system malfunctions and/or need to replace components, and to automatically order and send those components to the patient/caregiver, can be integrated into the compression therapy system. The system may be capable of "learning" patient habits and adjusting treatment for convenience, comfort or efficacy of treatment based upon real-time and/or historic capture of diagnostic information.

For example, the system can identify wake and sleep patterns and activity patterns for the patient and can initiate treatments, such as active compression when the patient is awake, and passive treatment when the patient is asleep, or activate treatment when the patient is typically active and standing. The system can also identify what times compression treatments are most effective, as measured by reduction in leg girth or volume for example, as prioritize or direct compression treatment to those times.

The basic principle of operation of one embodiment is: two custom modified battery-powered brushless servo motors drive a single drive cord that is routed over a plurality of pulleys to sequentially pull and release one to six compression straps per motor. Two motors define lower calf and upper calf regions, activated sequentially to obtain natural, sequential compression from the lower to upper calf. The control unit, including electronic control systems and battery can be detached from the stocking, leaving the compression straps at a pre-defined compression level in a lightweight stocking mode.

The prototype electronic system is powered by a Raspberry Pi® zero that can support multi-client web access and local storage capability. The Raspberry Pi component can be replaced with a custom ASIC that incorporates all the needed components of the Raspberry Pi. Running the controller is a version 3.2Arduinio® platform, which can be replaced with custom ASIC and/or software. Voltage, current, Hall Effect, wifi and/or Bluetooth, force sensitive resistor (FSR) and tilt sensors allow efficient power control, positional sensing of bands, patient posture monitoring, and remote control and monitoring.

The proposed instructions for use for one embodiment are:

1) microfiber breathable soft stocking is pulled over leg, by for example, first releasing the front drawstring (running over pulley system to make release and tensioning easy), 2) pull compression device over stocking on lower leg, soft handles help user hold in place while positioning the device on alignment marking on the stocking, 3) tighten attachment system of compression device until movable pulleys are positioned against the physical stops and optionally until the compression device indicates appropriate pre-tension is achieved through an indicator, which can be auditory or visual 4) activate pre-tension routine on smart-phone to achieve appropriate set-point 5) active/passive compression routine activated, 6) release button and pre-tension released, 7) attachment system can be released and stocking removed. For cleaning, the motor drive module can be removed and stocking washed in washing machine.

Utilizing tension band positional, strain, current draw and pressure data, the device can incorporate strain gauge plethysmography capability, where the volume changes of the limb in response to applied pressure facilitate venous disease diagnosis. This would be very useful as it can be used to actively monitor progression of treatment and adjust if needed. Caregiver could remotely monitor real-time treatment progress and compliance. Ideally, this allows the clinicians to remotely make changes and schedule patients for visits based upon objective treatment data. This would reduce the burden on providers and facilitate better outcomes for this significant population of patients. This system also has significant market potential beyond venous ulcer treatment as it can be optimized for other conditions in which IPC is proven but compliance is low including DVT prophylaxis, lymphedema and peripheral arterial disease.

Current embodiments of the Radial system can achieve up to about 90 cm/s venous blood flow velocity in the veins in the legs. Pneumatic systems cannot achieve these venous blood flow velocities because of the long time it takes to fill the gas bladders, typically about 1 to 3 minutes, whereas the Radial system can deliver full compressions at a frequency of up to 1 Hz or more, such as up to 2, 3, 4, 5, 6, 7, 8, 9, and 10 Hz. Initial testing using the smart phone interface and remote wifi or Bluetooth control of the system has been successful with pre-tensioning, cycling and release modes achieved. Initial testing has demonstrated successful proof of concept that the Radial Medical SVS system is capable of delivering uniform and clinically meaningful pressures with fully functional remote control and monitoring.

Other Applications of System

In addition to the above described embodiments, various alternative compression device embodiments may be provided in a number of different configurations to address a wide variety of external medical, internal medical, industrial and athletic applications and use cases. It is to be appreciated that the compression devices, form factor, design envelope, drive systems, operations, methods and techniques described herein may be scaled, modified, adapted or otherwise suitably configured to use these various controlled power compression mechanisms and techniques to meet the following various different exemplary use cases and applications in these and similar configurations, uses or treatment of similar disease states or patient classifications. Still further, the compression devices may be configured for operation in active mode, power driven mode, passive mode or combinations of various modes depending upon the application and desired performance of the compression device or devices if more are working in concert.

Venous Duplex Ultrasound Examination

Venous duplex ultrasound is used for the diagnosis, evaluation, and management of many venous diseases, including chronic venous disease of the lower limbs, lower extremity venous insufficiency, and most other venous disorders. The duplex ultrasound includes (1) real-time B-mode ultrasound imaging that can generate images of the blood vessels and other soft tissues, and (2) pulsed Doppler ultrasound to determine blood flow characteristics, such as velocity, direction and laminar or turbulent flow. A linear 5-7 Mhz ultrasound transducer can be used for imaging and Doppler.

The examination typically involves performing both the imaging and Doppler measurements while compressing the area under examination every 2 cm or less. Typical veins that are examined include the proximal common femoral vein (bilateral examination), the sapheno-femoral junction, the mid femoral vein, the great saphenous vein, the popliteal vein, sapheno-popliteal junction, and the small saphenous vein. Other veins that may be examined include the inferior vena cava, common iliac, external iliac, proximal deep femoral, gastrocnemius, soleal, and perforating veins. Compression of the body part is typically done using manual compression delivered by the health care professional's hands. However, manual compression suffers from practitioner to practitioner variability, compression to compression variability for a single practitioner, and practitioner fatigue. This variability reduces the utility and/or accuracy of the examination, making it more difficult to compare the results with standard guidelines. In addition, it is desirable to achieve a high peak venous velocity during the examination. Instead of manual compression, a cuff inflator is sometimes used in order to provide more reliable, controlled and consistent amount of compression. However, such cuff inflators typically take longer to reach adequate compression than manual compression, which results in longer times to complete the examination, particularly because numerous compressions are often needed to cover the area under examination. In addition, cuff inflators cannot achieve high peak venous velocities due to the relatively long fill times.

Therefore, it would be desirable to provide a system and method for providing rapid, controlled, and consistent compression to specific areas of a body part while performing duplex ultrasound.

The compression systems and devices described herein can be used to provide rapid, controlled, and consistent compression of the body part for venous duplex ultrasound examination. In one embodiment, the compression device can include one compression strap and one motor that delivers rapid compression at a predetermined or set pressure. The compression can reach the predetermined or set pressure in less than 1, 2, 3, 4, or 5 seconds. The duplex ultrasound system can be positioned downstream of the compression device. The compression system can be manually actuated, using a foot pedal, a remote control device, or a smart phone, hand held device, button, or switch for example, which may also trigger the duplex ultrasound system to take a recording. Alternatively, the duplex ultrasound system may be actuated by the foot pedal, remote control device, smart phone, hand held device, button, or switch, which then also may trigger the compression system after an optional delay. Once the recordings are taken, the compression device and duplex ultrasound system can be repositioned for the next measurement. In some embodiments, the compression system can include an ultrasound transducer to perform the duplex ultrasound examination. The ultrasound transducer can be placed on the compression plate or on an independent strap that can be fastened at or downstream of the area being compressed.

In another embodiment, the compression device can be modified to provide multiple zones of compression that can be spaced apart 2 cm or less. Each zone of compression can include a compression strap with a thickness of 2 cm or less that can be independently driven by a motor, which can be a dedicated motor for the compression strap. A separate duplex ultrasound system can be used to take the imaging and Doppler recordings, or one or more ultrasound transducers can be integrated into the compression device, such as the compression plate or straps, or provided as an additional component that can be inserted under the compression plate and/or under/above the compression straps and/or positioned on a downstream portion of the body part. For example, one ultrasound transducer can be provided for each compression zone. Once the system is triggered to start as described above for the single compression zone embodiment, the multi-zone system can actuate each zone by itself in a sequential manner to automatically perform the duplex examination over the entire body part that is covered by the device. This reduces the amount of repositioning that is required to completely examine the target area and reduces the examination time.

Exemplary Additional External Use Medical Applications—Device Configured for External Use Compression Device Configured for Chest Compression Assistance In still other alternative configurations, one or more or a combination of the compression devices or methods of operation of one or more compression devices described herein may be scaled in size, modified, or adapted to be suitably configured to provide compression to the ribs and chest area. In one aspect, such a compression device may find utility as a chest compression device such as one used for CPR. In other configurations, the sequence, rate and delivered degree of compression force may be adjusted for use in combination with compression devices working alone or in combination to provide massage therapy, lymphedema therapy, sports or activity related recovery therapy or other therapy described herein.

Figure 14:
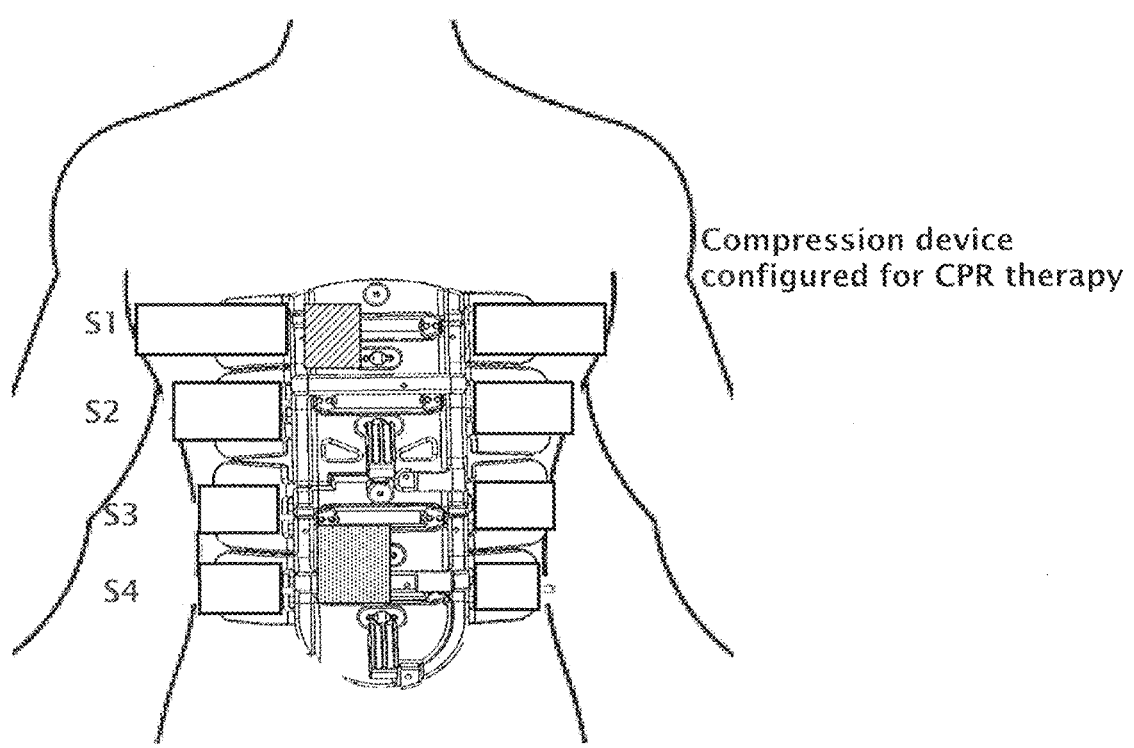
FIG. 14 is a top down view of a chest region of a patient with an embodiment of a CPR configured compression device in a "ready to use" position.

FIG. 14 is a top down view of a chest region of a patient with a CPR configured compression device in a "ready to use" position. In this illustrative embodiment, the cover is removed to show the drive system, control, power, communications systems and other components of a compression device embodiment as described elsewhere herein. CPR configured compression devices operate to provide simultaneous and even tension to the compression strap such that the resultant force is primarily a downward movement of the compression device (or optional force distribution pad as described in FIG. 15) against the sternum to produce the desired compression forces and rate of compression on the patient's heart. In one aspect, the operational characteristics of the CPR compression device are selected to impart sufficient compression force to produce peak aortic pressure to above 100 mm Hg, above 120 mm Hg, above 140 mm Hg or other selected peak aortic pressure suited to or recommended for CPR therapy. In one aspect, the operational characteristics of the CPR compression device are selected to impart sufficient compression force to produce coronary perfusion pressure to above 15 mm Hg, above 20 mm Hg, or other selected coronary perfusion pressure suited to or recommended for CPR therapy. Additionally or optionally, a compression device configured for delivery of CPR therapy may be modified to include features of the embodiments described in FIGS. 15-18.

Figure 15:
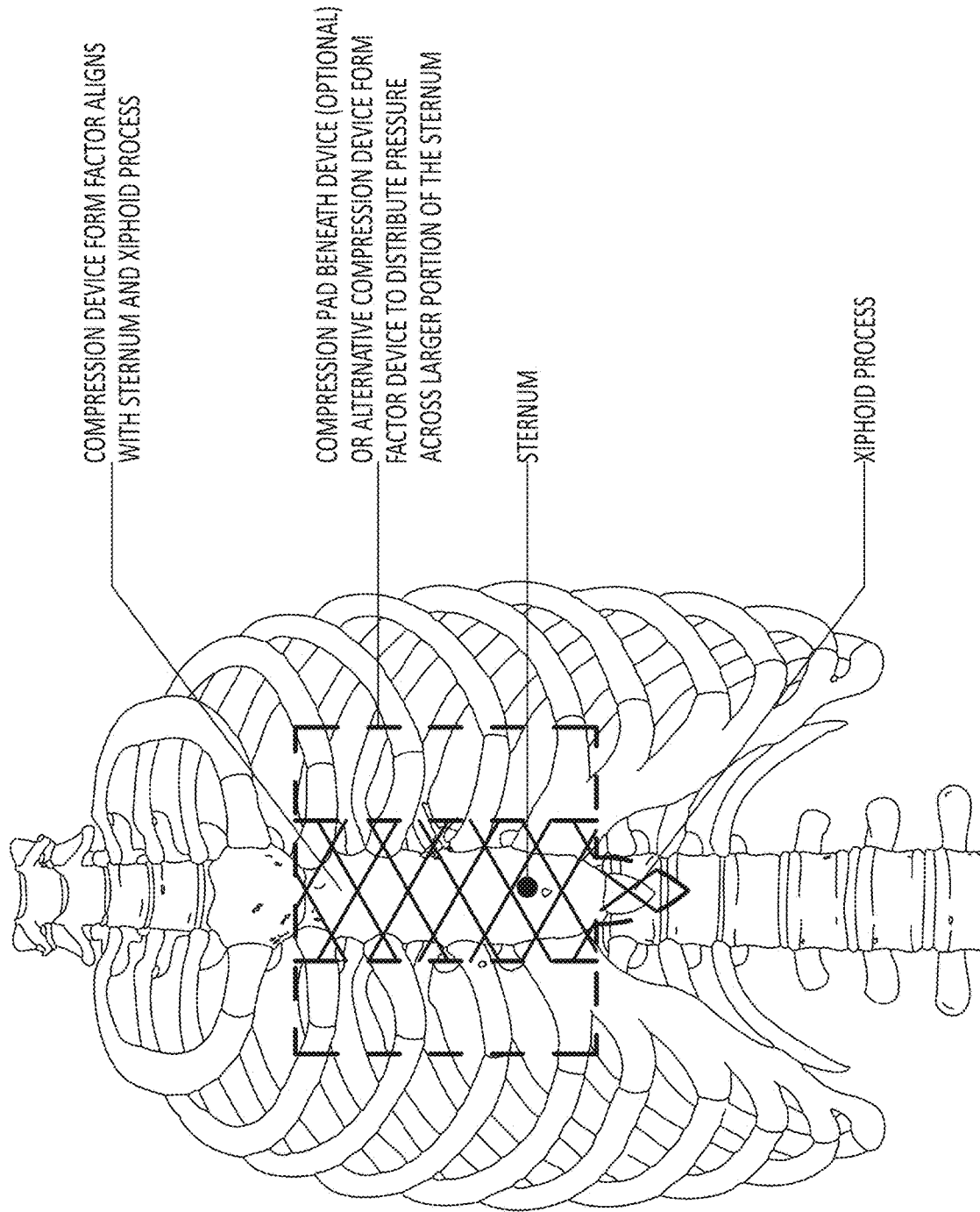
FIG. 15 is a perspective view of a human rib cage with an exemplary form factor of the compression device configured to alignment along the sternum including an alignment portion for placement on or near the xiphoid process.

FIG. 15 is a perspective view of a human rib cage with an exemplary form factor of the compression device configured to alignment along the sternum including an alignment portion for placement on or near the xiphoid process. Additionally or optionally, the compression device may be integrated with or provided with a rigid pad shaped to the general curvature of the rib cage to assist in distribution of compression forces from the centrally positioned compression device across the sternum and nearby rib portion.

Figure 16A:
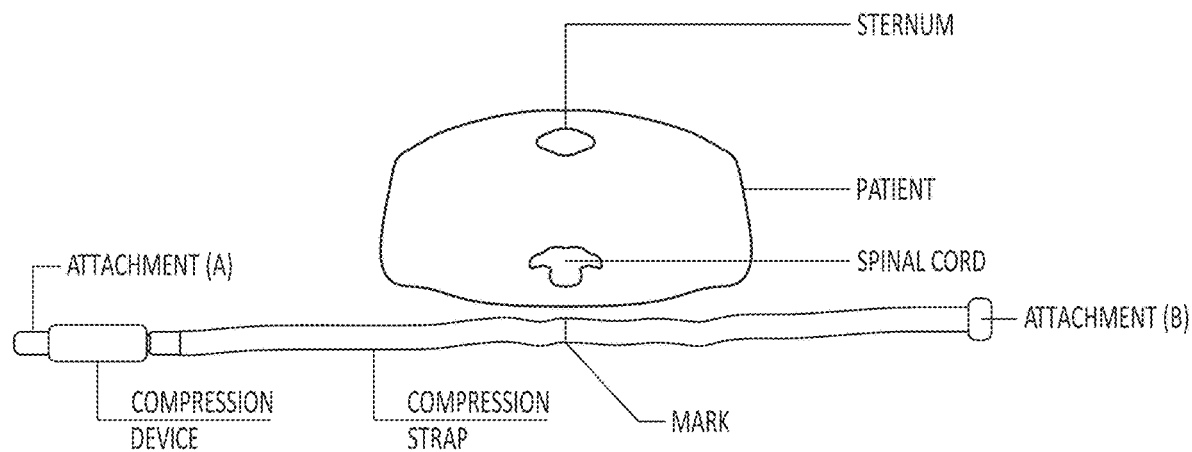
FIGS. 16A and 16B illustrate a cross section view of a patient in need of CPR compression therapy in position with an embodiment of a compression device configured to provide CPR compression therapy in an initial and "ready for use" configuration, respectively.
Figure 16B:
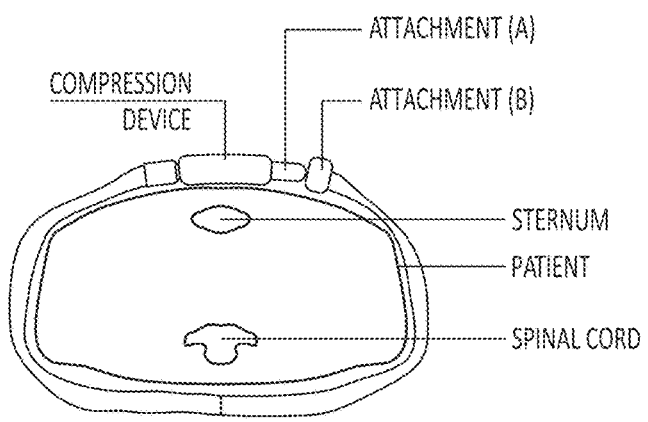

FIGS. 16A and 16B illustrate a cross section view of a patient in need of CPR compression therapy in position with an embodiment of a compression device configured to provide CPR compression therapy in an initial and "ready for use" configuration, respectively. As best seen in FIG. 16A, the compression strap is initially connected only at one end to the compression device so that the patient may be positioned on the strap as shown. A mark or other indicia may be provided for alignment of the patient to the strap. Once the patient is in position on the strap, the compression device is moved into position on the sternum and then connected to the other end of the strap. The compression device includes an attachment A and the compression strap includes a complementary attachment B. Attachment A and B include any of the disclosed or described connection mechanisms or techniques herein as well as magnets, quick connect couplings, latches and the other suitable connections that may rapidly join the strap attachment B end to the compression device attachment A end. Additionally or optionally, the strap or attachments may be adapted to adjust to the circumference of the patient including adjustment loops, slides or other take up devices included in the strap or integrated into attachment B.

Figure 17:
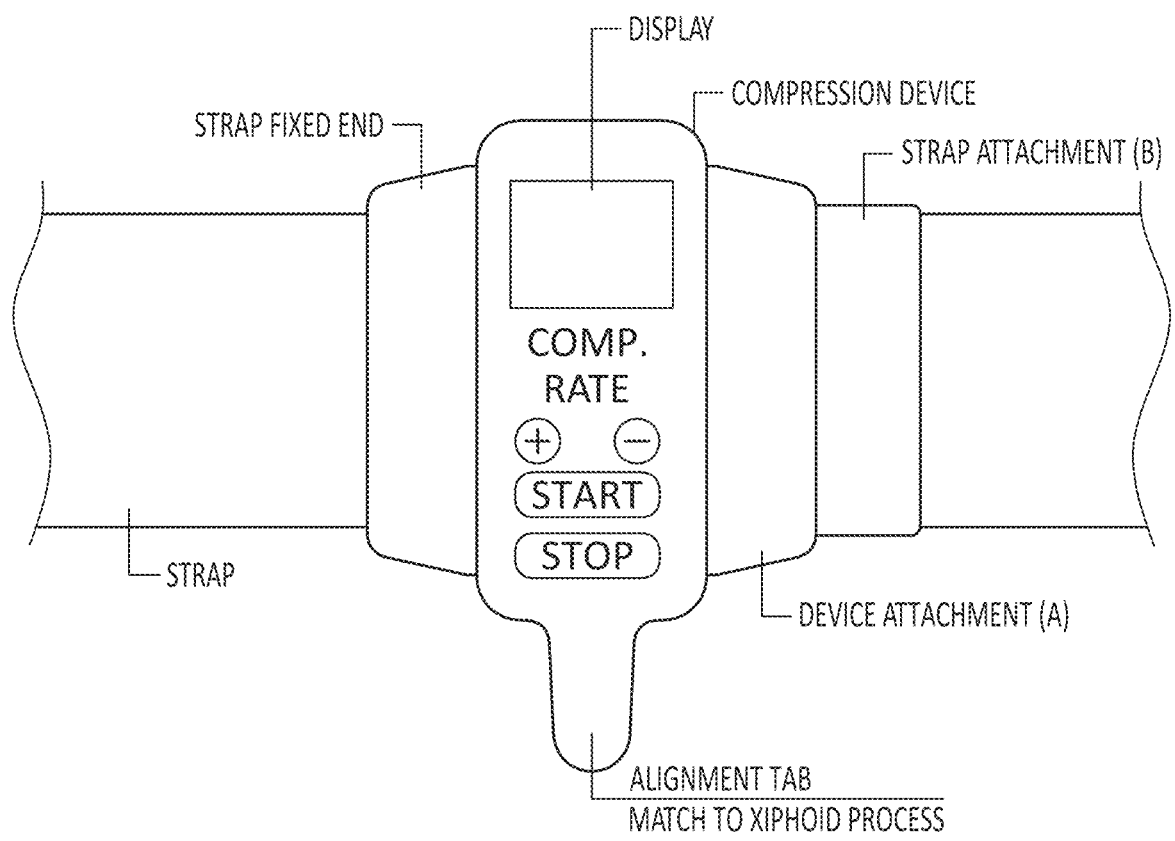
FIGS. 17 and 18 are top down views of a compression device with push button controls and touch screen controls, respectively.
Figure 18:
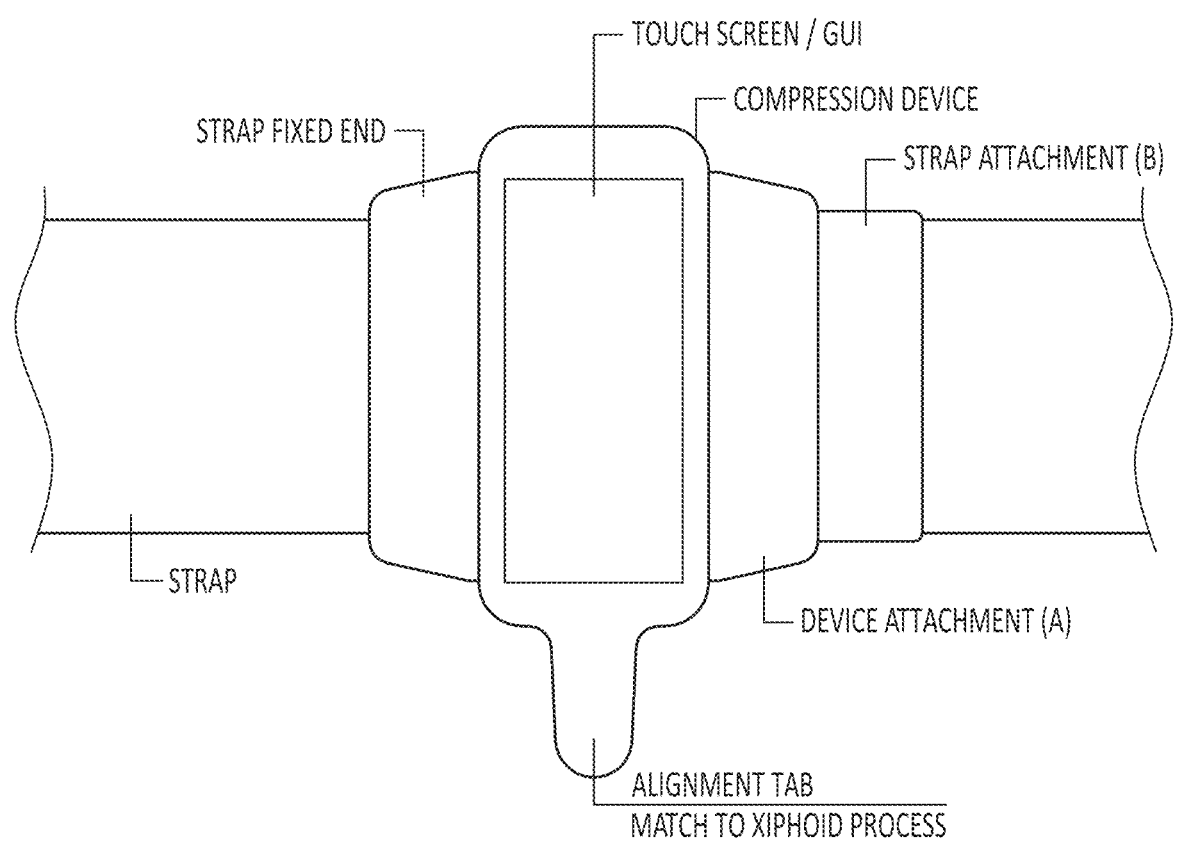

FIGS. 17 and 18 are top down views of a compression device with push button controls and touch screen controls, respectively. FIGS. 17 and 18 each illustrate a top view of a compression device as in FIG. 16B where the CPR configured compression device is attached to the patient in the "ready to use" configuration. In the "ready to use" configuration, the compression device and compression pad (if used) are positioned properly in relation to the patient's sternum and the xiphoid process as illustrated and described in FIG. 15. Additionally, the compression device attachment A is suitably coupled to strap attachment B and the strap is tightened appropriately using any of the techniques described herein.

FIG. 17 illustrates an embodiment of a CPR compression device user interface with a display for indicating the rate of CPR compression in compressions per minute, elapsed time since initiation of CPR compression therapy or other information provided by the CPR compression device controller or any sensor or instrument associated with the CPR compression device. Self-explanatory push buttons are provided to start and stop compression device operation as well as to increase (+) or decrease (−) compression rate. Other features and functionality is included as needed for CPR compression therapy or for specific configurations.

FIG. 18 illustrates an embodiment of a CPR compression device user interface with a graphical user display for indicating the rate of CPR compression in compressions per minute, elapsed time since initiation of CPR compression therapy or other information provided by the CPR compression device controller or any sensor or instrument associated with the CPR compression device. In one embodiment, the device is a touch screen with icons and pictograms to guide a user in initialization, set up, start compression or stop compression device operation and to increase (+) or decrease (−) compression rate. Other features and functionality is included as needed for CPR compression therapy or for specific configurations.

The CPR compression devices described and illustrated in FIGS. 15-18 may be modified and adapted to include additional capabilities of conventional CPR compression systems including, for example, additional control systems, sensors and chest strap designs and the like such as are provided in United States Patent Publication US 2002/0026131 entitled "Automated Chest Compression Apparatus" and U.S. Pat. No. 6,616,620 entitled "CPR Assist Device With Pressure Bladder Feedback," the entirety of each is incorporated herein by reference.

Compression Device Configured for Forearm Compression Assistance

Figure 19:
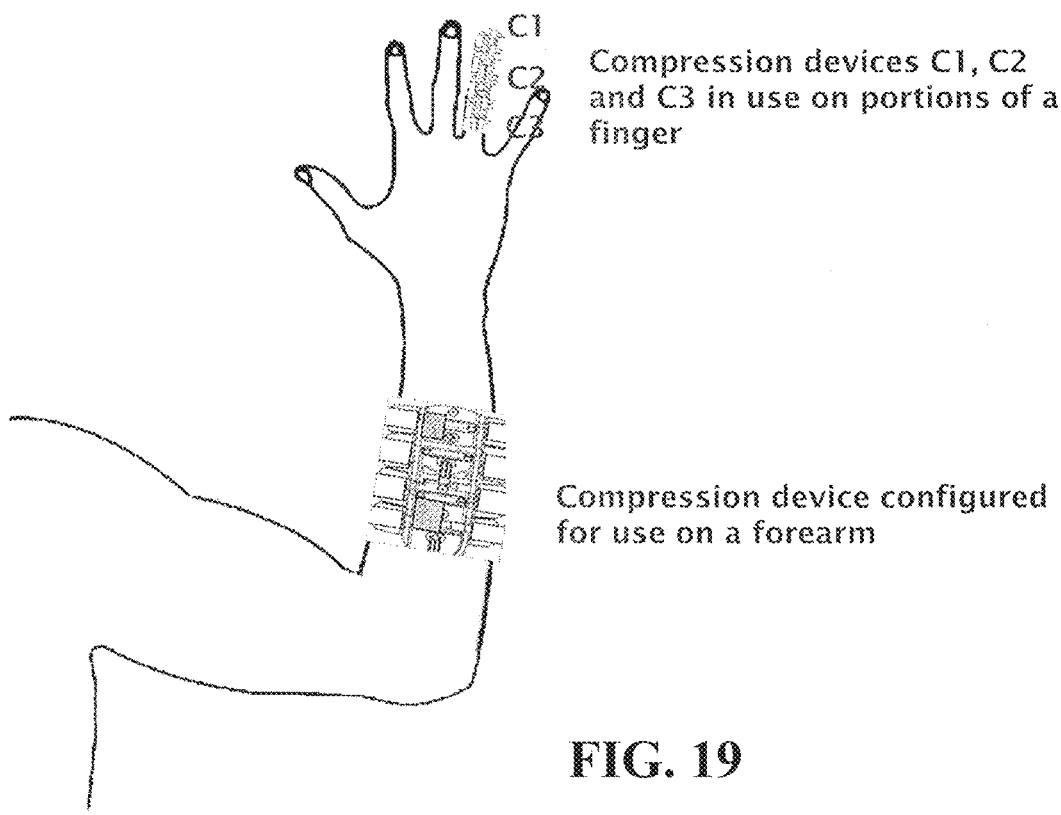
FIG. 19 illustrates a perspective view of a compression device configured for delivery of therapy to the forearm.

In still other alternative configurations, one or more or a combination of the compression devices or methods of operation of one or more compression devices described herein may be scaled in size, modified, or adapted to be suitably configured to provide compression to the forearm area. FIG. 19 illustrates a perspective view of a compression device configured for delivery of therapy to the forearm. In the illustrated embodiment, there are four straps used to apply compression therapy in a region between the wrist and the elbow. In other configurations, the compression device may be one or more devices that are segmented to allow improved confirmation to the compression therapy site. The device may be included into an appropriate garment to align the one or more compression devices with the targeted therapy site or sites in the forearm or on the arms, hands or torso. In one aspect, such a compression device may find utility as a forearm compression device such as one used for relief of symptoms related to tennis elbow or carpal tunnel syndrome.

In this illustrative embodiment of the compression devices in FIG. 19, the covers are removed to show the drive system, control, power, communications systems and other components of a compression device embodiment as described elsewhere herein. In other configurations, the sequence, rate and delivered degree of compression force may be adjusted for use in combination with compression devices working alone or in combination to provide massage therapy, lymphedema therapy, blood flow restriction (BFR) training, sports or activity related recovery therapy or other therapy described herein.

Compression Device Configured for Finger Compression Assistance

In still other alternative configurations, one or more or a combination of the compression devices or methods of operation of one or more compression devices described herein may be scaled in size, modified, or adapted to be suitably configured to provide compression to one or more portions of a finger or a thumb. FIG. 19 also illustrates a perspective view of a plurality of compression devices configured for delivery of therapy to a finger. In this illustrative embodiment of FIG. 19, the cover is removed to show the drive system, control, power, communications systems and other components of the compression devices C1, C2 and C3 as described elsewhere herein. In one aspect, such compression devices alone or with other devices on other fingers may find utility as a hand massage or compression device such as one used for relief of symptoms related to hand fatigue, tendonitis, arthritis or carpal tunnel syndrome.

Figure 20:
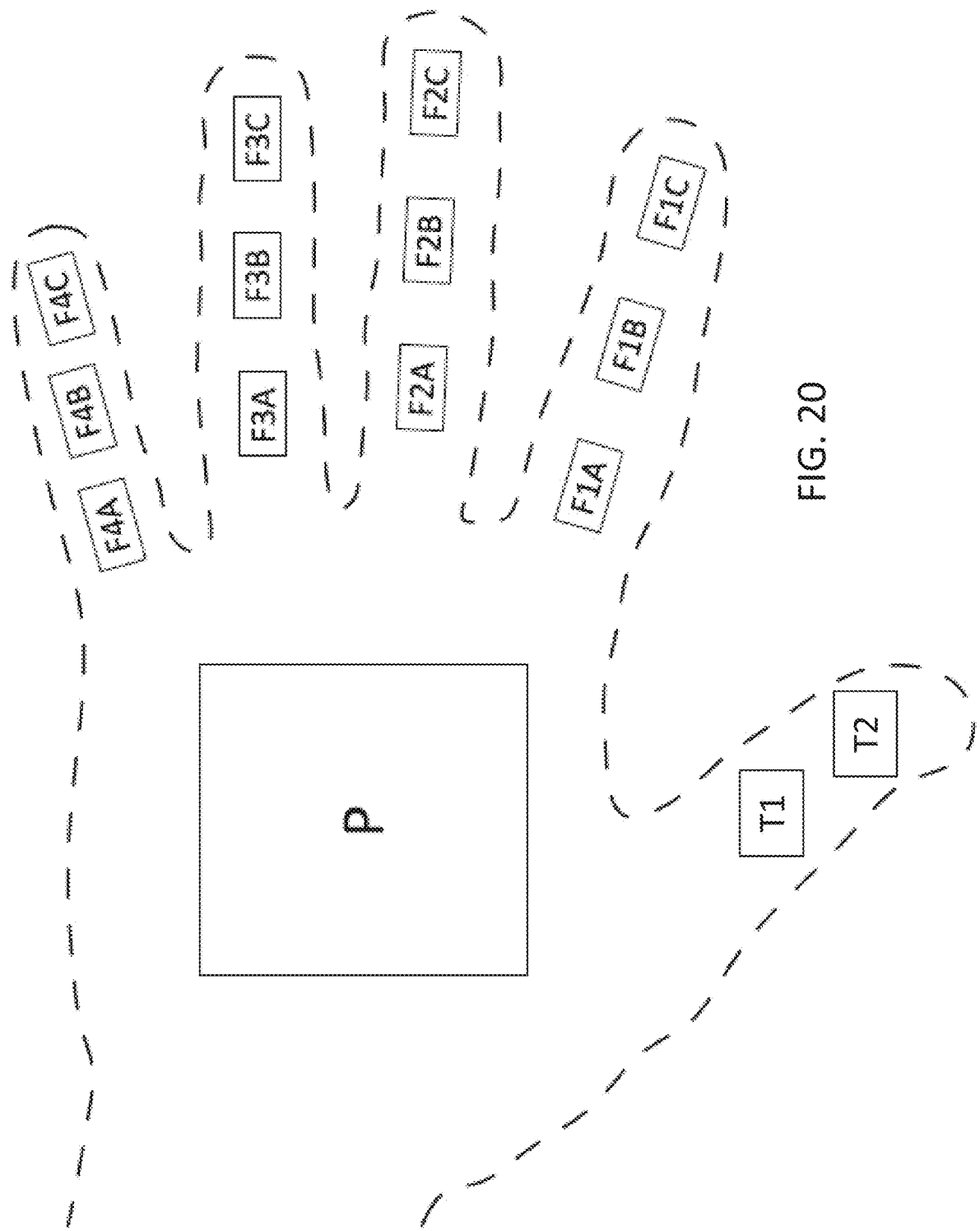
FIG. 20 is a top down view of an arrangement of a plurality of compression devices having a compact form factor sized for use on each finger, the thumb and the palm.

FIG. 20 is a top down view of an arrangement of a plurality of compression devices having a compact form factor sized for use on each finger (F1A-F4C), the thumb (T1, T2) and the palm (P). Each of the hand based compression devices is shown in position for use against a dashed line outline of a hand. The compression straps may have a ring style form factor on the fingers and thumb with a similar band to encircle the palm. While each of the finger and thumb joints are shown with a corresponding compression device, however the number of compression devices on each finger may be zero, one or two and the thumb may have zero or one. The palm device may also be omitted in some configurations. In one aspect, the selected number of finger, thumb and palm compression devices may be sized and integrated into a garment for use by a selected patient size. In one aspect, the garment is a glove or a mitten. In another aspect, the glove or mitten is included with or may be attached to another garment used for compression therapy such as a sleeve or jacket. In other configurations, the sequence, rate and delivered degree of compression force delivered by a hand compression device may be adjusted for use in combination with compression devices working alone or in combination to provide massage therapy, lymphedema therapy, sports or activity related recovery therapy or other therapy described herein. In still other configurations, one or more compression devices may be used in conjunction with a split, supports or immobilization using compression on a cast or split structure to support treatments for sprains and fractures.

Compression Device Configured to Provide Smart Tourniquet Functionality

In still other alternative configurations, one or more or a combination of the compression devices or methods of operation of one or more compression devices described herein may be scaled in size, modified, or adapted to be suitably configured to provide compression to an affected portion of the body where a desired treatment is the use of a tourniquet. In one illustrative embodiment, a limb such as a leg has been lacerated resulting in damage to one or more arteries or other blood vessels. The compression device is configured to be positioned on the limb over the affected vessel and then operated to apply pressure sufficient to act as a tourniquet. The compression device may be used directly on the limb, in combination with absorptive material such as gauze or a wound dressing.

FIG. 21 is a top down view of the legs of a subject having an injury in the thigh of the subject's left leg suited for treatment by use of a tourniquet. FIG. 22 is a front view of the subject in FIG. 21 with a compression device positioned over and in position relative to the injury site to provide a tourniquet functionality. FIG. 23 is an enlarged view of the compression device of FIG. 22 showing a display and function keys for operation of the compression device to apply pressure to the affected limb to stop bleeding. In this illustrative embodiment, a display provides a single interactive prompt to the user to guide the operation of the compression device in the application of an appropriate level of compression to the affected limb. In this embodiment, buttons responses for Yes (Y) or No (N) are provided. In this illustrative example, if the subject is still bleeding, then the answer to the displayed question "Bleeding Stopped?" is NO. Pressing the N button causes the compression device controller to increase the level of compression applied to the limb. In one aspect, the controller may operate to continuously increase compression level until the user responds to the prompt as "Yes" and presses the Y button. In another aspect the controller may operate to increase pressure in small increments, and after adjustment, present the "Bleeding Stopped?" prompt again.

FIG. 24 is a side view of an affected limb with a compression device in position at the injury site and working in conjunction with a patch. The patch in the illustrated embodiment is larger than the footprint of the compression device and is positioned over the injury site between the wound site and the bottom engagement surface of the compression device. In this and other configurations, the device reduces or relieves compression pressure at the site in order to restore flow to the affected limb upon a determination that bleeding has stopped either as measured or detected by the device or user input or sensor input in communication with the compression device.

Smart Wound Patch for Compression Therapy

Figure 25:
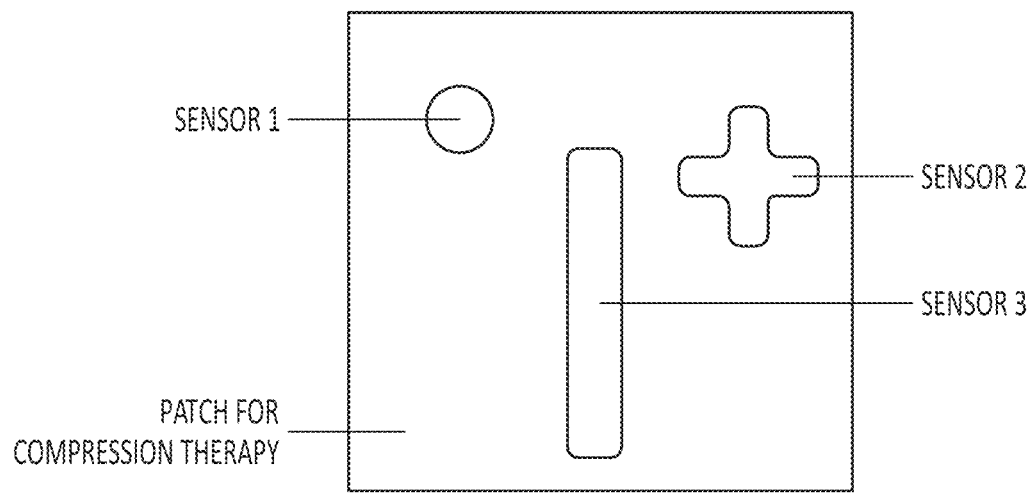
FIG. 25 is a top view of an exemplary sensor layer
Figure 26:
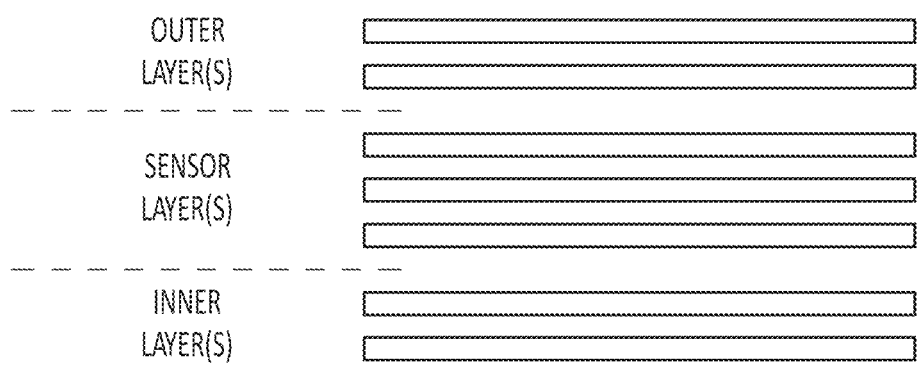
FIG. 26 is an exploded side view of an exemplary smart wound dressing patch having one or more inner layers, one or more sensor layers and one or more outer or top layers.

In still other configurations, the compression device is used with a specifically designed wound dressing sensor patch. Embodiments of a wound dressing sensor patch include one or more sensors with one or more layers of material. FIG. 26 is an exploded side view of an exemplary smart wound dressing patch having one or more inner layers, one or more sensor layers and one or more outer or top layers. A top view of an exemplary sensor layer is shown in FIG. 25. In this view, there are three sensors—sensor 1, sensor 2 and sensor 3—each of different type and location in the sensor layer. In various alternative embodiments of a smart wound patch for compression therapy, the one or more sensors are configured to provide information related to the compression therapy or the affected limb to the patient, a compression device user (such as a health care provider) or to the computer controller of the compression device. The various layers of the compression device include properties appropriate to the layer. For example, the outer layer or layers may include a water proof characteristic along with sufficient strength to bear and transmit the forces applied to it by the operation of the compression device. The inner layer or layers on the other hand, may include highly absorbent material along with pathways or conduits appropriate for the operation of the one or more sensors in the sensor layer to detect, monitor, record or measure characteristics at the wound site while the compression device is in use. The sensor patch may be coupled with or powered by the compression device so that no power supply or separate communication mode between the patch and the compression device is needed. Magnets, latches, electrical/data plugs or connections or other hybrid fitting with electrical/communication connection functionality may be used to couple the smart wound patch to the compression device to provide power, data and communications capabilities as needed by a particular compression device or smart wound patch embodiment.

Figure 27:
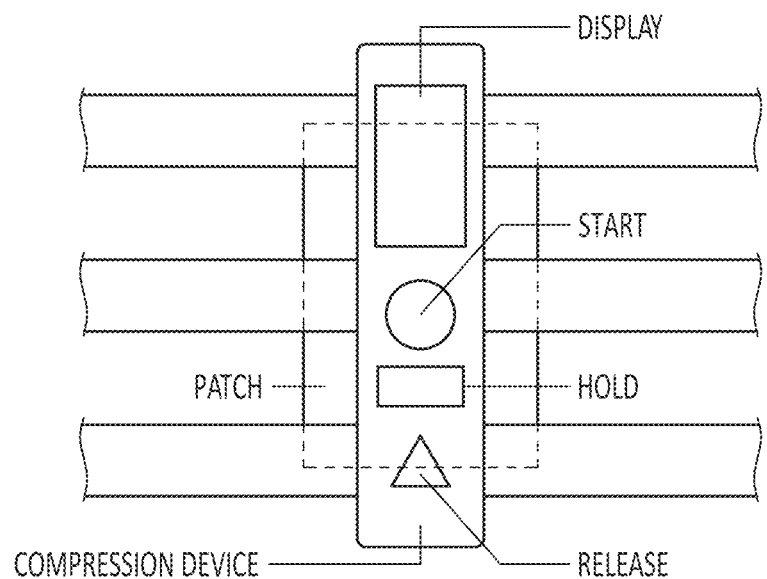
FIG. 27 is a top down view of a compression device in position with a patch on an affected limb.

FIG. 27 is a top down view of a compression device in position with a patch on an affected limb. Similar to FIG. 23, there is also shown a display and three symbol based function keys for operation of the compression device to apply pressure to the affected limb to stop bleeding. As discussed before, the compression device controller may provide instruction to be suitably presented on the display—such as an appropriate interactive prompt—to guide the user in the operation of the compression device in the application of an appropriate level of compression to the affected limb. In this illustrative embodiment, different shaped buttons are included which may also be color coded to match appropriate responses under the circumstances. While illustrated a circle, a rectangle and a triangle other shapes may be used such as a red hexagon to indicate "STOP" to hold compression level or a green circle for "GO" to increase the compression level. As before the display may provide prompts that guide the user to depress or interact with the buttons on the cover of the compression device. Also shown in this view is that the compression device form factor is different from that of the patch. This may occur is a wound dressing is already in place when the compression device is coupled to the wound site. In such an instance, the compression device is placed over and operated with the previously applied wound dressing in place. In response to the buttons on the device, compression device controller may increase, decrease, hold or temporarily reduce the compression level applied to the affected limb. In one aspect, the controller may operate to continuously increase compression level until the user responds. In another aspect the controller may operate to increase pressure in small increments, with pauses for an appropriate user response to hold or increase pressure. In one aspect, the buttons illustrated may be associated with "increase compression," "hold compression level," and "reduce—restore compression level." In one exemplary embodiment, the circle is associated with "increase compression," the rectangle with "hold compression level," and the triangle with "reduce—restore compression level."

Figure 28:
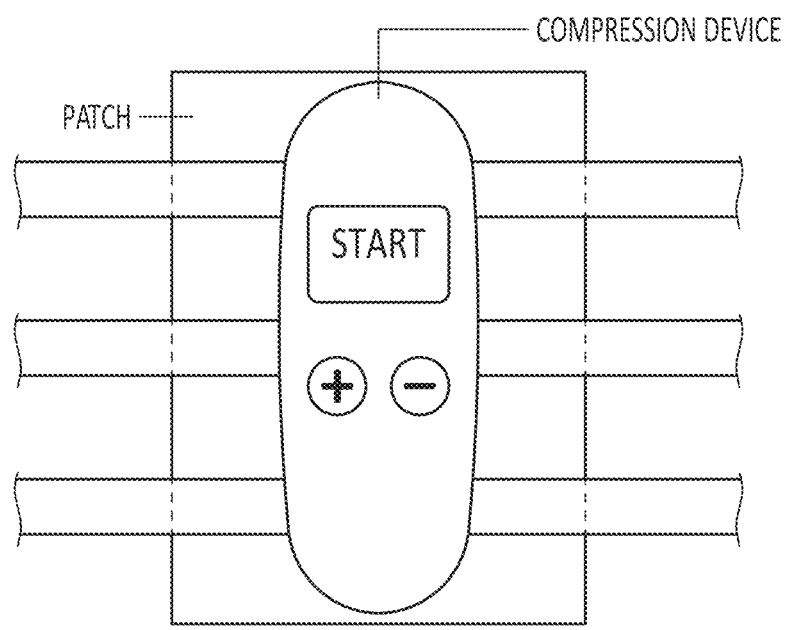
FIG. 28 is a top down view of a compression device in position with a patch on an affected limb.

FIG. 28 is a top down view of a compression device in position with a patch on an affected limb. Similar to FIG. 23, there is also shown a display and symbol based function keys for operation of the compression device to apply pressure to the affected limb to stop bleeding. As discussed before, the compression device controller may provide instruction to be suitably presented on the display—such as an appropriate interactive prompt—to guide the user in the operation of the compression device in the application of an appropriate level of compression to the affected limb. In this illustrative embodiment, the display provides a single interactive prompt to the user to guide the operation of the compression device in the application of an appropriate level of compression to the affected limb. In this embodiment, buttons responses for "+" and "−" as related to an increase or a decrease respectively in the level of compression level applied to the affected limb. Pressing the "+" button causes the compression device controller to increase the level of compression applied to the limb. In one aspect, the controller may operate to continuously increase compression level until the user responds with "−" to indicate that the desired level of compression is achieved. In another aspect, the buttons may be color coded or different shapes that the user is directed to press or interact with based on the messages on the display. In any of these embodiments, the operation of the device may also be enabled by a GUI or touch screen interaction with the display. Also shown in this view is that the compression device form factor is compatible with that of the patch. The patch is sized to be disposed between the compression device and the affected limb and be the same or larger than the foot print of the compression device. The compression device may be placed over a patch such as a smart compression patch that is already in place or the patch and compression device may be applied to the wound site of the affected limb as a combined unit.

In other compression device smart tourniquet configurations, the sequence, rate and delivered degree of compression force may be adjusted for use in combination with sensor inputs or data collected or measured by the compression device or in communication with the compression device related to the health of the patient wearing the compression device, the affected limb or an extremity of the affected limb. In the case where the affected limb is a leg, an extremity would be the foot or the toes. In the case where the affected limb is an arm, an extremity would be the hand or fingers. Examples of information related to the health of the patient or the affected limb include any measure or indicia of vascular health or damage, neurological health or damage including, for example, EKG, EEG, EMG, degree of perfusion, pulse oximetry measurements, blood flow information or other suitable information whether obtained by observation or collected by instrument. In one aspect, a sensor used to measure or provide an indicia of vascular health or damage, neurological health or damage of the patient or affected limb is provided to the compression device controller. In one specific aspect, the sensor is one for the detection of the amount of or rate of bleeding at the affected site. In one aspect an absorbent pad positioned between the compression device and the laceration is used to curtail blood flow. In alternative configurations of the compression device or smart patch, additional healing conditions are introduced to the affected limb such as introduction of oxygen, light or other wound therapy adjuncts provided by one or both of the compression device or smart patch. In other aspects, one or more sensors within or associated with the measurement of the conditions in the pad related to one or more of flow of blood or rate of flow of blood or time since no new blood flow detected may be used as a feedback loop to aid in reduction or adjustment of the compression level applied to the affected limb by the compression device. The compression device controller includes computer readable instructions for alerting a user or adjusting compression level automatically or to a pre-determined level based on a sensor reading. Additionally or optionally, the tourniquet configured compression device may reduce the compression level periodically or at a predetermined time period or on demand so as to provide for vascular circulation and perfusion of the affected limb. In one aspect, a tourniquet configured compression device includes simple controls to increase compression on the limb until bleeding stops. Once bleeding is observed to stop, the compression device holds that level of compression. If bleeding resumes, the level of compression may be increased again until the bleeding is stopped at which time the compression device holds the new higher compression level. In one aspect, the compression device includes a release button, command or functionality to be used when the tourniquet function is no longer required and the compression device releases the pressure applied to the affected limb. In another aspect, the compression device includes an adjust pressure button, command or functionality to be used when the tourniquet compression level is reduced slightly to permit circulation to the affected limb particularly to the extremity of the affected limb. The adjust pressure function may be activated on demand or at a periodicity selected to reduce or minimize risk of damage the affected limb or extremity.

In the illustrative embodiments of FIGS. 22, 23, 24, 27, 28 the exemplary compression devices are shown with a cover in place. It is to be appreciated that removal of the cover would reveal a drive system, control, power, communications systems and other components of a compression device embodiment as described elsewhere herein adapted for utilization as a tourniquet. In another specific configuration a compression device configured for use as a tourniquet alone or in combination with a smart wound patch may be used to provide post-surgery hemostasis at a catheter insertion site or other surgical site. In one specific embodiment, the compression device is configured for use on an upper thigh at a vascular access site wherein the smart sensor path is optimized for adjusting the compression force at the site based on indicia of hemostasis. In one aspect, this type of compression device is adapted to provide simultaneous and even tension to the compression strap(s) such that the resultant force is primarily a downward movement of the compression device (or optional force distribution pad as described elsewhere or sensor pad or wound dressing) against the affected limb so as to produce the desired compression forces and resultant level of blood flow cessation.

Compression Device Configured for Adaptive Fit Control for Prosthesis

Figure 29:
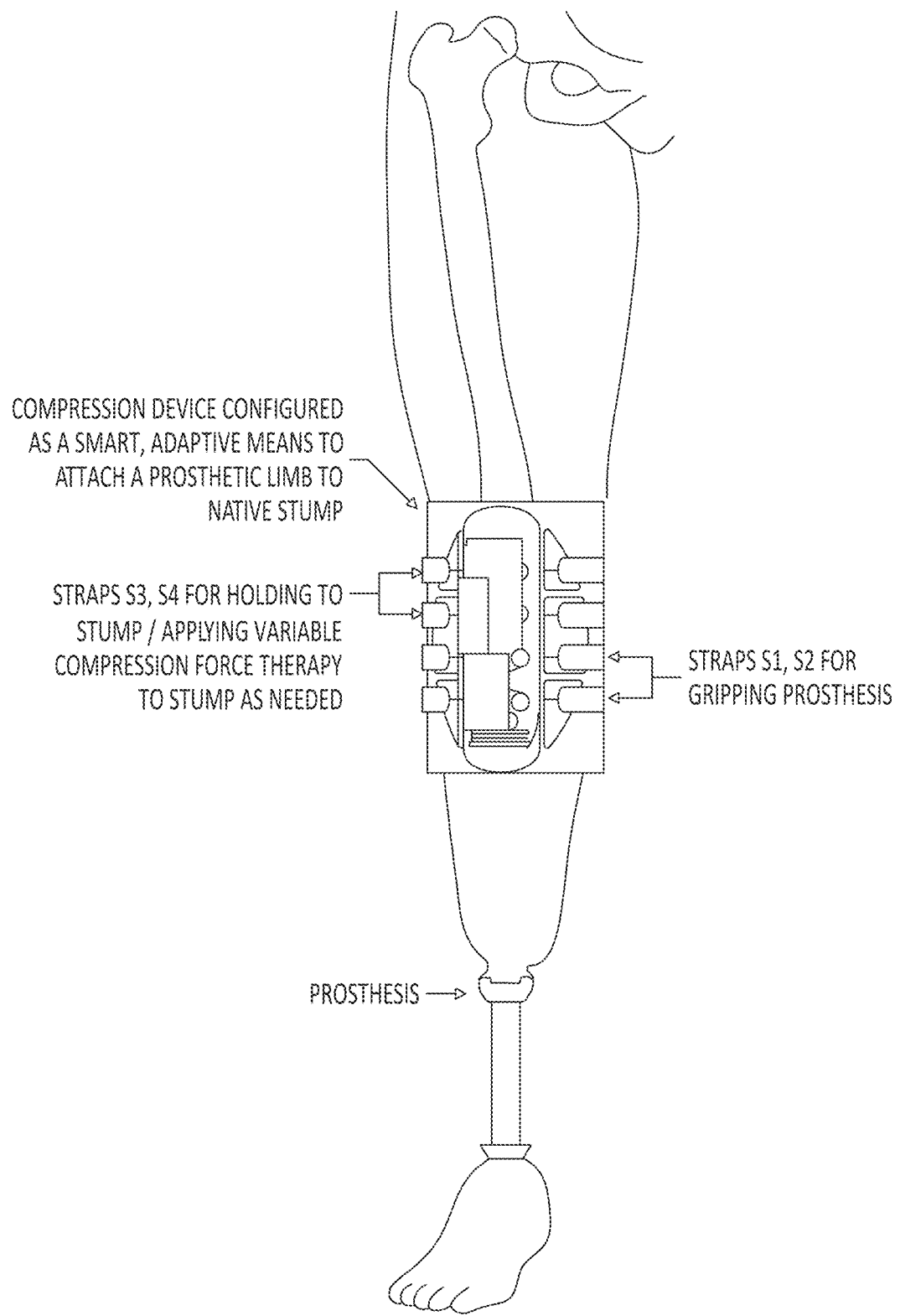
FIG. 29 is a front view of a subject with an amputated portion of the right leg and an associated lower leg and foot prosthetic coupled to the amputated stump using an embodiment of a compression device configured for this purpose.

In still other alternative configurations, one or more or a combination of the compression devices or methods of operation of one or more compression devices described herein may be scaled in size, modified, or adapted to be suitably configured to provide compression to an amputated limb sufficient to secure or assist in securing a prosthetic device to the stump of the amputated limb. FIG. 29 is a front view of a subject with an amputated portion of the right leg and an associated lower leg and foot prosthetic coupled to the amputated stump using an embodiment of a compression device configured for this purpose. The illustrated compression device is configured as a smart, adaptive means to attach a prosthetic limb to a native stump. In this configuration, straps S1 and S2 operate to provide a grip force to secure the prosthesis to the stump. The hold force may vary dynamically based on activity such as walking, running or standing. Straps S3, S4 are engaged with the stump of the amputated limb to provide controllable compression force, massage or fluid circulation therapy as needed Like straps S1, S2, the straps S3, S4 attached to the limb stump may also be modified based on activity level. FIG. 30 a front view of a subject with an amputated portion of the right leg as in FIG. 29. The compression device configuration in FIG. 30 includes a compression device A that is similar to that described in FIG. 29. The configuration in FIG. 30 also includes an additional compression device B that is positioned to provide compression therapy or massage to the thigh or other limb of the amputated stump. In this way, compression device A may be used entirely to securing the prosthesis and compression device B is position and operates to provide patient comfort.

In one aspect, there are one or more compression devices provided on the device to be positioned along the stump to provide for massage or stimulation therapy. In another alternative aspect, one or more compression devices are configured to hold the prosthetic device in position against the stump. As a result of the controllable and configurable nature of the various embodiments of a compression device, the stump may be provided with compression therapy without compromise to the stability and positioning of the prosthesis to the stump. In one specific configuration, one compression device is configured to provide a hold force on a portion of the prosthesis to be maintained adjacent to the stump and two or more compression devices are provided to the portion of the stump adjacent to the prosthesis connection point. In another aspect, one or more compression devices or different segments of a single compression device are operated to perform two different functions. One portion of the compression device operates to hold the prosthetic in place relative to the stump. The compression device may be outfitted with a receptacle configured to receive and then apply hold force to a corresponding component on the prosthetic. In another portion of the compression device, there is provide variable and controllable hold force to aid in maintaining the prosthetic in position relative to the stump such as by maintaining the position of a strap or harness. In addition or optionally, the portion of the compression device engaged with the patient's stump may also provide constant, variable, graduated or massaging compression forces to the stump portion coupled to the compression device. The operation of this portion of the compression device may be responsive to a user's comfort, activity level, a subjective determination of the user or an objective treatment recommendation such as massage or release at timed intervals based on time of day or activity. In various other aspects, the compression device may be configured with a display, a touch screen display, control buttons, sensors or other accessories as described herein as suited to the adaptation of the compression device to this use category. As described herein, the operational characteristics of the compression device configured for use with a prosthesis may be controlled or monitored remotely using a smart phone, handheld device or other suitable mode of communication.

Compression Device Configured for Operation on Patient with Inoperable Peripheral Arterial Disease In still other alternative configurations, one or more or a combination of the compression devices or methods of operation of one or more compression devices described herein may be scaled in size, modified, or adapted to be suitably configured to provide compression therapy to a patient with inoperable peripheral arterial disease. In these configurations, the operation of the compression device is commonly adapted to address two clinical burdens common to these patient populations, namely, limb ischemia and risk of amputation along with systemic vascular dysfunction and involvement of other vascular beds that pertains to cardiovascular complications, such as myocardial infarction and stroke. In one aspect, there are one or more compression devices are configured for use by a patient with an inoperable condition wherein the compression devices are adapted and configured for foot/calf compression, calf/thigh compression, foot/calf/thigh compression in any configuration in support of a compression regime suited to the disease state of the patient. In one aspect, the sequencing of the compression devices is used in or out of sequence with the heart cycle to assist in moving oxygenated blood out to the lower limbs and extremities. In still further aspects, compression devices and operating parameters may be adapted for advantageous use by patients having one of more of infrainguinal bypass grafting, local vascular dysfunction, lower extremity angioplasty and systemic dysfunction. The compression device based therapy may be intermittent, sequential, graduated or sequenced to provide a desired benefit to the patient receiving therapy. In one aspect, compression cycle of the compression devices produces a pressure of more than 100 mm Hg, 110 mm Hg or 120 mmHg or other pressure level as programmed into the compression device controller. During relaxation cycles the compression device can be operated to provide any level of pressure below that provided during the compression cycle to as low as 0 mm Hg or only sufficient pressure to maintain the compression device in position on the patient. While desiring not to be bound by theory, it is believed that compression devices as described herein and configured for these patient classes may provide clinical results and performance comparable or superior to those achieved by intermittent compression provided by pneumatic compression devices. In one aspect of this or other configurations of a compression device, one or more pressure sensors or other devices used to measure systolic/diastolic pressure is provided in the compression device along with controller instructions to monitor blood pressure and adjust compression levels to enable blood pressure measurements. In still other aspects, embodiments of the compression devices described herein may similarly deliver important clinical implications in grafted limbs when an increase in graft flow is required: (a) prevention of graft failures in low-output cardiac conditions; (b) contraindication to anticoagulation, and (c) during the peripheral vascular readjustment in late postoperative phase that often results in an increase in peripheral resistance. As a result, embodiments of the compression devices described herein are believed to provide an alternative to but equally conservative method for lower limb blood flow augmentation. As a result, the various alternative configurations and operational characteristics of compression device embodiments so configured to delivery intermittent compression of the lower limb may be a reliable, noninvasive therapeutic option, ameliorating claudication and assisting infrainguinal bypass graft flow. Additional features, characteristics and operational parameters of compression devices configured for these patient categories may be appreciated with reference to the following: "The Treatment of Peripheral Arterial Disease with Mechanical Compression and Angioplasty with Focus on Vascular Dysfunction;" Husmann, Marc (2016, Mar. 2). "The Treatment of Peripheral Arterial Disease with Mechanical Compression and Angioplasty with Focus . . . " Retrieved from www.researchgate.net/publication/ 281726960; Delis, Konstantinos T. et al. Effects of intermittent pneumatic compression of the calf and thigh on arterial calf inflow: A study of normal, claudicants, and grafted arteriopths. Accepted for publication Jul. 10, 2000; Surgery 2001; 129:188-95; Delis, Konstantinos T. et al. Haemodynamic effect of intermittent pneumatic compression of the leg after infrainguinal arterial bypass grafting. British Journal of Surgery 2004; 91: 429-434; Husmann, Marc et al. Integrity of venoarteriolar reflex determines level of microvascular skin flow enhancement with intermittent pneumatic compression. Journal of Vascular Surgery December 2008: Volume 48, Number 6: 1509-1513; Husmann, Marc et al. Long-term effects of endovascular angioplasty on orthostatic vasocutaneous autoregulation in patients with peripheral athereosclerosis. Journal for Vascular Surgery November 2006: Volume 44, Number 5: 993-997; Husmann, Marc et al. Successful lower extremity angioplasty improves brachial artery flow-mediated dilation in patients with peripheral arterial disease. Journal for Vascular Surgery November 2008: Volume 48, Number 5: 1211-1216, each of which is incorporated herein by reference in its entirety.

Compression Device Configured for Operation on a Patient Having Obstructive Sleep Apnea In still other alternative configurations, one or more or a combination of the compression devices or methods of operation of one or more compression devices described herein may be scaled in size, modified, or adapted to be suitably configured to provide compression therapy to a patient having obstructive sleep apnea. In one aspect, there are one or more compression devices along the legs of the patient configured to operate while the patient sleeps. In one aspect, the operation of the compression devices is configured to be responsive to the patient respiration cycle, the patient sleep cycle, the patient's use or operation of a breath assistance device alone or in any combination. In one illustrative example, a compression device system arranged for this use is configured to operate on an auditory signal of patient's breathing such as snoring or other breath signature recognized by the compression device controller or on a signal received from a breath assistance device such as a CPAP or similar respiration assistance device. In another aspect, the patient with sleep apnea wears a compression device that provides intermittent, constant, timed or other desired compression therapy during the day prior to the retiring to sleep when no compression therapy is applied. In another aspect, the compression device is operated to provide an active compression therapy benefit comparable to the benefit provided by a patient wearing a passive compression device with a 20 mm Hg applied pressure for a duration of 10-12 hours. In one aspect, the compression device is operated for one to four hours prior during the patient waking hours with the compression device removed during sleep. Additional other operational characteristics and possible benefits for compression devices configured for this patient class are described in "Attenuation of Obstructive Sleep Apnea by Compression Stockings in Subjects with Venous Insufficiency," by S. Redolfi, et al, Am J Respir Crit Med Vol 184, pp. 1062-1066, 2011, the entirety of which is incorporated herein by reference.

Compression Device Configured for Operation on a Hospitalized Patient to Prevent Deep Vein Thrombosis (DVT)

In still other alternative configurations, one or more or a combination of the compression devices or methods of operation of one or more compression devices described herein may be scaled in size, modified, or adapted to be suitably configured to provide compression therapy to a hospitalized patient with deep vein thrombosis. In one aspect, there are one or more compression devices positioned along the legs of the patient to provide for massage or stimulation therapy to aid in the treatment or alleviation of symptoms of deep vein thrombosis.

In one embodiment, the compression device worn by the patient is in communication with other patient based sensors and may adapt compression therapy in response to patient data from in room sensor or information, in addition or optionally, in response to sensors provided with and operation in cooperation with the compression device. In some embodiments, the compression device may be modified to have a wired or wireless connection to the hospital network or in-room sensors. Additionally or optionally, the compression device may be modified to provide data on settings, use, duration, compression dose or other compression therapy parameters to an electronic medical record. In still other configurations, the compression device may be configured to provide or operate with available sensors such as an ultrasound sensor, strain gauge or other sensor used to detect an indicia of patient vascular health.

Compression Device Configured for Use to Provide Region Specific Massage to a Patient with Lymphedema.

In still other alternative configurations, one or more or a combination of the compression devices or methods of operation of one or more compression devices described herein may be scaled in size, modified, or adapted to be suitably configured to provide compression therapy to treat or alleviate systems related to lymphedema.

In one configuration, one or more compression devices may be worn by a patient to orient the compression in alignment with the patient's lymph nodes or other site of swelling identified for compression therapy. Alternative embodiments include the use of the one or more compression devices with or without an undergarment including attachment of the compression devices on, in or within a garment to facilitate donning and doffing the compression devices in the affected area of the patient anatomy.

The compression device or combination of compression devices for a particular limb are applied to the associated region of the body or regions of the body in any combination. Thereafter, each of the compression devices is activated in a predetermined sequence which applies controllable, repeatable pressure to the muscles, vasculature and lymphatic system in any desired sequence depending upon desired clinical results or patient specific needs such as localized swelling of a body part or limb. In one aspect, the one or more compression devices is activated in a serial compression mode. The serial compression mode of controllable compression therapy acts on the associated muscles and veins to mimic the action of walking. As a result of serial compression mode operation, blood is moved through the veins towards the heart so as to prevent pooling of blood in the lower limbs.

Still further, configurations of one or more controllable compression devices may be used to create gradient compression on the leg muscles and veins to provide a massaging effect which imitates the natural flow of lymph from the distal end of the limb (foot) toward the trunk of the body, mimicking the action of leg movement, such as walking, to move blood and fluids through the veins towards the heart. It is to be appreciated that the one or more controllable compression devices may be adapted and configured to vary the amount of compression, rate of the application of compression, hold time for compression, release time/rate of compression for each compression device operating alone or in conjunction with one or more other controllable compression devices as described herein. In one aspect, the one or more compression devices are applied to the patient and then sequentially operated to provide a gradient of pressure in the leg or any limb by adjusting the compression profile of each of the controllable compression devices. In one exemplary embodiment there is provided appropriate operational parameters of the one or more compression devices from ankle to knee (or mid-thigh) to a pressure of 45-50 mmHg at the ankle, 35 mmHg at the calf, and 30 mmHg at the thigh. Other pressure gradients are possible. Moreover, the duty cycle of the compression cycle includes a compression period and a relaxation period. In one embodiment, the compression cycle is 10 seconds, 15 seconds, 20 seconds with a relaxation cycle of from 60 seconds or more between successive compression cycles. In some embodiments, the compression cycle is timed to operate in sequence with all or a portion of the patient's heartbeat.

Exemplary configurations include, for example, (a) compression devices worn on both legs and operated in sequence to provide compression therapy to a portion of the lymphatic system in the legs; (b) compression devices worn on both legs configured with a support garment in the form of pants and operated in sequence to provide compression therapy to a portion of the lymphatic system in the legs; (c) compression devices worn on one or both arms and the chest and operated in sequence to provide compression therapy to a portion of the lymphatic system in the arms and the chest; (d) compression devices worn on worn on one or both arms and the chest and operated in sequence to provide compression therapy to a portion of the lymphatic system in the arms and the chest configured with a support garment in the form of a jacket; (e) compression devices worn on one or both arms and operated in sequence to provide compression therapy to a portion of the lymphatic system in the arms; (f) compression devices worn on worn on one or both arms and operated in sequence to provide compression therapy to a portion of the lymphatic system in the arms and configured with a support garment in the form of jacket sleeves as shown in FIG. G1, for example; (g) compression devices worn on one or both hands and operated in sequence to provide compression therapy to a portion of the hands in support of lymphatic therapy; and (h) compression devices worn on one or both hands and operated in sequence to provide compression therapy to a portion of the hands in support of lymphatic therapy and configured with a support garment in the form of gloves or mittens.

Compression Device Configured for Sports or Activity Related Recovery

In still other alternative configurations, one or more or a combination of the compression devices or methods of operation of one or more compression devices described herein may be scaled in size, modified, or adapted to be suitably configured to provide compression therapy to aid in sport preparation, sport training or recovery after activity specific, sports or athletic exertion. In these various embodiments, the compressive forces delivered by the one or more compression devices is aligned with muscle groups, joints or soft tissue to provide massage to affected areas alone or in combination with other affected regions as a result of the completed activity. In some configurations, one or more compression devices are adapted for use in blood flow restriction (BFR) training.

Figure 31:
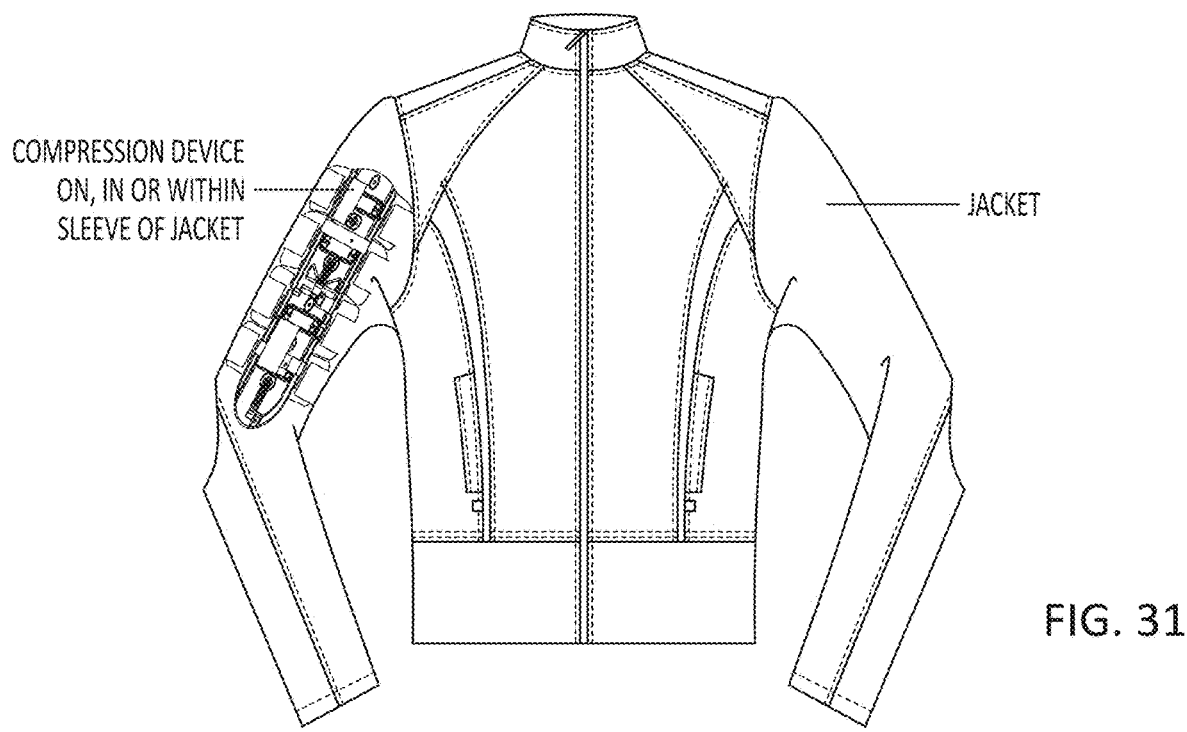
FIG. 31 is an exemplary compression device on, in or within a sleeve of a jacket.
Figure 32:
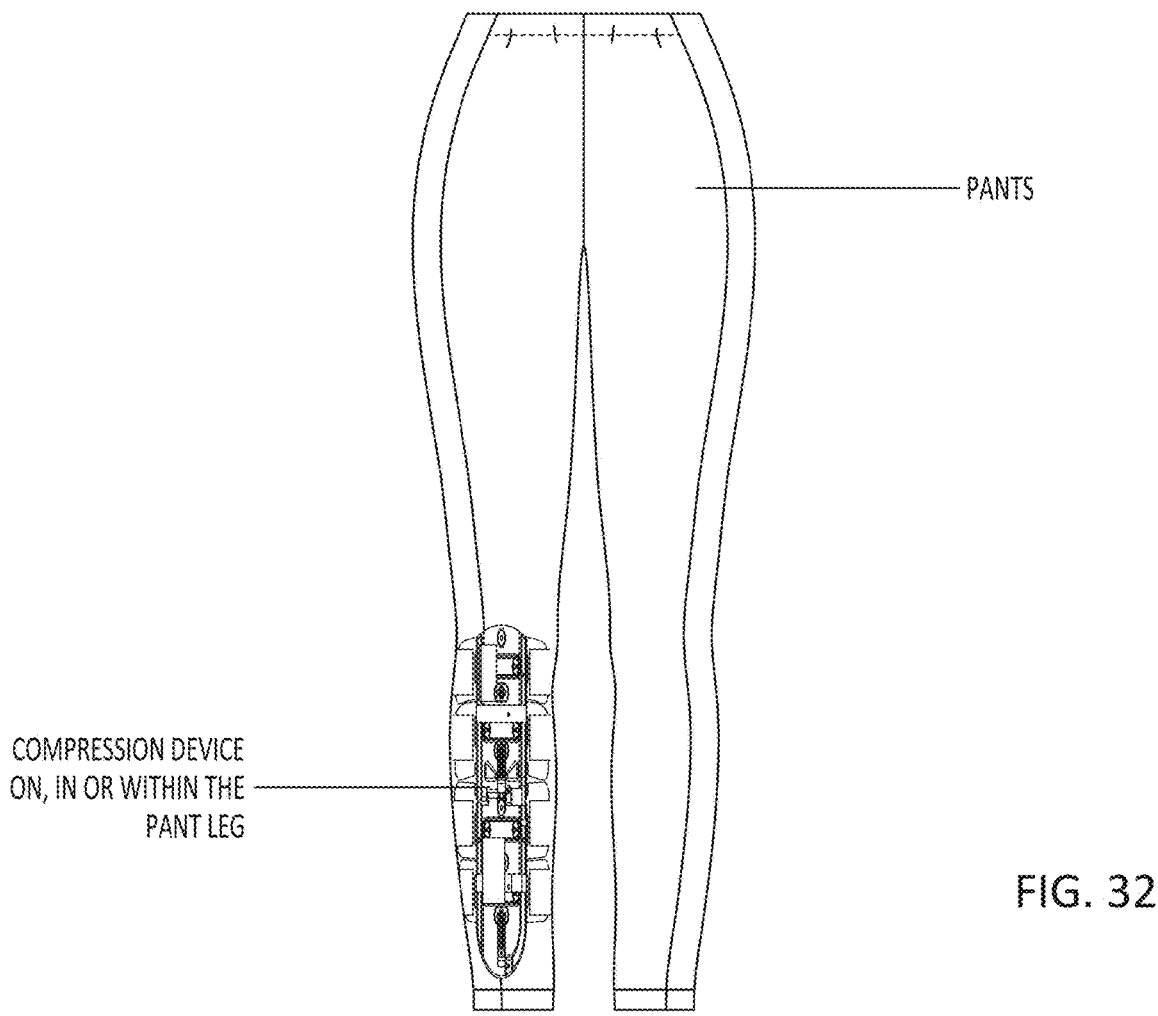
FIG. 32 is an exemplary compression device on, in or within the leg of pants.

In one aspect, the one or more compression devices provided for this purpose are oriented and grouped according to the degree and manner of compression therapy suited to the desired outcome such as lactic acid removal, fluid removal, swelling, muscle fatigue and the like. As a result, the compression device or groups of devices are aligned to provide compression therapy or massage to affected areas. The compression devices may be placed on the affected area directly or incorporated on, in or within a suitable garment with a form factor appropriate to ease of donning and doffing while retaining the compression device in position for a particular therapy session. Exemplary garment form factors include, by way of example, a total body coverall, a jump suit, a pair of pants, a pair of shorts, a jacket, one or set of sleeves, gloves, boots, shoes, stockings, socks or a wrap. Exemplary compression devices are illustrated on, in or within a sleeve of jacket (see FIG. 31) or the leg of pants (see FIG. 32). In various embodiments, individual compression devices may be linked together wirelessly or via wired connections to a central compression controller that operates the drive or drives on each associated compression member according to the overall desired therapeutic effect as well as the specific location of a compression member in relation to other compression devices.

The compression device or combination of compression devices for a particular limb are applied to the associated region of the body or regions of the body in any combination in relation to the therapy sought in relation to the completed activity, sport or athletic event. Thereafter, each of the compression devices is activated in a predetermined sequence which applies controllable, repeatable pressure to the muscles, vasculature and soft tissues including the lymphatic system in any desired sequence depending upon desired clinical results or patient specific needs such as pain, discomfort, localized swelling of a body part or limb. In one aspect, the one or more compression devices is activated in a serial compression mode. The serial compression mode of controllable compression therapy acts on the associated muscles and veins to mimic the action of walking. As a result of serial compression mode operation, blood is moved through the veins towards the heart so as to prevent pooling of blood in the lower limbs. Additionally or optionally, the mode of operation of one or more compression devices may be to move fluids away from the heart or to provide compression at levels associated with massage—ranging from gentle to firm to deep tissue, based on degree of compression applied.

Still further, configurations of one or more controllable compression devices may be used to create gradient compression on the limbs to provide a massaging effect to imitate natural fluid flows toward or away from the core, or toward or away from an extremity as desired in a particular therapy. It is to be appreciated that the one or more controllable compression devices may be adapted and configured to vary the amount of compression, rate of the application of compression, hold time for compression, release time/rate of compression for each compression device operating alone or in conjunction with one or more other controllable compression devices as described herein. In one aspect, the one or more compression devices are applied to the patient and then sequentially operated to provide a gradient of pressure in the leg or any limb by adjusting the compression profile of each of the controllable compression devices. Moreover, the duty cycle of the compression cycle includes a compression period and a relaxation period. In one embodiment, the compression cycle is 10 seconds, 15 seconds, 20 seconds with a relaxation cycle of from 60 seconds or more between successive compression cycles. In some embodiments, the compression cycle is timed to operate in sequence with all or a portion of the patient's heartbeat.

Exemplary activity, sports and athletic recovery configurations include, for example, (a) compression devices worn on both legs and operated in sequence to provide compression therapy to a portion of the muscles, joints, soft tissue or lymphatic system in the legs; (b) compression devices worn on both legs configured with a support garment in the form of pants and operated in sequence to provide compression therapy to the muscles, joints, soft tissue or lymphatic system in the legs; (c) compression devices worn on one or both arms and the chest and operated in sequence to provide compression therapy to the muscles, joints, soft tissue or lymphatic system in the arms and the chest; (d) compression devices worn on worn on one or both arms and the chest and operated in sequence to provide compression therapy to the muscles, joints, soft tissue or lymphatic system in the arms and the chest configured with a support garment in the form of a jacket; (e) compression devices worn on one or both arms and operated in sequence to provide compression therapy to the muscles, joints, soft tissue or lymphatic system in the arms; (f) compression devices worn on worn on one or both arms and operated in sequence to provide compression therapy to the muscles, joints, soft tissue or lymphatic system in the arms and configured with a support garment in the form of jacket sleeves; (g) compression devices worn on one or both hands and operated in sequence to provide compression therapy to muscles, joints or soft tissue of the hands or fingers; and (h) compression devices worn on one or both hands and operated in sequence to provide compression therapy to muscles, joints or soft tissue of the hands or fingers and configured with a support garment in the form of gloves or mittens.

Exemplary Additional Internal Use Medical Applications—Device is Configured for Internal/Implantable Use Compression Device for Use as a Smart Gastric Banding Device In still other alternative configurations, one or more or a combination of the compression devices or methods of operation of one or more compression devices described herein may be scaled in size, modified, or adapted to be suitably configured for implantation into the body on or about a portion of the stomach or other portion of the gut to treat or alleviate bariatric disorders.

FIG. 33 is diagram illustrating a view of a torso of a patient 10, in which stomach 11 is visible. A dynamically controlled gastric occlusion device 16 monitors at least one physiological parameter that varies as a function of food intake and controls the degree of gastric constriction of a compression device powered occluding device 12 based on the monitored physiological parameter. In another embodiment, dynamically controlled gastric occlusion device 16 controls the degree of gastric constriction provided by the compression device 12 based on time. The inner diameter of occluding device 12 dynamically increases or decreases based on time or the monitored physiological parameter to either permit or restrict the passage of food through the gastrointestinal (GI) tract. The occluding device 12 restricts passage of food (and as a result, may dramatically suppress the appetite) by creating a small stomach pouch in the upper stomach 11A and restricting a size of a stoma opening into the lower stomach 11B. By dynamically controlling the degree of gastric constriction, device 16 limits the ingestion of food to reduce caloric intake so that the patient loses weight while permitting the ingestion of water and the minimum amount of caloric energy necessary to prevent malnourishment.

Dynamically controlled gastric occlusion device 16 includes an occluding device 12, such as a compression device configured as a gastric band, and appropriate control circuitry 18 for controlling compression device operation to produce the desired degree of gastric constriction, and thus the size of the stoma opening from the stomach, provided by gastric occluding device 12. In the case of a gastric band, decreasing the inner diameter of the gastric band increases the degree of gastric constriction provided by the band. At least one sensor, such as sensor 14A and/or 14B, monitors a physiological parameter that varies as a function of food intake. An implanted control module 20 monitors and analyzes the sensed physiological parameters and dynamically controls adjustment of the gastric band 12 based on time or based on the monitored physiological parameter. When the physiological parameter so indicates, control module 20 generates and transmits an adjustment control signal to control circuitry 18 within occluding device 12. Control circuitry 18 receives the adjustment control signal and adjusts occluding device 12 accordingly. Additional details for the use and operation of a compression device for this purpose may be obtain from United States Patent Application Publication US 2006/0173238 entitled, "Dynamically Controlled Gastric Occlusion Device," which is incorporated here in its entirety.

FIG. 34 is a cross section of the lower esophagus, stomach and duodenum of a subject with a plurality of compression devices adapted for implantation and configured for constriction or manipulation of the gut. In the illustrative embodiment of FIG. 34 a gastric compression device (P1) is positioned adjacent to the pylorus or the duodenum and another (E1) is positioned along the lower esophagus at or near the lower esophageal sphincter. Three gastric compression devices (S1, S2, S3) are shown in positions along the stomach. More or fewer gastric compression devices may be added and used in sequence to obtain desired results. As described above in FIG. 33, the degree of compression force applied by the different compression devices will vary based on the desired outcome, the position of the device and inputs from one or more sensors or other criteria as described above. As described above, one or more sensors along with internal or external controls may be used to adjust the amount of constriction delivered to the stomach or gut by each compression device. The gastric compression devices in this illustrative embodiment are shown with covers and implantable housings removed to show internal details. It is to be appreciated that the number, size, length and orientation of the straps provided by any particular gastric compression device may vary from those illustrated.

Compression Device for Cardiac Reinforcement or Treatment

In still other alternative configurations, one or more or a combination of the compression devices or methods of operation of one or more compression devices described herein may be scaled in size, modified, or adapted to be suitably implanted into the body and configured to support or provide cardiac based therapy based on the adjustable and controllable characteristics of the compression device used alone to directly contact internal structures as in the gastric compression embodiments or in conjunction with a cardiac support structure. As a result, compression devices described herein may be configured to provide adjustable cardiac support or adjust the tension of a cardiac support structure. In one embodiment, the compression device used for cardiac therapy operates in an active mode to aid in heart function and cardiac output. In another embodiment, the compression device used for cardiac therapy operates in a passive or retraining mode to assist heart structure.

Figure 35:
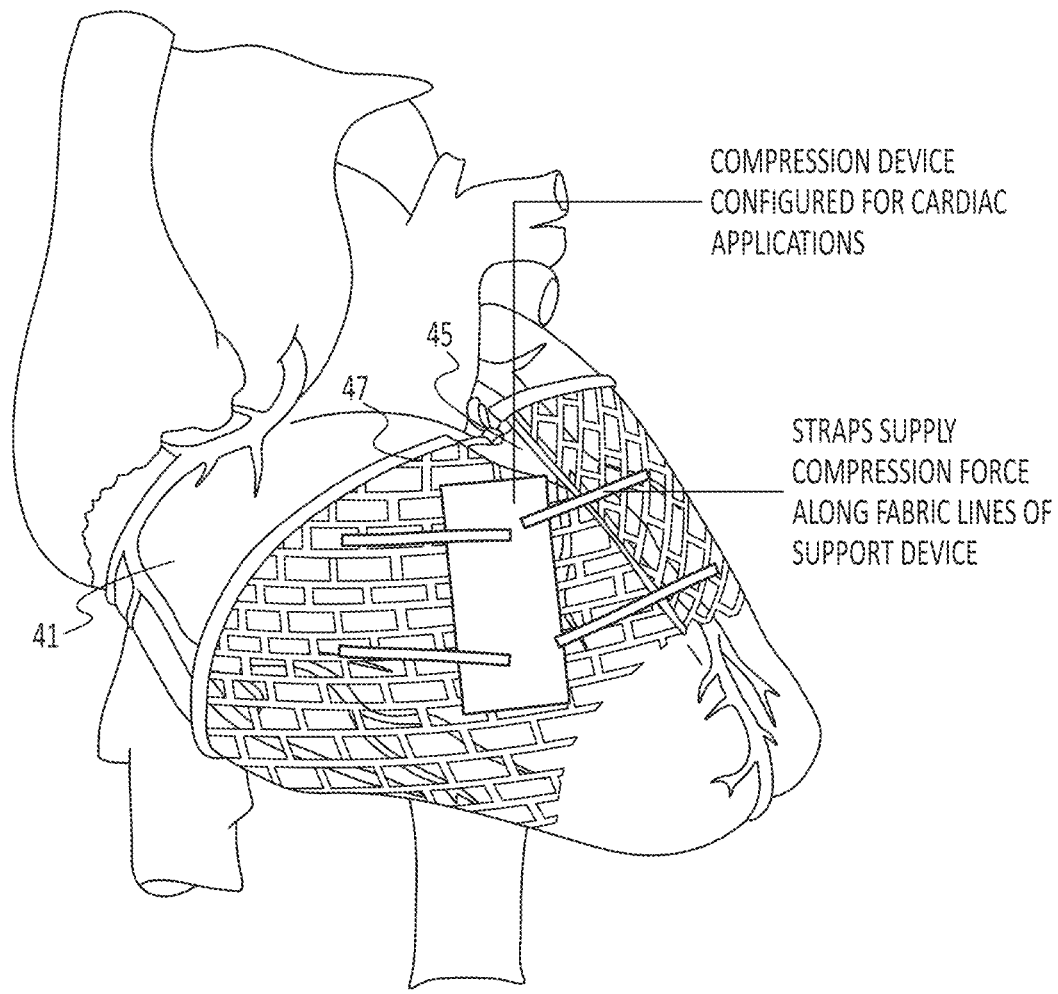
FIG. 35 illustrates the use of a cardiac compression device configured for operation with a cardiac reinforcement device with ends that encircle a portion of the heart.

FIG. 35 illustrates the use of a cardiac compression device configured for operation with a cardiac reinforcement device with ends 47, 45 that encircle a portion of the heart 41. In these illustrative embodiments the various elements forming the knit of the jacket may be coupled to the compression device in a number of different configurations depending upon the desired variation to be produced in the jacket. In this embodiment, the compression device is placed at an angle to align the pull force generated by the compression device in alignment with the general direction of the elements of the jacket. As described elsewhere, the compression device may be controlled externally after implantation an external device in communication with the compression device. Additional details, structural information and uses for the embodiment of FIG. 35 may be appreciated by reference to U.S. Pat. No. 6,077,218 entitled "Cardiac Reinforcement Device," which is incorporated herein by reference in its entirety.

Figure 37:
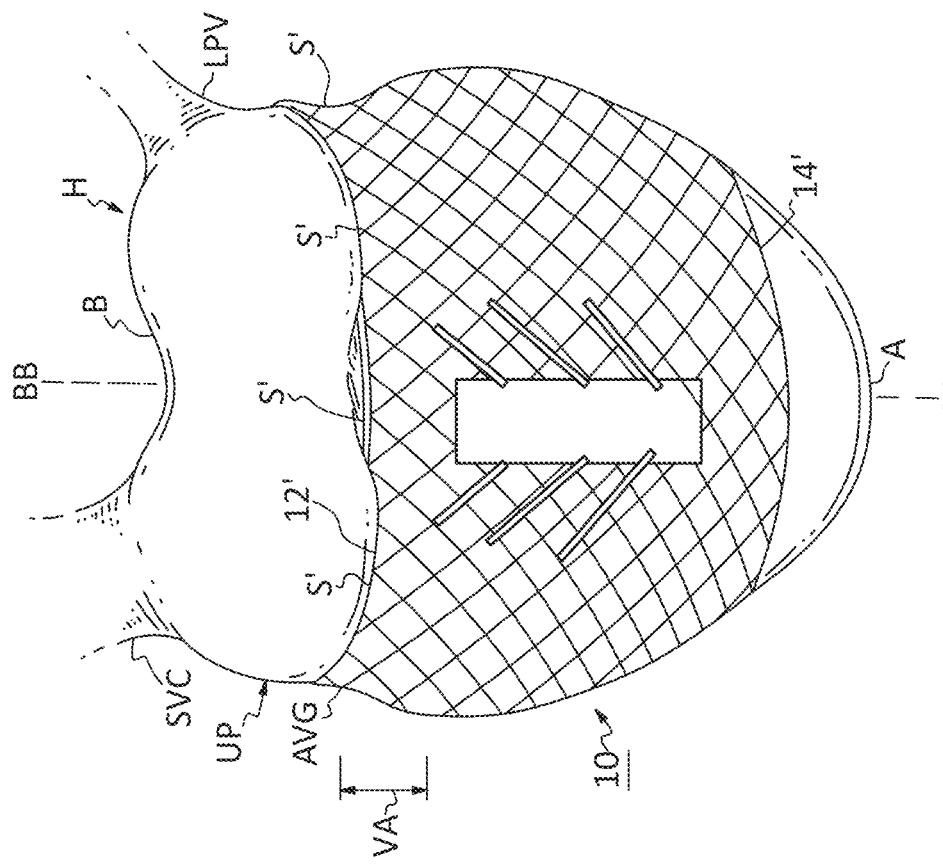
FIGS. 36 and 37 illustrate the use of a cardiac compression device configured for operation with a jacket that encloses the lower portion of the heart completely as in FIG. 36 or partially as in FIG. 37.
Figure 36:
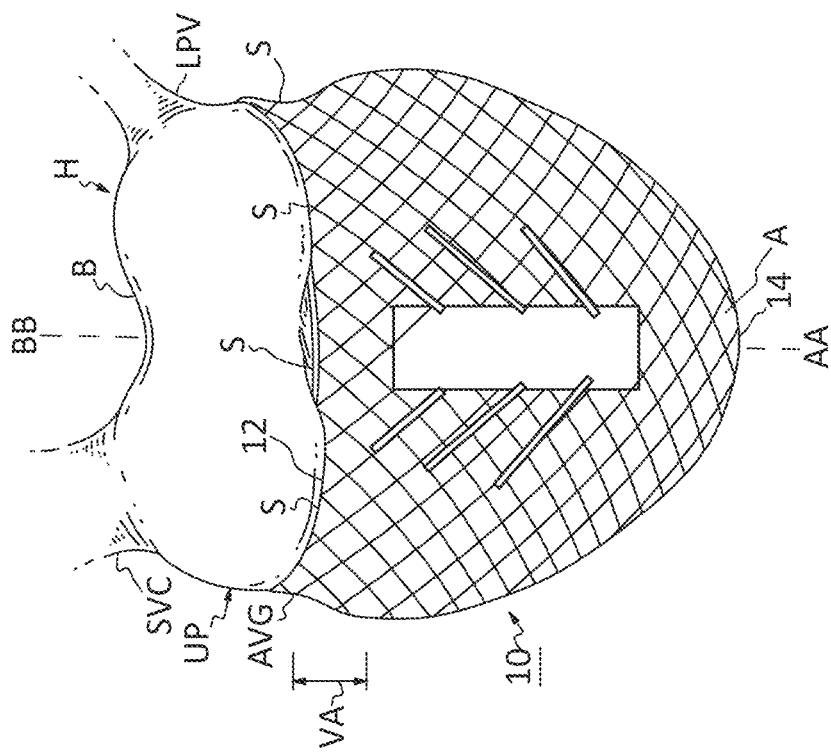

FIGS. 36 and 37 illustrate the use of a cardiac compression device configured for operation with a jacket 10 that encloses the lower portion of the heart completely as in FIG. 36 or partially as in FIG. 37. In these illustrative embodiments the various elements forming the knit of the jacket may be coupled to the compression device in a number of different configurations depending upon the desired variation to be produced in the jacket. As described elsewhere, the compression device may be controlled externally after implantation an external device in communication with the compression device. Additional details, structural information and uses for the embodiments of FIGS. 36 and 37 may be appreciated by reference to U.S. Pat. No. 6,123,662 entitled "Cardiac Disease Treatment and Device," which is incorporated herein by reference in its entirety. Additional details, structural information and additional support structures and uses may be appreciated by reference to U.S. Pat. No. 8,092,367 entitled "Method of External Stabilization of the Base of the Heart," which is incorporated herein by reference in its entirety.

Non-Medical and/or Medical Applications

Compression Devices as a Pump

In still other alternative configurations, one or more or a combination of the compression devices or methods of operation of one or more compression devices described herein may be scaled in size, modified, or adapted to be suitably configured to provide sequential compression to provide controllable peristaltic flow of a fluid in a deformable tube. In one configuration, three compression devices are positioned along a suitable tubing that may be deformed under the forces generated by the compression devices. The compression devices are then operated in the desired sequence to more the fluid in the tube to mimic the sequential squeezing of fluid by the rollers in a peristaltic pump.

Figure 38:
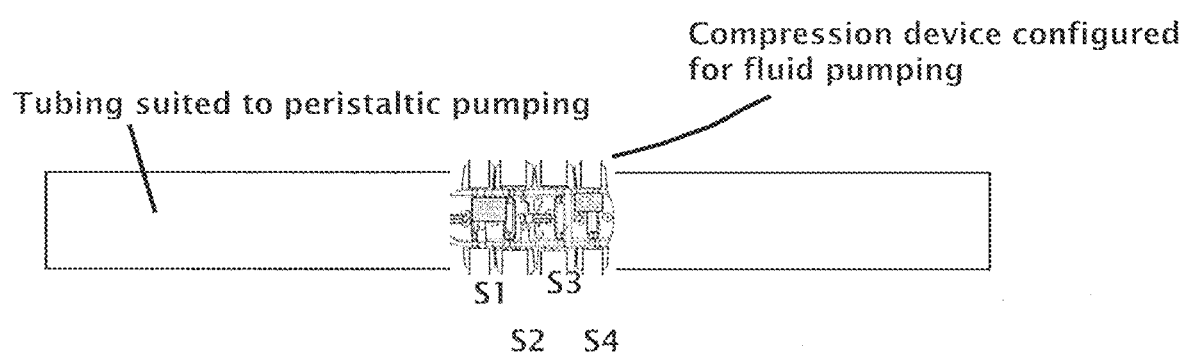
FIG. 38 illustrates a compression device that can be used as a pump.

One or more compression devices may be adapted to fit on tubing in laboratory or industrial setting for use in a peristaltic pumping system. FIG. 38 illustrates a compression device have four compression straps S1, S2, S3 and S4. In this illustrated embodiment, the operation of the compression device to sequence S1, S2, S3 and S4 will move from left to right in the illustrated orientation. In contrast, operation of the compression device to sequence S4, S3, S2 and S1 will move fluid within the tubing from right to left in the illustrated orientation. One or more compression devices may be provided with more or fewer straps or straps of different geometry or orientation as needed for a particular fluid pumping scenario. The compression device controller will actuate the compression drive system depending on the tubing characteristics such as length, wall thickness and durometer as well as the characteristics of the fluid being pumped and the desired flow rate.

Compression Devices within Footwear

In still other alternative configurations, one or more or a combination of the compression devices or methods of operation of one or more compression devices described herein may be scaled in size, modified, or adapted to be suitably configured to provide added functionality to footwear. In one aspect, one or more compression devices integrated into a footwear article is operated to augment venous flow, to apply compression to the vascular beds of the foot, or otherwise increase beneficial or desired fluid flow in the foot engaged with the compression device enhanced footwear. This compression may be either non-medical, as a massage or for securement for example, or for a medical use to treat venous ulcers or venous insufficiency as described herein.

Figure 39A:
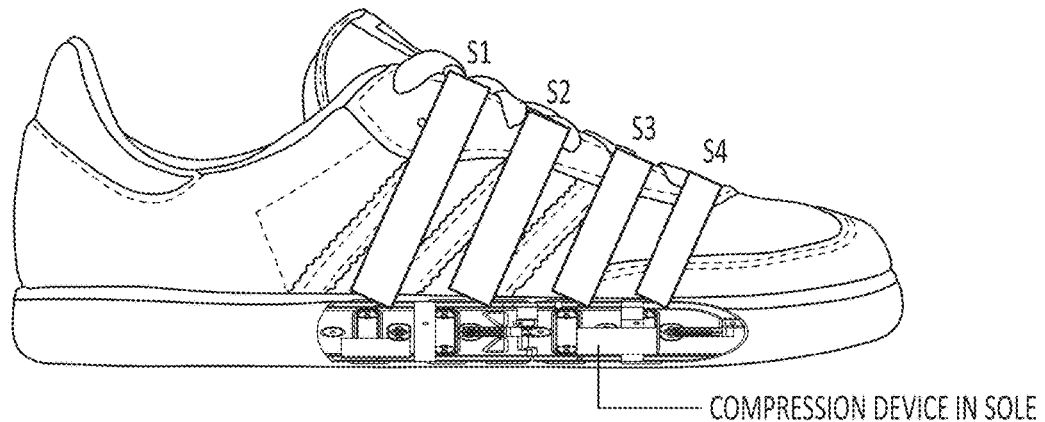
FIGS. 39A and 39B are bottom up and perspective views, respectively, of a shoe having an embodiment of a compression device integrated into the sole of the shoe with straps arranged along on, in or within the upper portion of the shoe.
Figure 40:
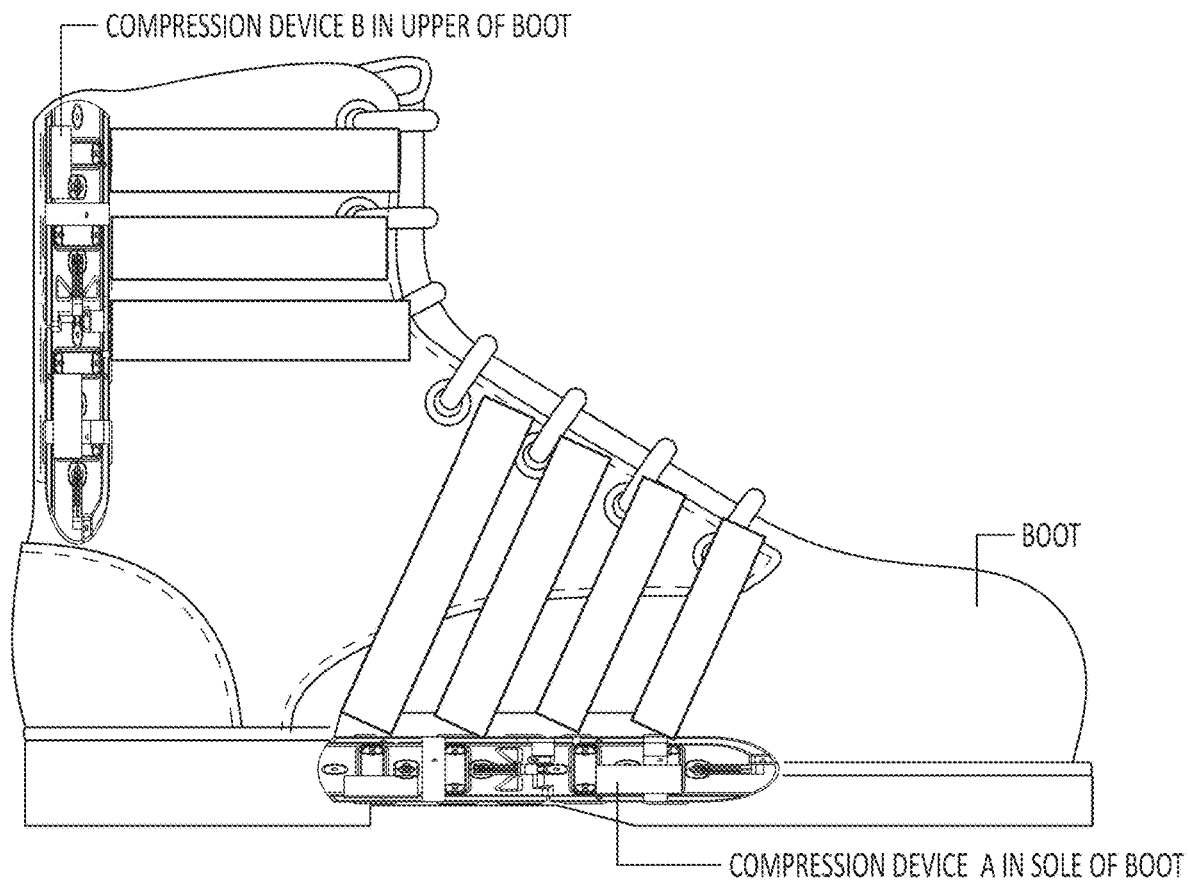
FIG. 40 is a perspective view of a boot having a compression device integrated into the sole and the upper of the boot.
Figure 39B:
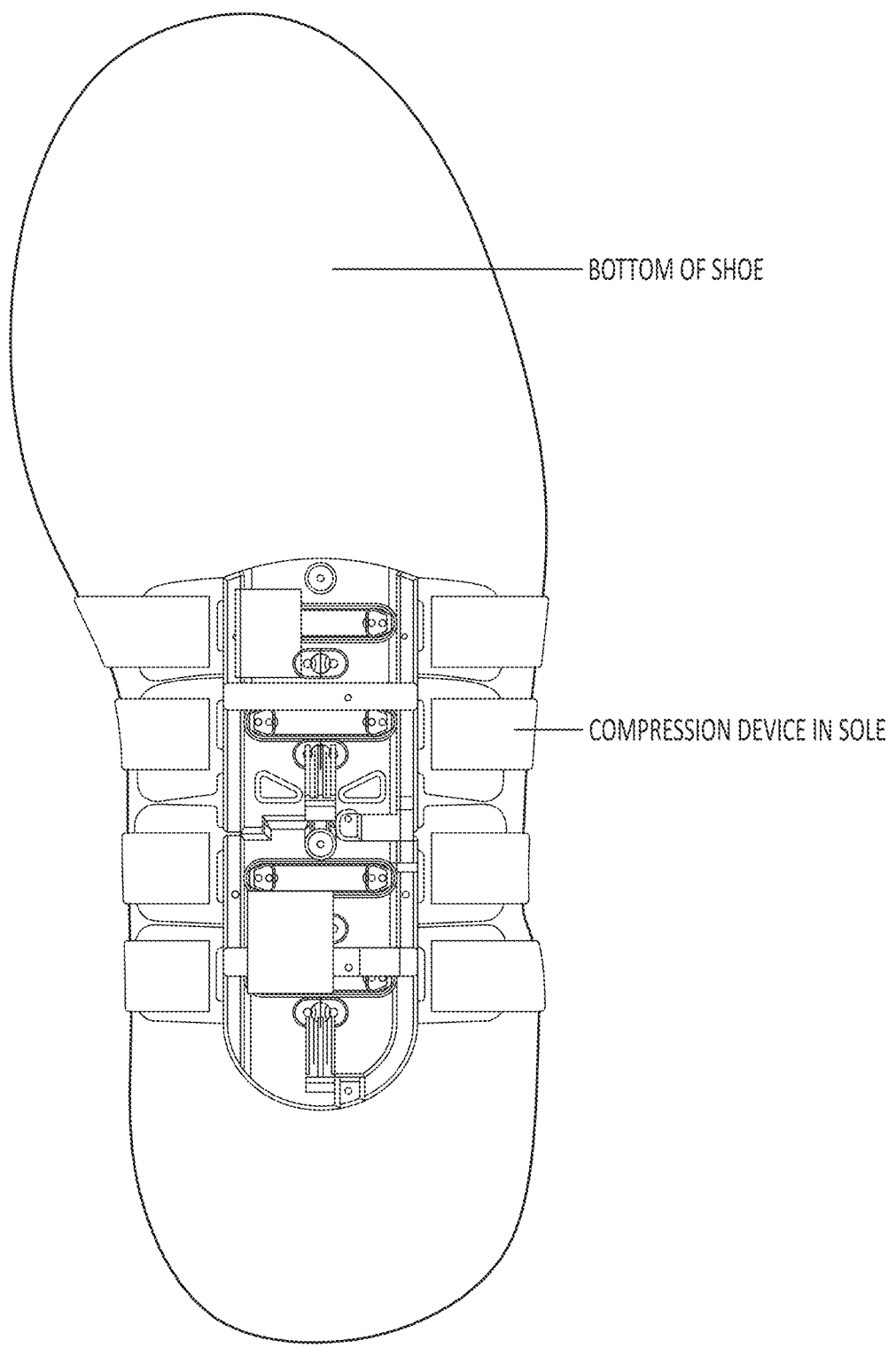

FIGS. 39A and 39B are bottom up and perspective views, respectively, of a shoe having an embodiment of a compression device integrated into the sole of the shoe with straps S1-S4 arranged along on, in or within the upper portion of the shoe. FIG. 40 is a perspective view of a boot having a compression device integrated into the sole and the upper of the boot. The compression device A is integrated into the sole of the boot with straps S1-S4 arranged along on, in or within the upper portion of the bottom part of the boot. The compression device B is integrated into the upper portion of the boot with straps S1-S3 arranged along on, in or within the upper portion of the boot. Other compression device configurations are possible and may vary depending upon the use and design of the footwear. The footwear configured compression devices may also include recharging devices configured to collect and store energy based on shoe impact. Footwear compression devices may also be configured to provide additional support to the foot including adapting the degree of compression applied or specific tension in each strap depending upon configuration and level of desired support. These compression devices may also include sensors to detect or provide feedback to the user on foot health such as swelling. The footwear compression devices may be responsive to user comfort, activity level or to provide massage as well as other uses.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for providing compression treatment to a subject, the system comprising:
   a wearable compression device configured to provide compression to a body part of the subject, the wearable compression device comprising a compression plate, one or more motors disposed on the compression plate, one or more compression mechanisms configured to be wrapped around the body part and tightened or loosened by the one or more motors;
   one or more sensors configured to gather at least one of subject position, device position, activity data, pressure data, data related to a physiological status of the body part, and subject physiological data, wherein the one or more sensors includes a force sensor positioned on the compression plate and configured to face the body part of the subject;
   a processor configured to process the data received from the one or more sensors; and
   a wireless communication module configured to send the data received from the one or more sensors.

2. The system of claim 1, wherein the position data comprises data related to whether the subject is standing, lying down, or sitting.

3. The system of claim 1, wherein the pressure and compression data comprises data related to compression level/magnitude, compression duration, frequency, dwell time, and treatment duration.

4. The system of claim 1, wherein data gathered by the one or more sensors comprises data related to leg girth.

5. The system of claim 1, wherein data gathered by the one or more sensors comprises data related to activity level.

6. The system of claim 1, wherein data gathered by the one or more sensors comprises data related to oxygen level.

7. The system of claim 1, wherein data gathered by the one or more sensors comprises data related to at least one of venous filling time, venous volume, venous reflux, and venous index.

8. The system of claim 1, wherein data gathered by the one or more sensors comprises data related to blood pressure.

9. The system of claim 1, wherein the one or more sensors comprise an accelerometer or gyroscope.

10. The system of claim 1, wherein data gathered by the one or more sensors comprises data related to activity patterns of the subject.

11. The system of claim 1, wherein the one or more sensors comprises at least one of a heart rate sensor, blood pressure sensor, impedance sensor, clot formation detection, blood flow measurements, ultrasound sensor, wound size measurement, temperature sensor, gas sensor, blood chemistry, posture sensor, and an accelerometer.

12. The system of claim 1, wherein data gathered by the one or more sensors comprises data related to at least one of the subject's body part girth, body part volume, posture, physical activity level, venous filling time, venous reflux, venous index, ulcer status, heart rate, oxygen level, temperature, blood pressure, sweat biochemistry, impedance, temperature, oxygen level, electrical activity, and blood flow dynamics.

13. The system of claim 1, wherein at least one of the one or more sensors is independent of the device.

14. The system of claim 1, wherein the processor is also configured to receive and process patient feedback data.

15. The system of claim 1, wherein the system is configured to send information related to data from the one or more sensors to a remote system or clinician.

16. The system of claim 1, wherein the system is configured to gather data related to operation of the one or more motors.

17. The system of claim 15, wherein the data related to operation of the one or more motors comprises data related to current draw and load on the one or more motors.

* * * * *